US006831202B2

(12) United States Patent
Dahl et al.

(10) Patent No.: US 6,831,202 B2
(45) Date of Patent: Dec. 14, 2004

(54) COMPOSITIONS COMPRISING OCTAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 377 days.

(21) Appl. No.: 10/012,546

(22) Filed: Dec. 12, 2001

(65) Prior Publication Data

US 2002/0147373 A1 Oct. 10, 2002

Related U.S. Application Data

(60) Provisional application No. 60/262,842, filed on Jan. 19, 2001, and provisional application No. 60/323,883, filed on Sep. 20, 2001.

(51) Int. Cl.$^7$ ............................. C07C 13/28; C07C 7/00
(52) U.S. Cl. ........................... 585/352; 585/16; 585/21; 585/800; 585/802; 585/803; 117/68; 117/69; 117/70
(58) Field of Search ............................. 585/803, 21, 16, 585/800, 802, 352; 117/68, 69, 70

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,952,748 A | 8/1990 | Alexander | |
| 4,952,749 A | 8/1990 | Alexander | |
| 4,952,757 A | 8/1990 | Alexander | |
| 4,982,049 A | 1/1991 | Alexander | |
| 5,017,734 A | 5/1991 | Baum | |
| 5,019,665 A | 5/1991 | Partridge | |
| 5,126,274 A * | 6/1992 | McIver et al. | 436/140 |
| 5,245,104 A | 9/1993 | Cullick | |
| 5,268,513 A | 12/1993 | Shen | |
| 5,298,666 A | 3/1994 | Shen | |
| 5,306,851 A | 4/1994 | Wu | |
| 5,334,228 A * | 8/1994 | Ashjian et al. | 44/347 |
| 5,347,063 A | 9/1994 | Shen | |
| 5,369,213 A | 11/1994 | Shen | |
| 5,380,947 A | 1/1995 | Chen | |
| 5,382,684 A | 1/1995 | Moini | |
| 5,397,488 A | 3/1995 | Chen | |
| 5,410,092 A | 4/1995 | Shen | |
| 5,414,189 A * | 5/1995 | Chen et al. | 585/801 |
| 5,430,193 A | 7/1995 | Shen | |
| 5,461,184 A | 10/1995 | Swanson | |
| 5,498,812 A | 3/1996 | Bradway | |
| 5,576,355 A | 11/1996 | Chen | |
| 6,235,851 B1 | 5/2001 | Ishii | |

FOREIGN PATENT DOCUMENTS

| EP | 0399851 | 11/1996 |
|---|---|---|
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", Fuel, vol. 58, 228–230, (Mar. 1979).
Balaban, et al., Systemic Classification and Nomenclature of Diamond Hydrocarbons–I, Tetrahedron, 34. pp, 3599–3606, (1978), no month.
Badziag, P., et al., "Nanometre–sized Diamonds are More Stable than Graphite", Nature, vol. 343, pp. 244–245, and 517 (Jan. 1990).
Bagrii, Ye, et al., "Catalytic breakdown of Paraffinic Hydrocarbons in the Presence of Adamantanes", Petrol. Chem USSR, vol. 30, No. 2, pp. 131–134, (1990), no month.
Chung, et al., Recent Development in High–Energy Density Liquid Fuels, Energy and Fuels, 13, pp. 641–649, (1999), no month.
Dahl, J., et al., Diamondoid Hydrocarbons as Indicators of Natural Oil Cracking, Nature, 399, pp. 54–57, (1999), no month.
Drexler, Eric K., Nanosystems: Molecular Machinery Manufacturing and Computation, John Wiley & Sons, pp. 238–249, (1992), no month.
Fort, Jr., et al., Adamantane: Consequences of the Diamondoid Structure, Chem. Rev., 64, pp. 277–300, (1964) no month.
Hala, V.S., et al., "Analyse Unds erwendung on Pyrolyseol", Juhrgang, pp. 85–87, (Feb. 1971) In German–English Abstract on p. 85, considered to extent of abstract.
Landa, S., "Adamantane and Its Homologues", Current Science, Gangalore, India, Vo. 32, pp. 485–489 (1963), no month.
Lin, et al., Natural Occurrence of Tetramantane ($C_{22}H_{36}$), Pentamantane ($C_{26}H_{32}$), and Hexamantane ($C_{30}H_{36}$) in a Deep Petroleum Reservoir, Fuel, 74:10, pp. 1512–1521, (1995), no month.
McKervey, Synthetic Approaches to Large Diamondoid Hydrocarbonds, Tetrahedron, 36, pp. 971–992, (1980), no month.
Machacek, V., et al., "Let Od Objeveni Adamantanu", Chemicke Listy/svazek, pp. 753–761, (1982) Russian—English Abstract on p. 761, no month, considered to extent of abstract.
Oya, A, et al., "Carbonization of Adamantanes to a Graphitizable Carbon", Fuel, vol. 60, pp. 667–669, (Aug. 1981).

(List continued on next page.)

Primary Examiner—Elizabeth D. Wood
(74) Attorney, Agent, or Firm—Burns, Doane, Swecker & Mathis, L.L.P.

(57) ABSTRACT

Disclosed are compositions comprising one or more octamantanes. Specifically disclosed are compositions comprising 25 to 100 weight percent of one or more octamantanes. Also disclosed are novel processes for the separation and isolation of octamantane components into recoverable fractions from a feedstock containing at least a higher diamondoid component which contains one or more octamantane components.

39 Claims, 67 Drawing Sheets

OTHER PUBLICATIONS

Petrov, A., "Hydrocarbons of Adamantane Series as Indicies of Petroleum Catagenesis Process", *Advances in Organic Geo Chemistry,* 6$^{th}$International Meeting on Organic Geochemistry, pp. 517–522 (1973), no month.

Prusova, D., Liquid Chromatography of Adamantanes and Carbon Adsorbents, *J. Chrom,* 234, pp. 1–11, (1982), no month.

Rollman, L., et al., "Adamantanes From Petroleum, with Zeolites", American Chemical Study, 210$^{th}$ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo [11.7.1.1$^{2.18}$.0$^{3.16}$.0$^{4.13}$.0$^{5.10}$.0$^{6.14}$.0$^{7.11}$.0$^{15.20}$]–Docosane, a Bastard Tetramantane",*J. of the Am. Chem. Soc.,* 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.,* vol. 114, No. 2, pp 497–505, (1992), no month.

Supryadkina, NY, et al., "Catalytic Dealkylation of Alkyladamantanes", *Petrol. Chem., USSR,* vol. 28, No. 2, pp. 103–110, (1988), no month.

Tominaga, K., et al., "Next–generation Fine Chemicals Raw Material–Adamantane", *Chem. Econ & Eng. Review,* vol. 17, No. 10, pp. 23–29, (Oct. 1985).

Vodicka, L, et al., "High Performance Liquid Chromatography of Halogeno Derivatives of Adamantane and Diamantane", *J. Chrom,* 270, pp. 199–205, (1983), no month.

Wingert, W., "G.c.–m.s. Analysis of Diamondoid Hydrocarbons in Smackover Petroleums", *Fuel,* vol. 71, pp. 37–42, (Jan. 1992).

* cited by examiner

FIG. 2
Example of Symmetrical
Octamantanes
[1212121] Octamantane
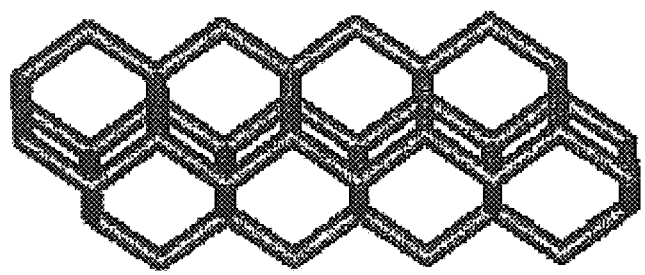
Examples Enantiomeric
[1212312] Octamantanes
*
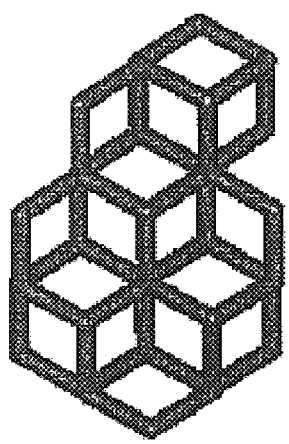 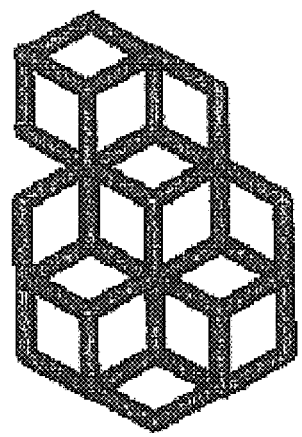
[1212312] Octamantane
* Mirror plane indicating enantiomeric pair ♦ Feedstock B
■ Feedstock A FIG. 9
A)
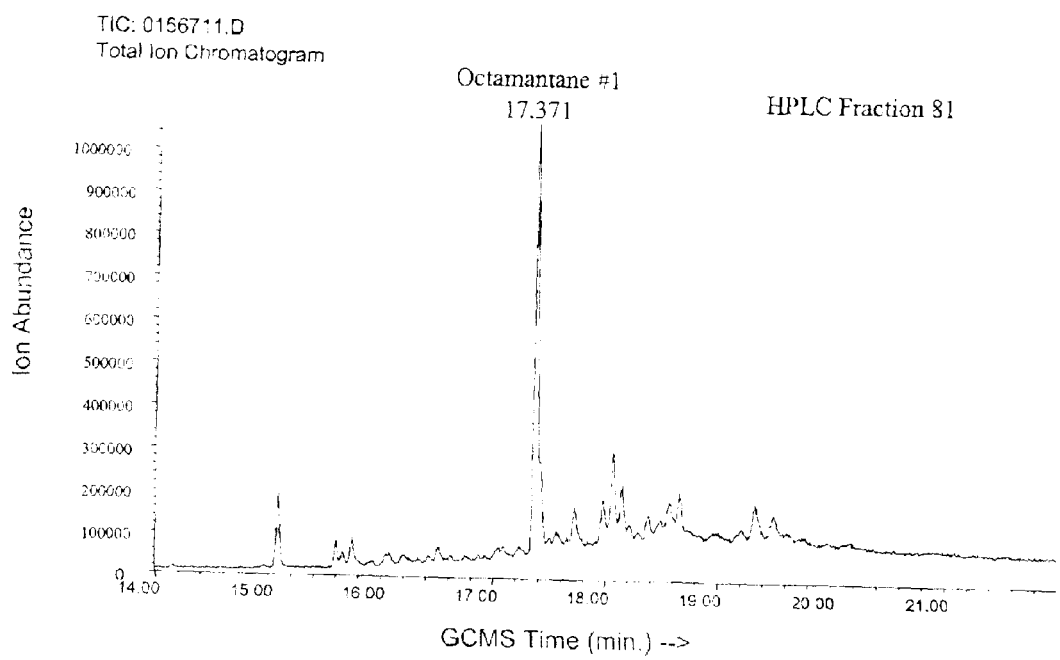
B)
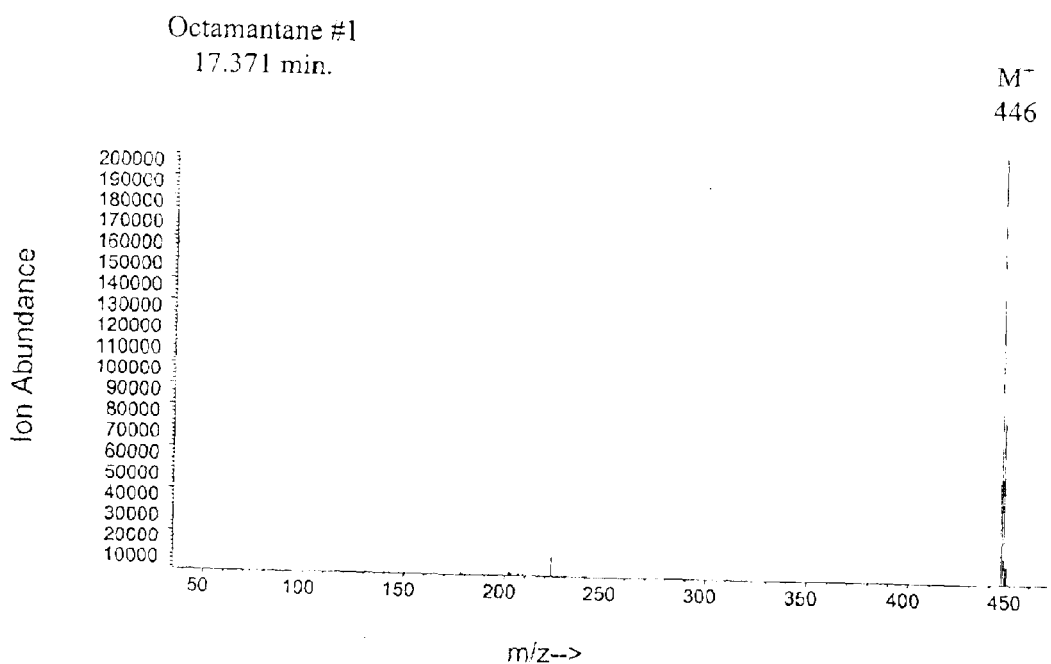

Octamantane #1
Crystals

FIG. 11

446 mol. wt. Octamantane

| ODS HPLC Fraction # | 1<br>17.36 | 2<br>17.42 | 3<br>17.48 | 4<br>17.54 | 5<br>17.77 | 6<br>17.87 | 7<br>17.91 | 8<br>18.27 | 9<br>18.51 | 10<br>18.66 | 11<br>18.72 |
|---|---|---|---|---|---|---|---|---|---|---|---|
| 57 | | | | | | | | | | | |
| 58 | | | | | | | | | | | |
| 59 | | | | | | | | | | | |
| 60 | | | | | | | | | | | |
| 61 | | | | | | | | | | | |
| 62 | | | | | | | | | | | |
| 63 | | | | | x | | | | | | |
| 64 | | | x | | | | | | | | |
| 65 | | | | | | | | | | | |
| 66 | | | | | | | | | | | |
| 67 | | | | | | | | | | | |
| 68 | | | | | | | | | | | |
| 69 | | | | | | | | | | | |
| 70 | | | | | | | | | | | |
| 71 | | | | | | | x | | | | |
| 72 | | | | | | | | | | | |
| 73 | | | | | | | | | | | |
| 74 | | | | | | | | | x | | |
| 75 | | | | | | | | | | | |
| 76 | | | | | | | | | | | |
| 77 | | | | | | | | | | | |
| 78 | | | | | | | | | | | |
| 79 | | | | | | x | | | | | |
| 80 | | | | | | | | | | x | |
| 81 | x | | | | | | | | | | |
| 82 | | | | | | | | | | | |
| 83 | | x | | | | | | | | | |
| 84 | | | | | | | | x | | | |
| 85 | | | | | | | | | | | x |
| 86 | | | | | | | | | | | |
| 87 | | | | | | | | | | | |
| 88 | | | | | | | | | | | |
| 89 | | | | | | | | | | | |
| 90 | | | | | | | | | | | |
| 91 | | | | | | | | | | | |
| 92 | | | | | | | | | | | |
| 93 | | | | | | | | | | | |
| 94 | | | | | | | | | | | |
| 95 | | | | | | | | | | | |

Numbers in cells are the individual Octaamantane retention times in minutes in our GC/MS assay.

FIG. 12
A)
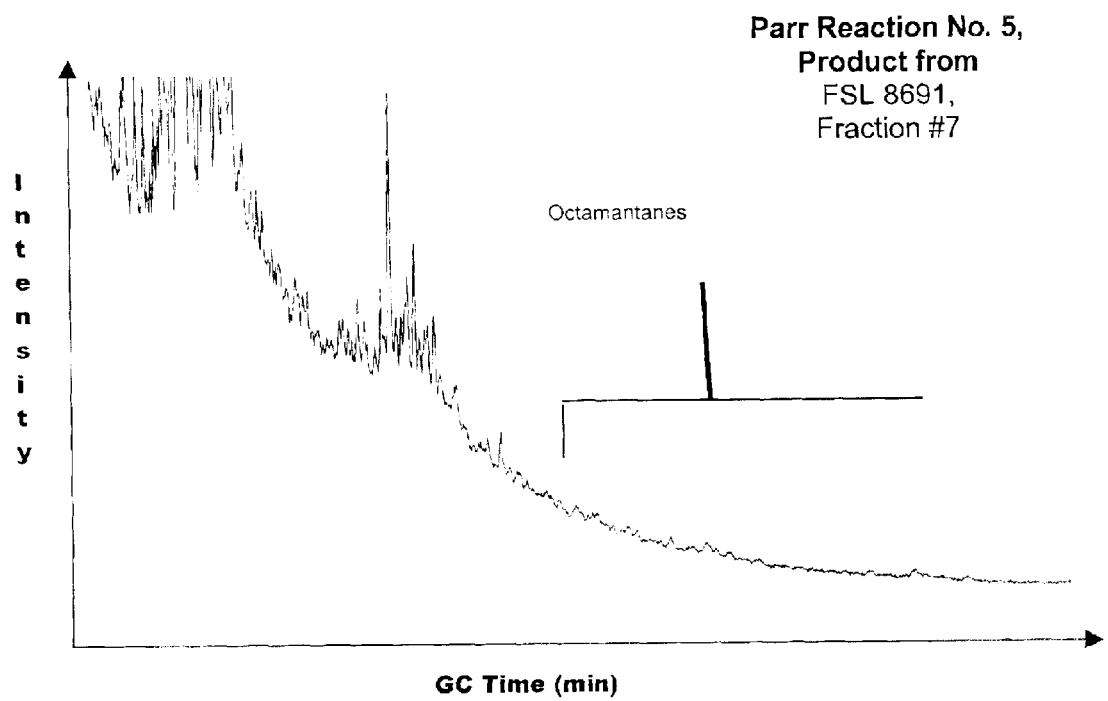
Parr Reaction No. 5,
Product from
FSL 8691,
Fraction #7
Octamantanes
GC Time (min)
B)
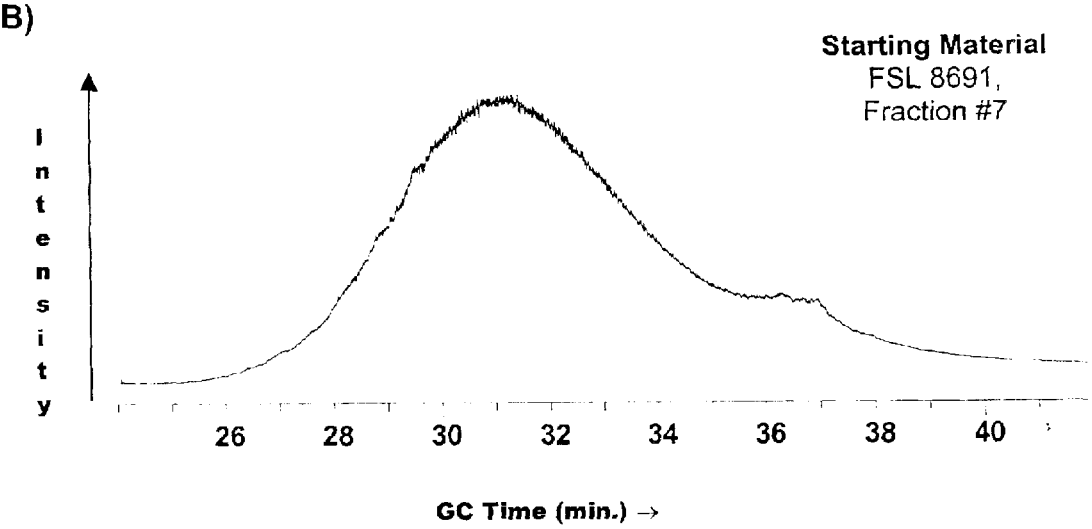
Starting Material
FSL 8691,
Fraction #7
GC Time (min.) →

FIG. 14
A)
B)
Co-crystal
Octamantane #3 and #5

FIG. 15
A)
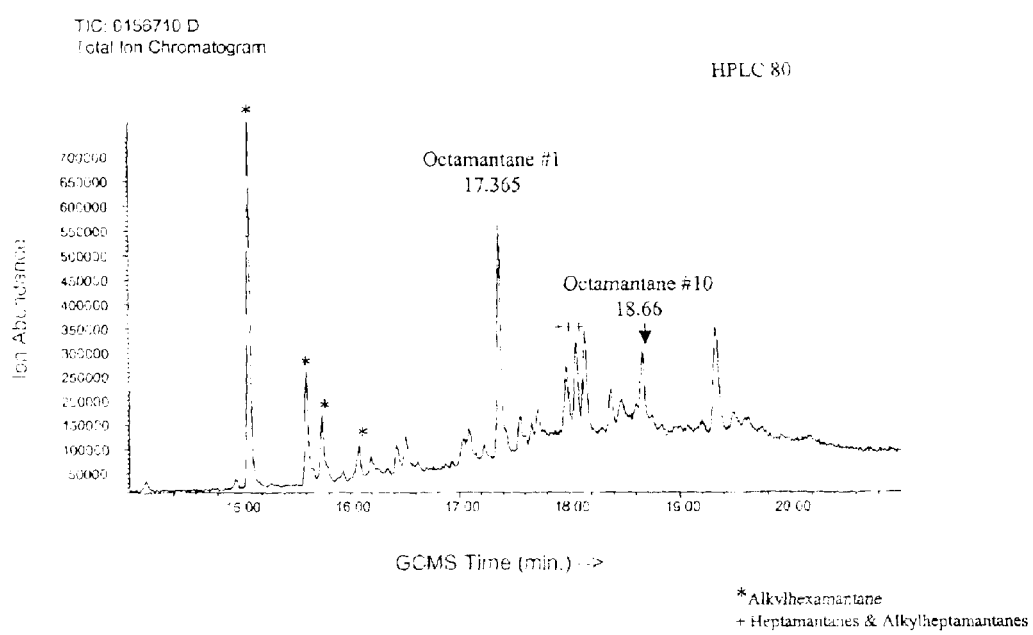
B)
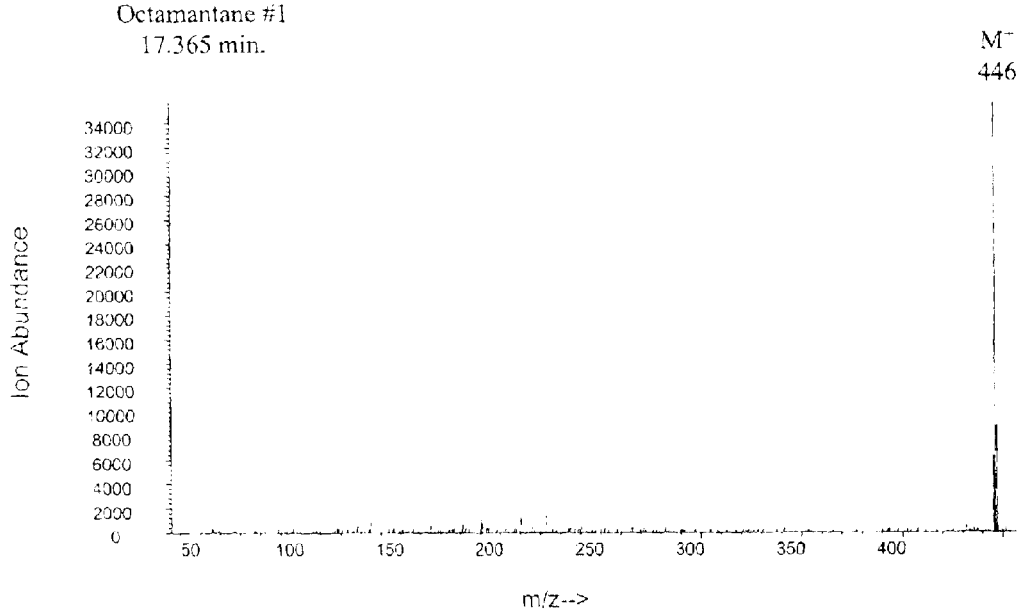

FIG. 16
A) 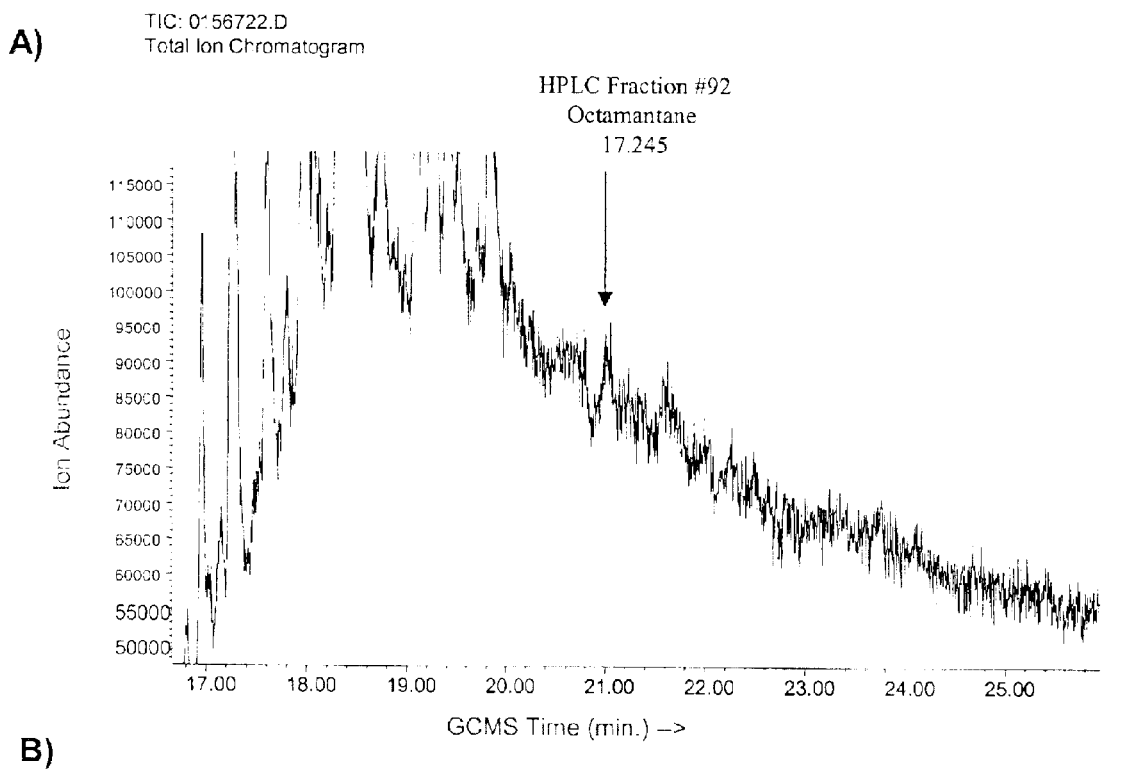
B) 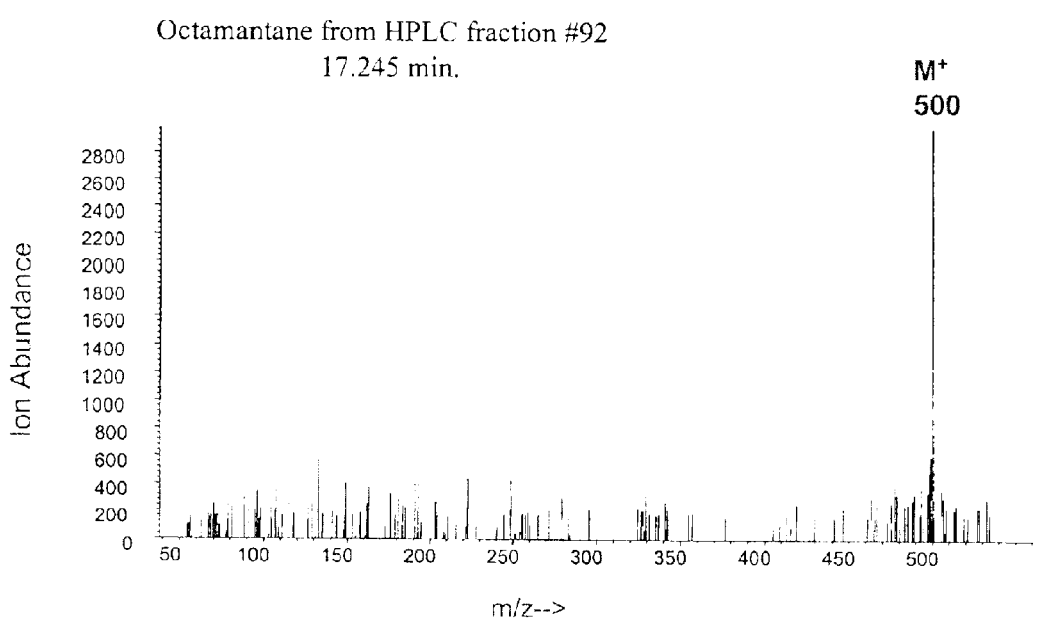

FIG. 17
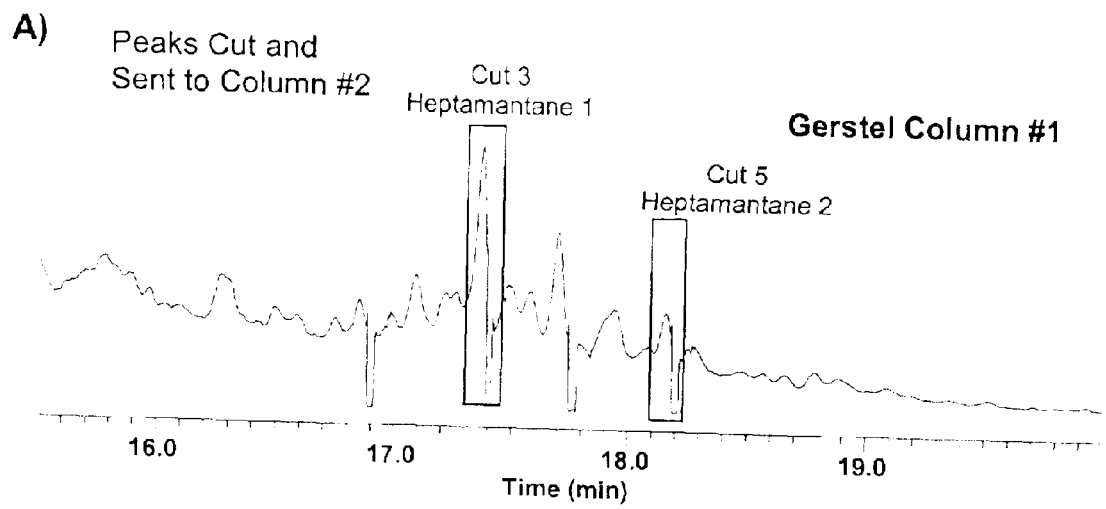
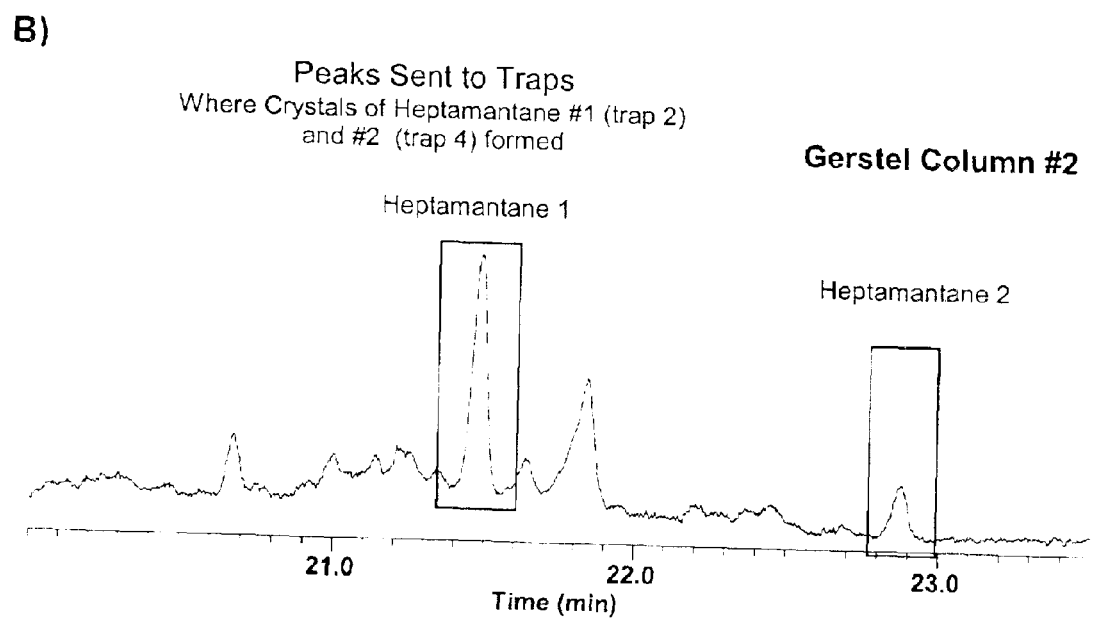

FIG. 18
A)
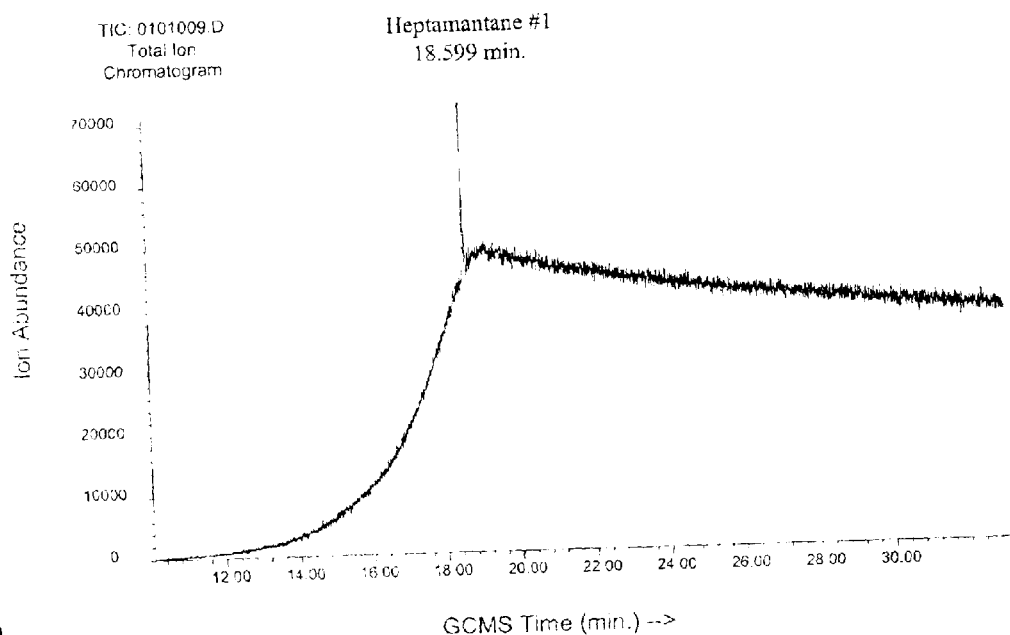
B)
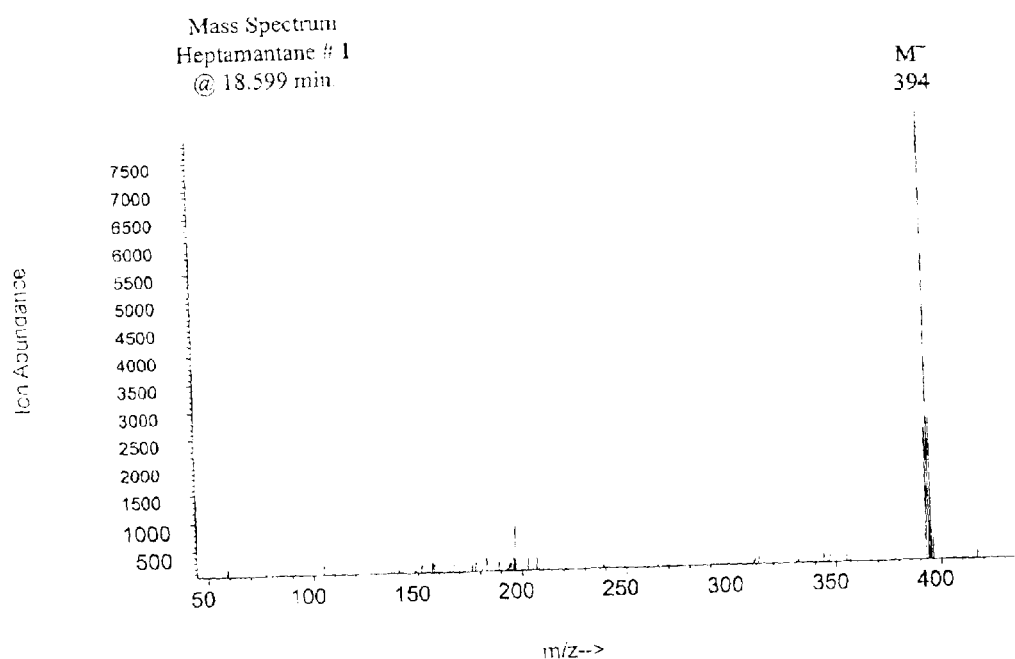

FIG. 19
A)
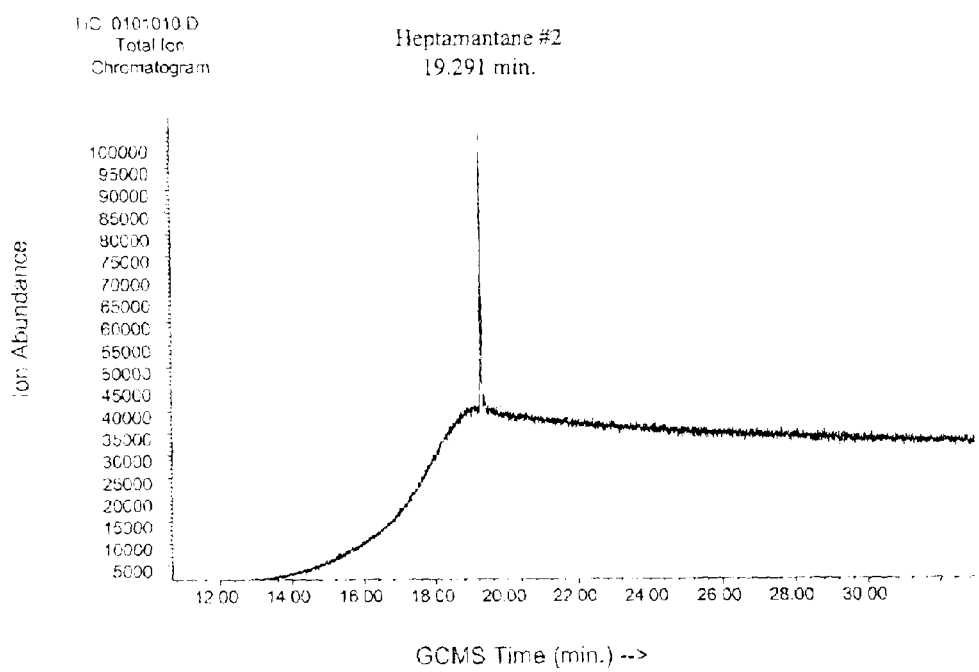
B)
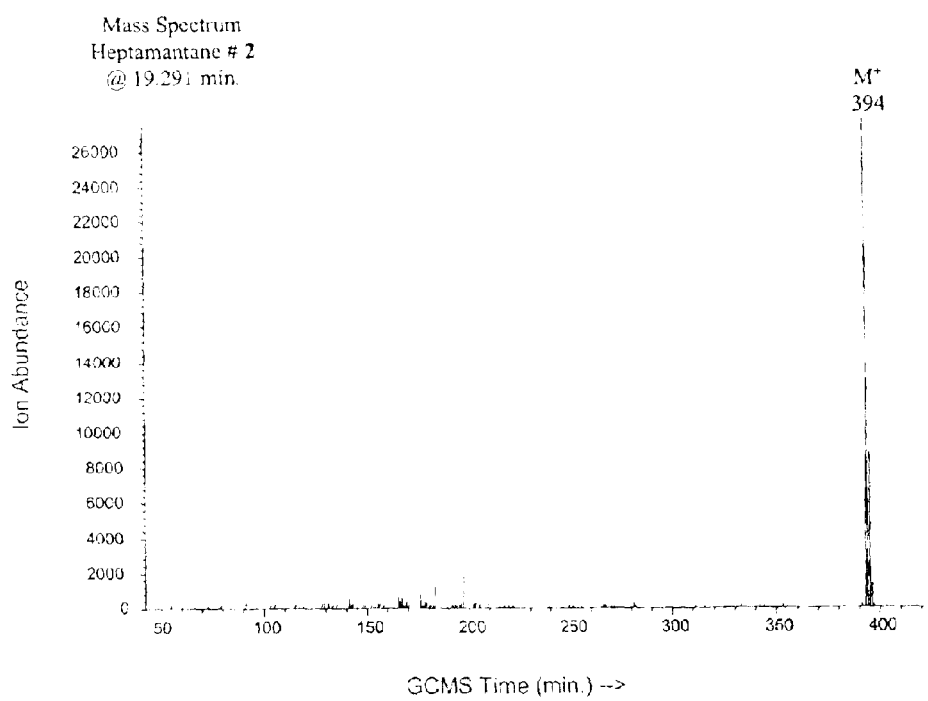

FIG. 20
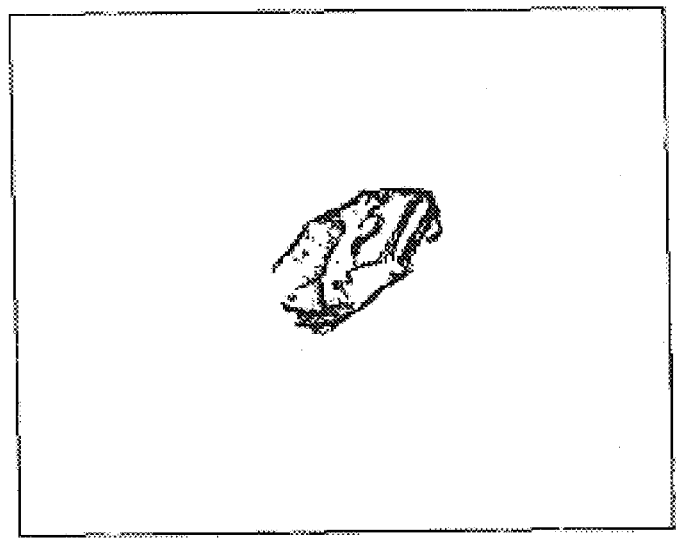
Heptamantane #1 Crystals

Heptamantane #2
Crystals

FIG. 22
A)
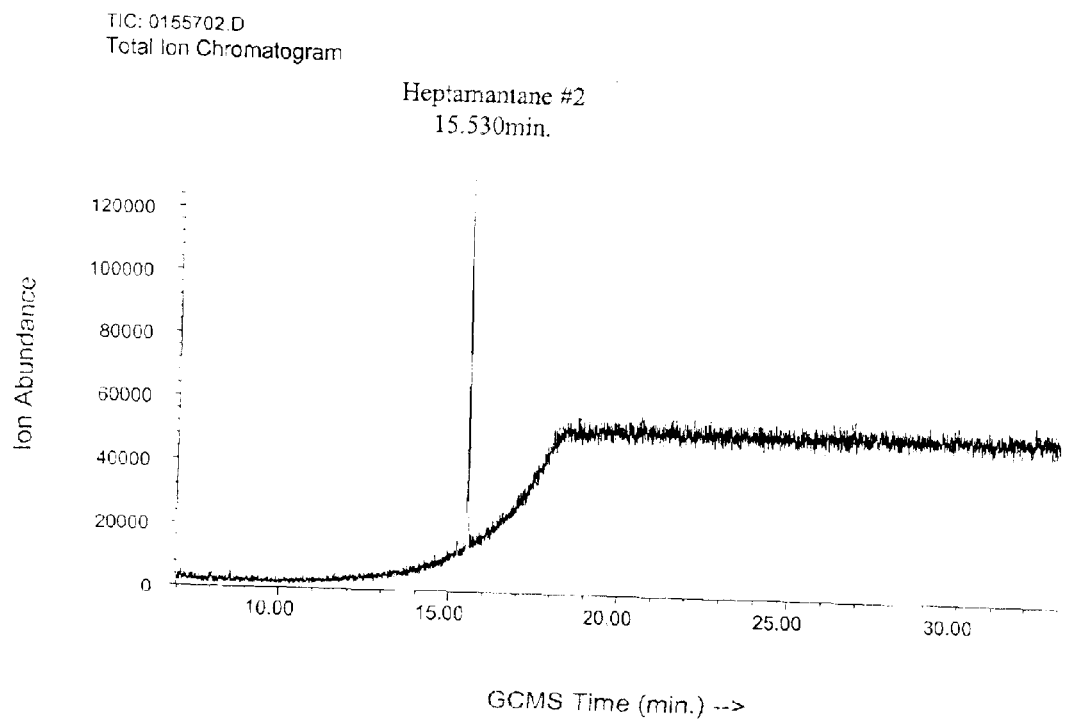
B)
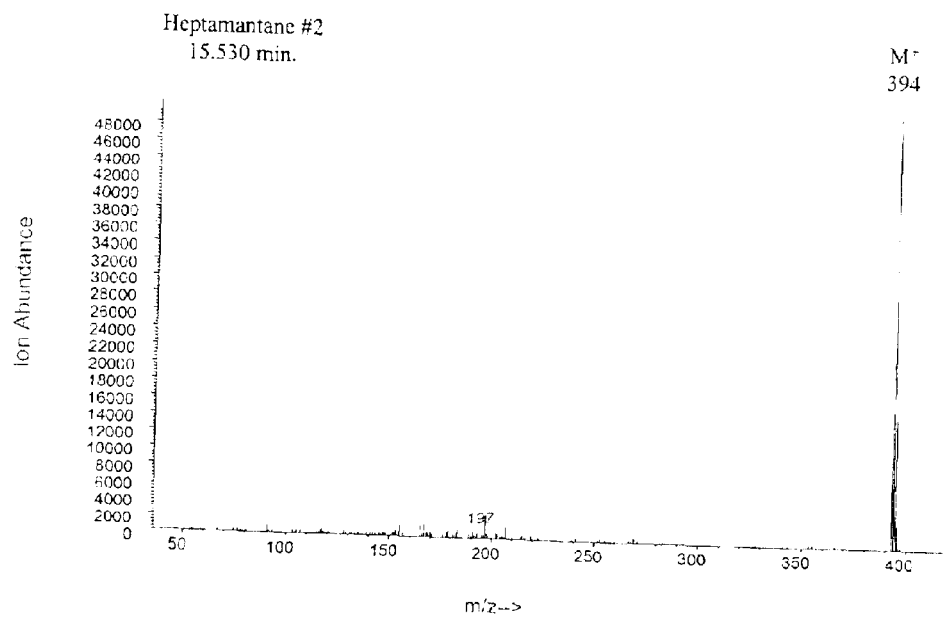

FIG. 23
A)
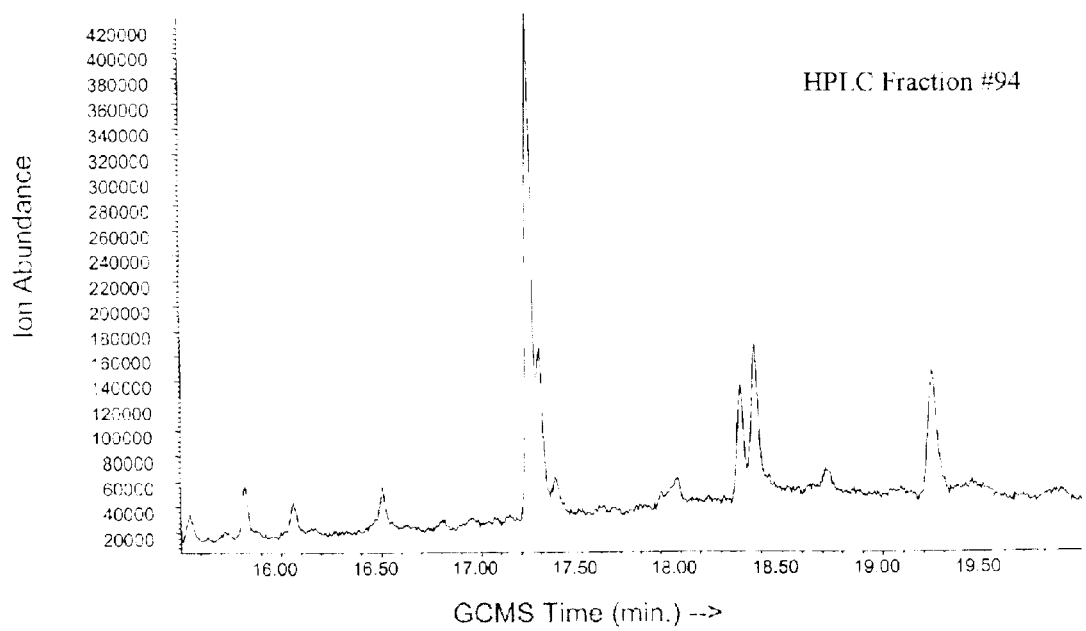
B)
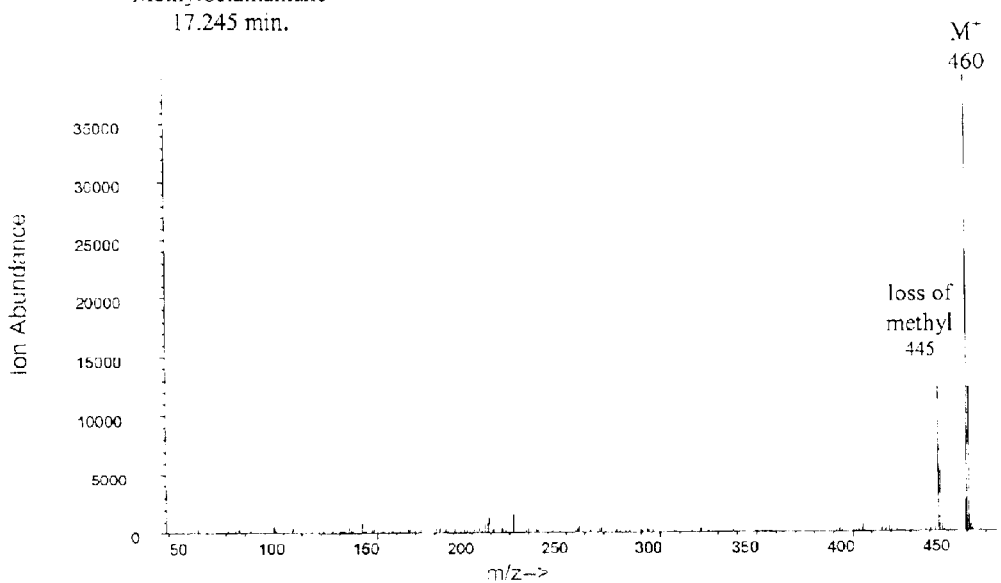

FIG. 24
[12342 31] Octamantane
enantiomer A
Formula: $C_{34}H_{38}$
Symmetry: $C_2$
Molecular Weight 446.678
Molecular Weight (Exact) 446.2973514
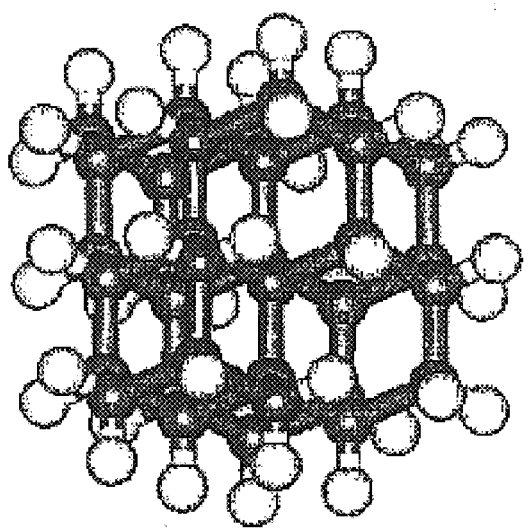
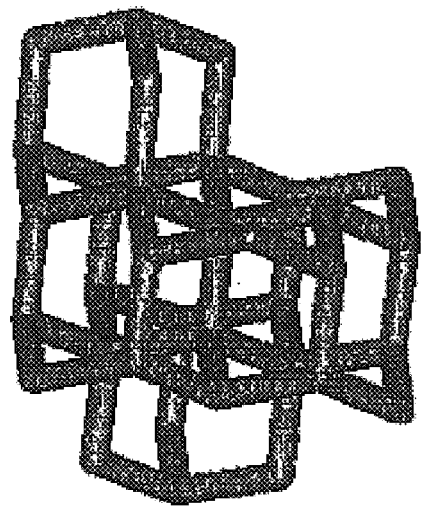
Carbon Framework
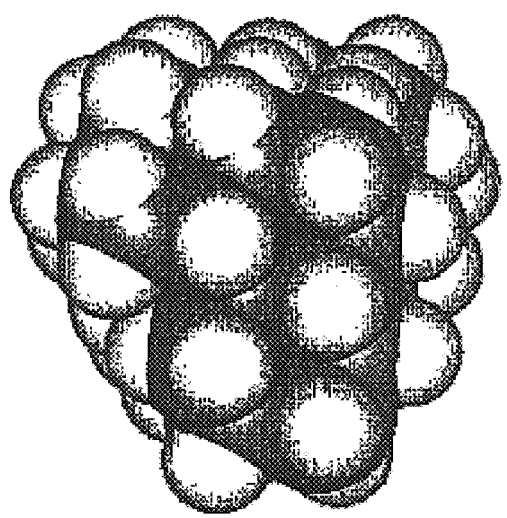
CPK Representation

[1234231] Octamantane
enantiomer A
View into Specified Diamond Crystal Lattice Plane 111 110 100

FIG. 26 Octamantane
enantiomer B
Formula: $C_{34}H_{38}$
Symmetry: $C_2$
Molecular Weight 446.678
Molecular Weight (Exact) 446.2973514
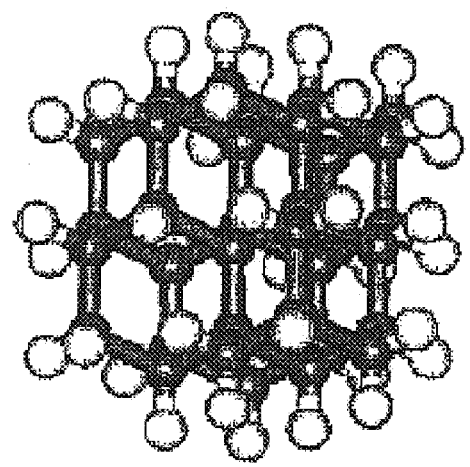
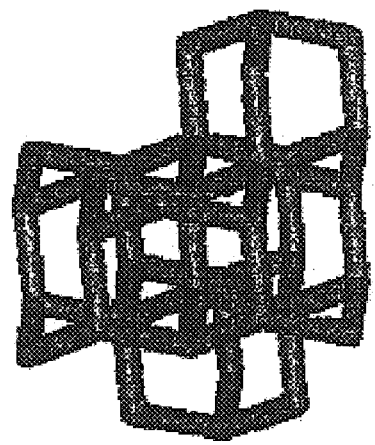
Carbon Framework
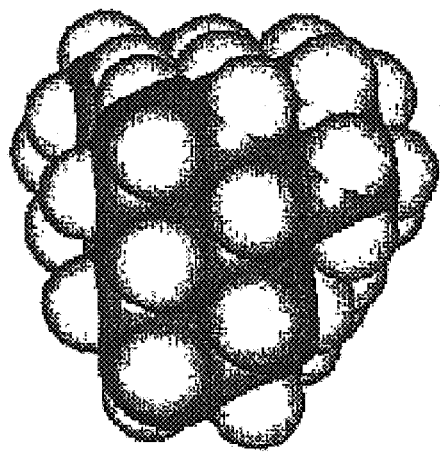
CPK Representation FIG. 27 Octamantane
enantiomer B
View into Specified Diamond Crystal Lattice Plane
| 111 | 110 | 100 |
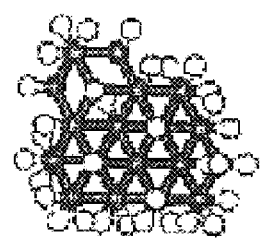 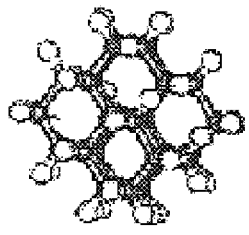 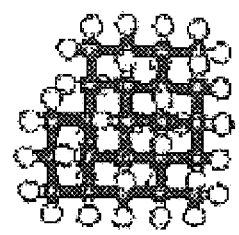
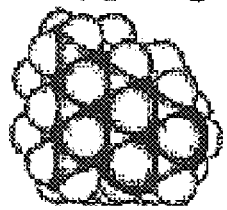 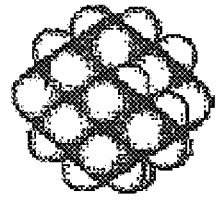 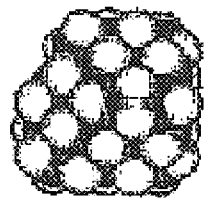
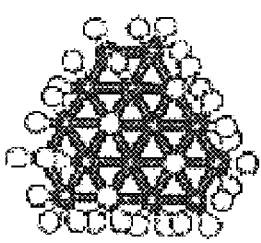 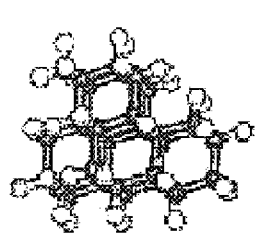 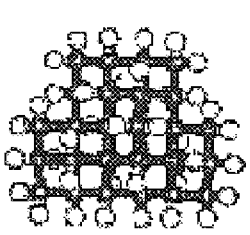
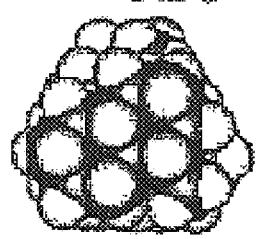 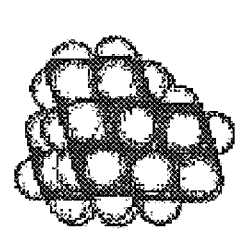 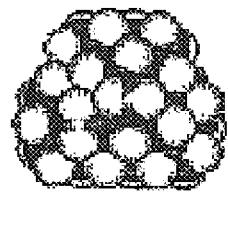
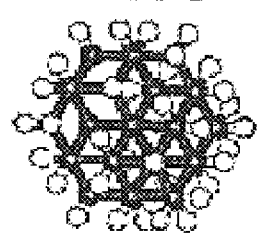 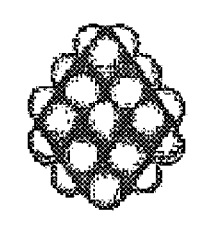
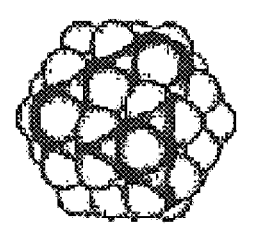 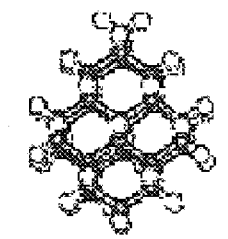

FIG. 28 Octamantane
enantiomer A
Formula: $C_{34}H_{38}$
Symmetry: $C_1$
Molecular Weight 446.678
Molecular Weight (Exact) 446.2973514
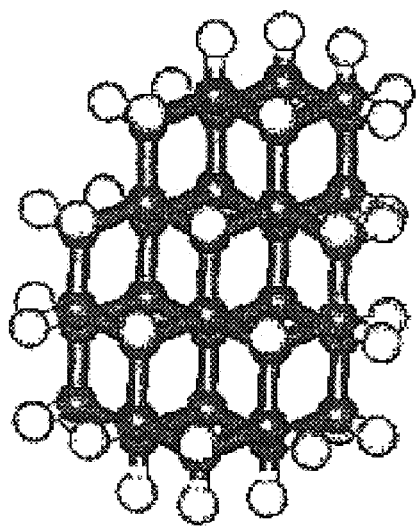
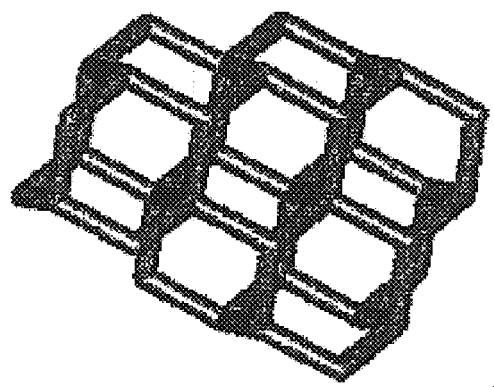
Carbon Framework
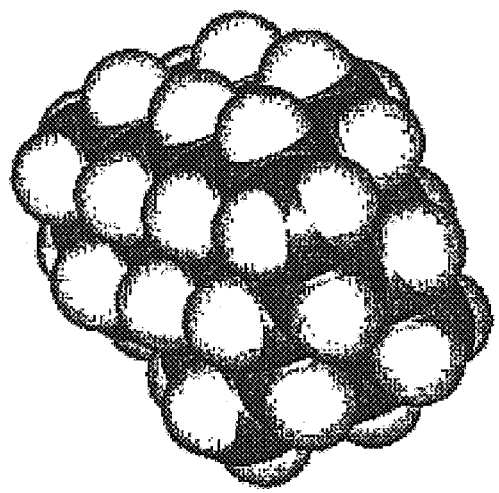
CPK Representation

[1212312] Octamantane
enantiomer A
View into Specified Diamond Crystal Lattice Plane

FIG. 30
[12|2312] Octamantane
enantiomer B
Formula: $C_{34}H_{38}$
Symmetry: $C_1$
Molecular Weight: 446.678
Molecular Weight (Exact): 446.2973514
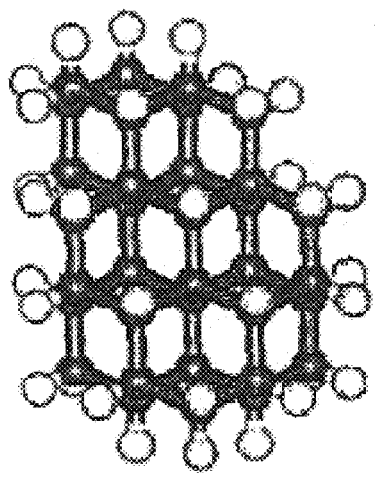
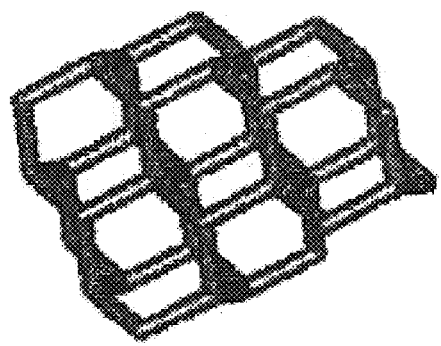
Carbon Framework
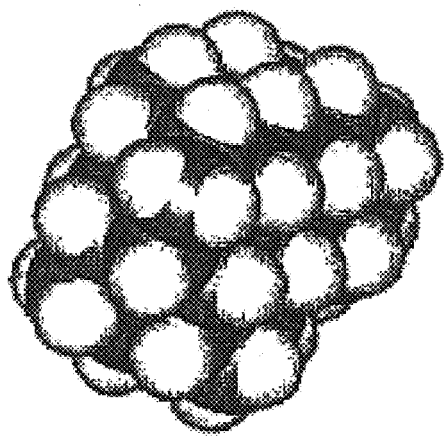
CPK Representation

[1212312] Octamantane
enantiomer B
View into Specified Diamond Crystal Lattice Plane 111　　　　　110　　　　　100

FIG. 32 Octamantane
enantiomer A
Formula: $C_{34}H_{38}$
Symmetry: $C_2$
Molecular Weight: 446.678
Molecular Weight (Exact): 446.2973514
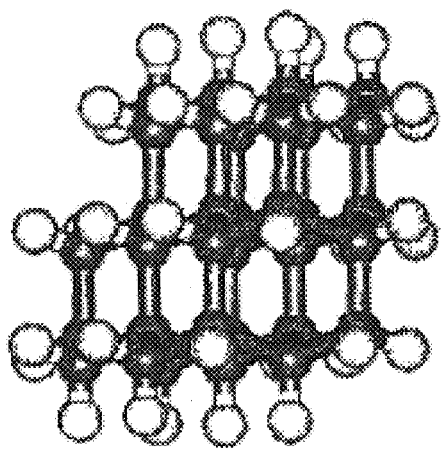
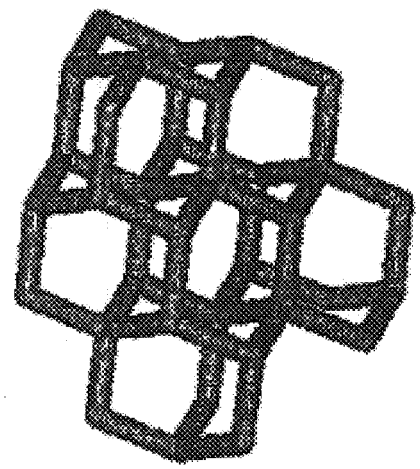
Carbon Framework
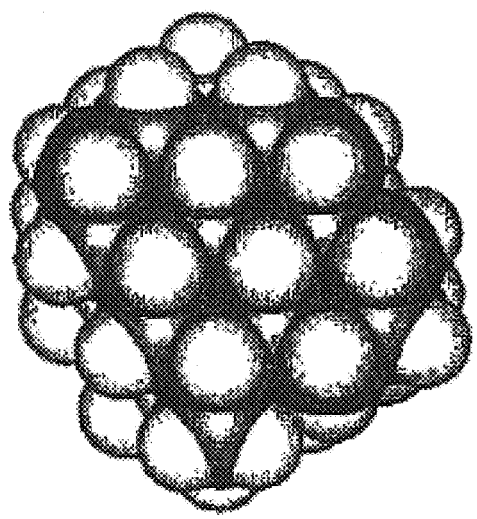
CPK Representation

[1213212] Octamantane
enantiomer A
View into Specified Diamond Crystal Lattice Plane FIG. 34 Octamantane
enantiomer B
Formula: $C_{34}H_{38}$
Symmetry: $C_2$
Molecular Weight 446.678
Molecular Weight (Exact) 446.2973514
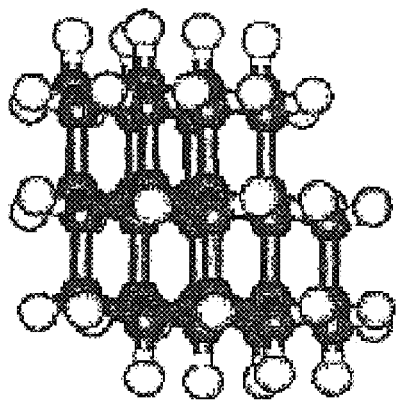
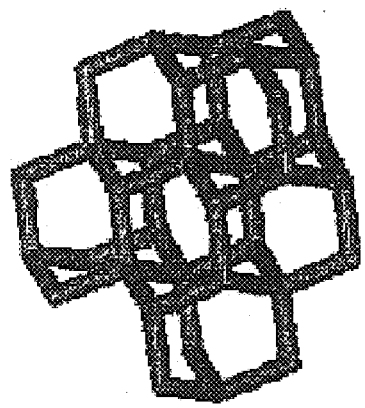
Carbon
Framework
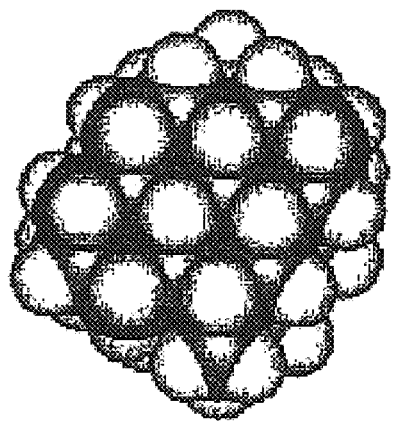
CPK
Representation

FIG. 35
[1213212] Octamantane
enantiomer B
View into Specified Diamond Crystal Lattice Plane
| 111 | 110 | 100 |
|---|---|---|
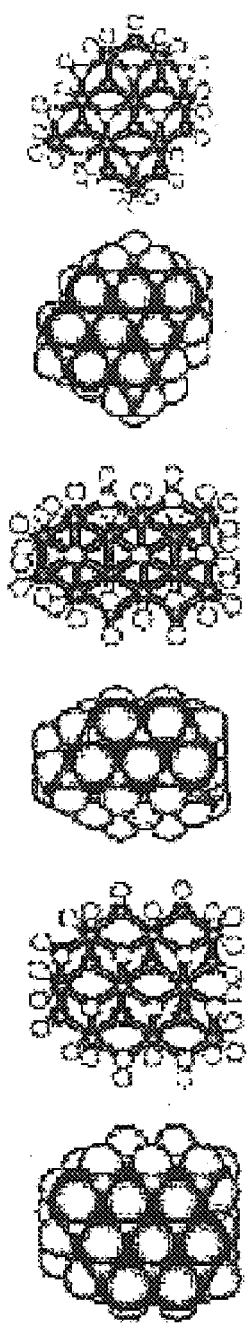
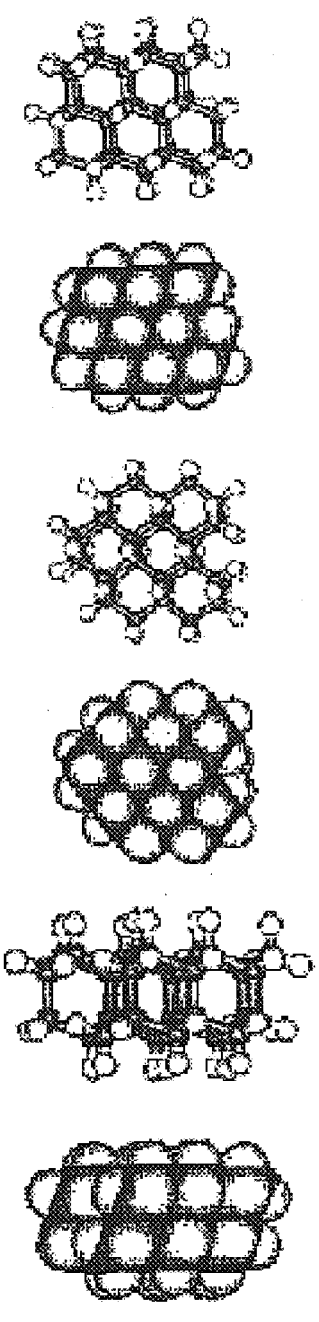
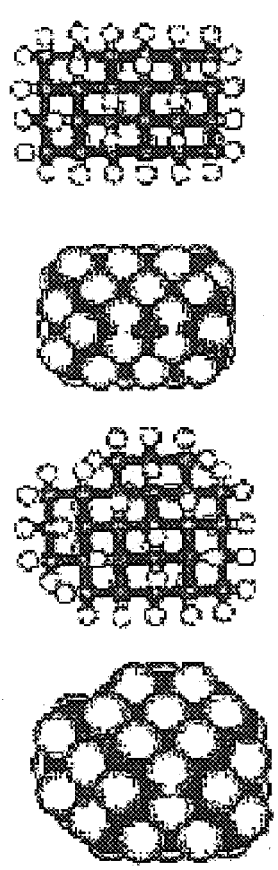

FIG. 36
[1213(1)21] Octamantane
Formula: $C_{34}H_{38}$
Symmetry: $C_{2h}$
Molecular Weight: 446.678
Molecular Weight (Exact): 446.2973514
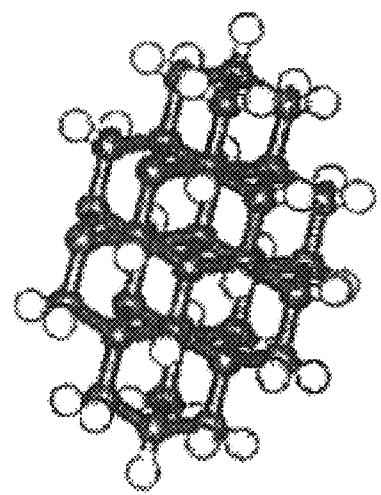
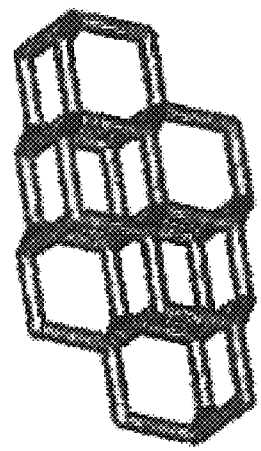
Carbon Framework
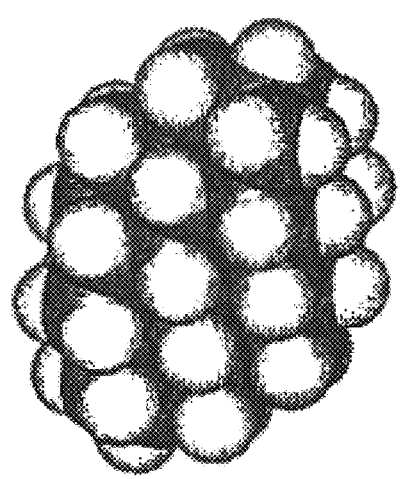
CPK Representation

[1213(1)21] Octamantane
View into Specified Diamond Crystal Lattice Plane

FIG. 38
[123(2,4)12] Octamantane
Formula: $C_{34}H_{38}$
Symmetry: $C_s$
Molecular Weight: 446.678
Molecular Weight (Exact): 446.2973514
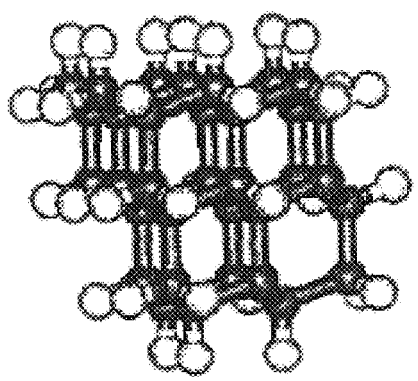
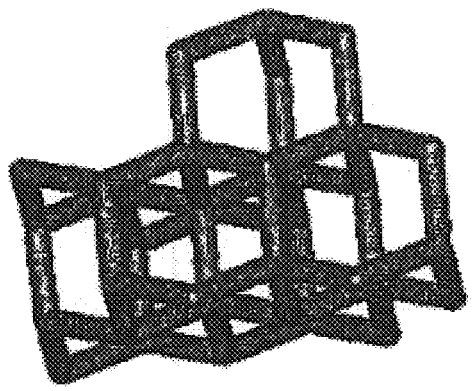
Carbon Framework
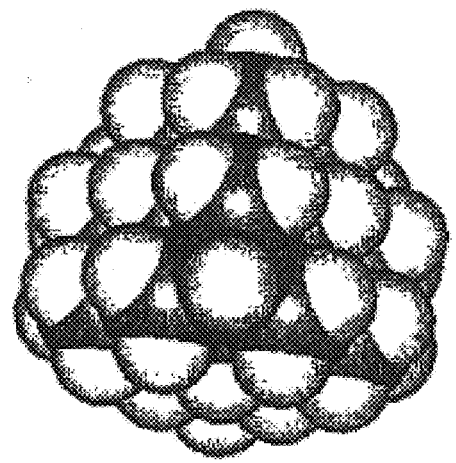
CPK Representation

[123(2,4)12] Octamantane
View into Specified Diamond Crystal Lattice Plane 111 110 100

FIG. 40 Octamantane
enantiomer A
Formula: $C_{34}H_{38}$
Symmetry: $C_1$
Molecular Weight 446.678
Molecular Weight (Exact) 446.2973514
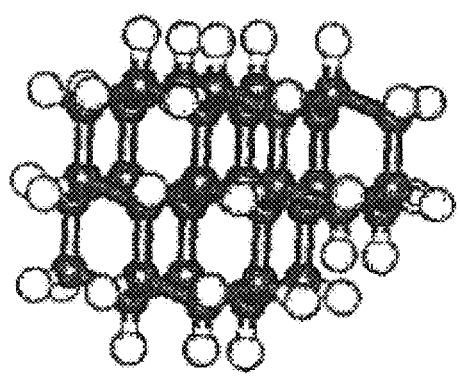
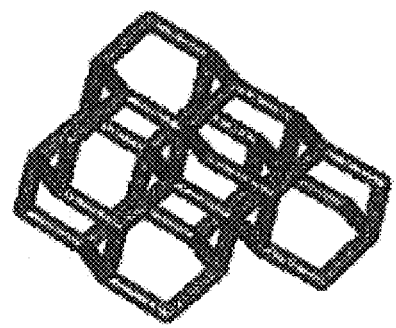
Carbon Framework
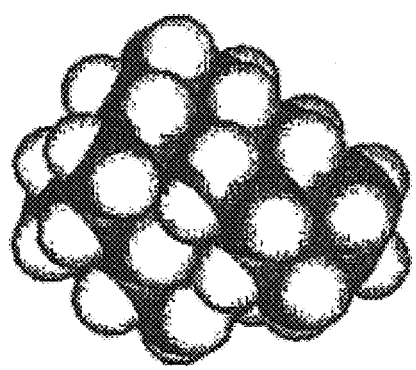
CPK Representation

[1213413] Octamantane 7
enantiomer A
View into Specified Diamond Crystal Lattice Plane 111  110  100

FIG. 42 Octamantane
enantiomer B
Formula: $C_{34}H_{38}$
Symmetry: $C_1$
Molecular Weight: 446.678
Molecular Weight (Exact): 446.2973514
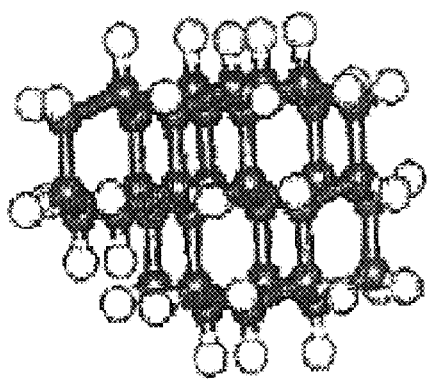
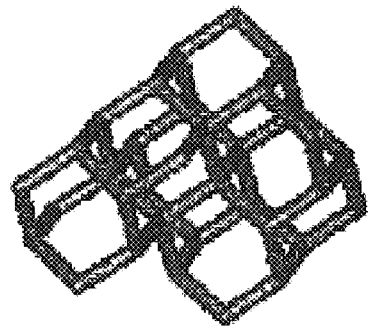
Carbon Framework
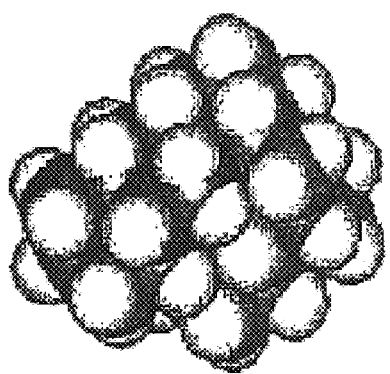
CPK Representation

[1213413] Octamantane
enantiomer B
View into Specified Diamond Crystal Lattice Plane 111        110        100

[1213214] Octamantane
enantiomer A
Formula: $C_{34}H_{38}$
Symmetry: $C_1$
Molecular Weight: 446.678
Molecular Weight (Exact): 446.2973514
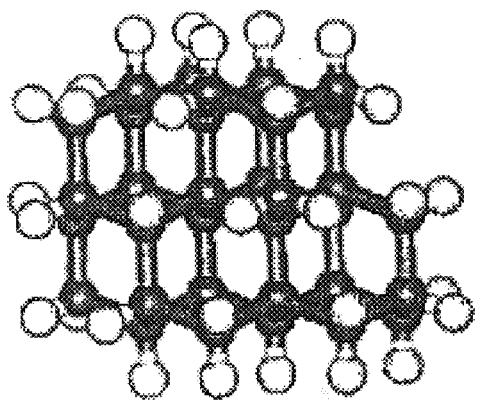
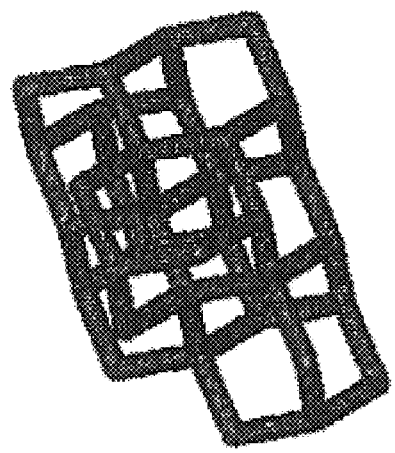
Carbon Framework
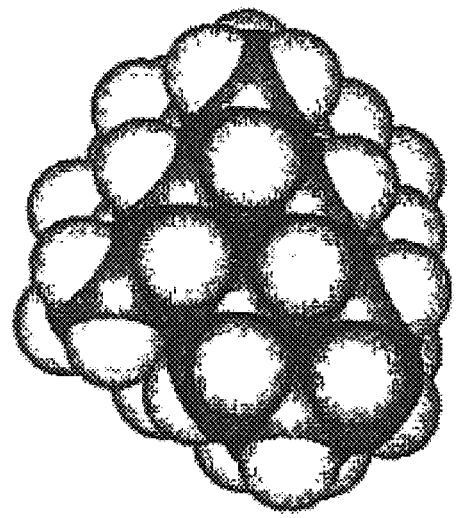
CPK Representation

[1213214] Octamantane
enantiomer A
View into Specified Diamond Crystal Lattice Plane FIG. 46 Octamantane
enantiomer B
Formula: $C_{34}H_{38}$
Symmetry: $C_1$
Molecular Weight: 446.678
Molecular Weight (Exact): 446.2973514
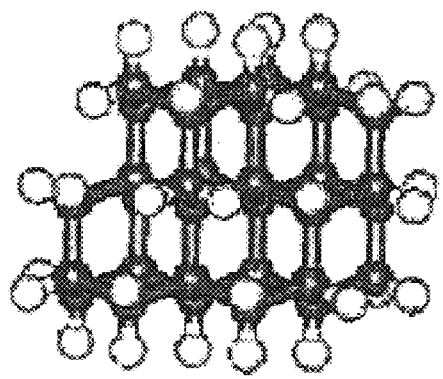
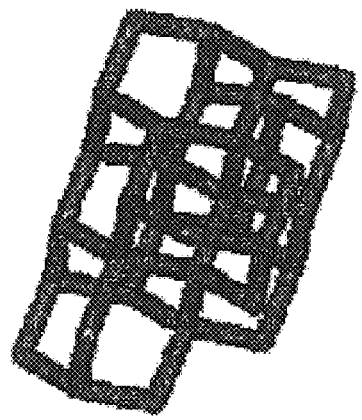
Carbon Framework
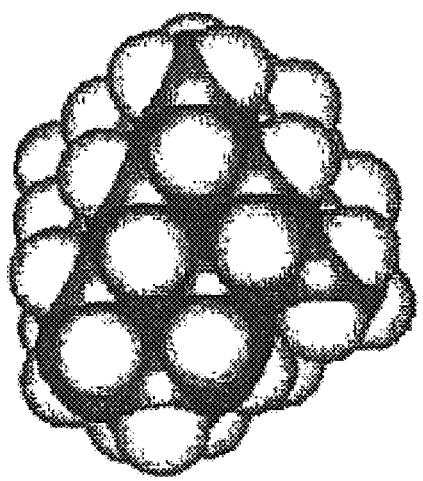
CPK Representation

[1213214] Octamantane
enantiomer B
View into Specified Diamond Crystal Lattice Plane 111 110 100

FIG. 48
[1232432] Octamantane
Formula: $C_{34}H_{38}$
Symmetry: $C_s$
Molecular Weight: 446.678
Molecular Weight (Exact): 446.2973514
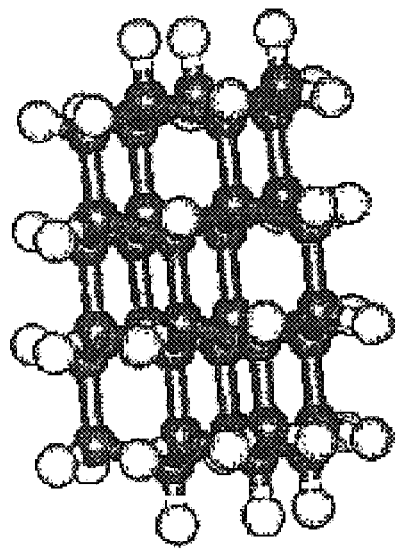
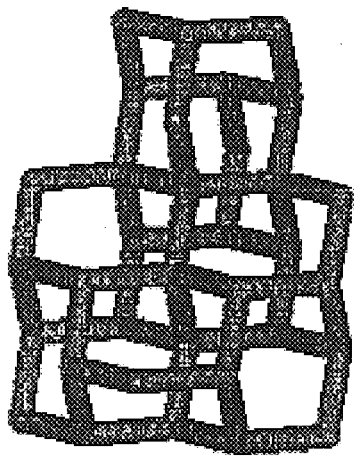
Carbon Framework
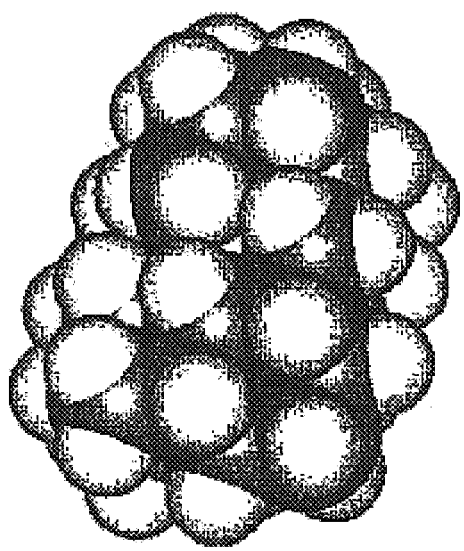
CPK Representation

[1232432] Octamantane
View into Specified Diamond Crystal Lattice Plane

FIG. 50
[1213(4)21] Octamantane
Formula: $C_{34}H_{38}$
Symmetry: $C_s$
Molecular Weight 446.678
Molecular Weight (Exact) 446.2973514
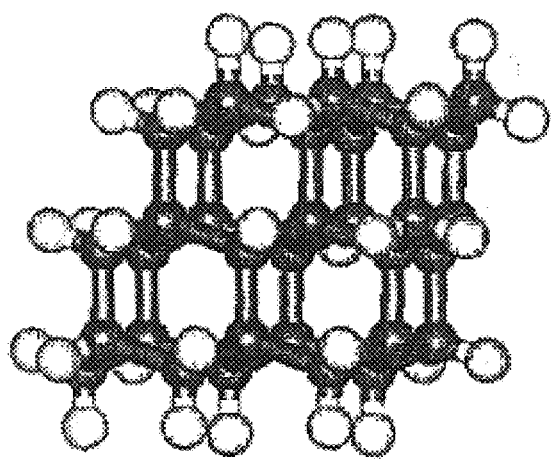
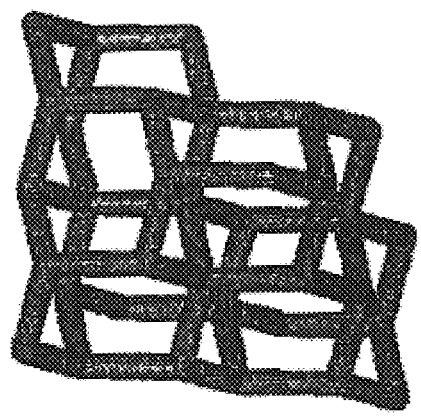
Carbon Framework
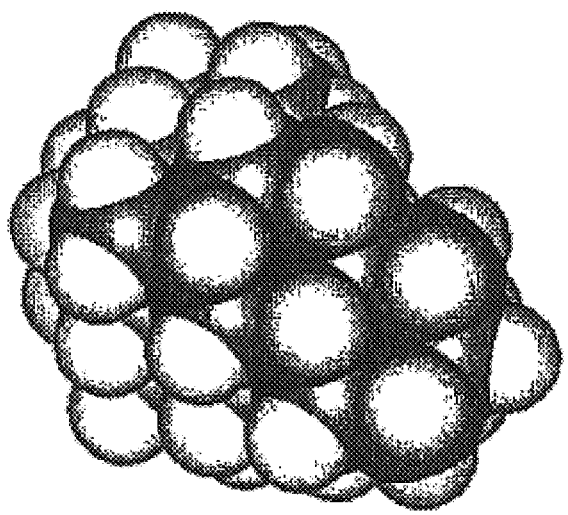
CPK Representation

[1213(4)21] Octamantane
View into Specified Diamond Crystal Lattice Plane

FIG. 52
[1234(1)23] Octamantane
Formula: $C_{34}H_{38}$
Symmetry: $C_{2h}$
Molecular Weight 446.678
Molecular Weight (Exact) 446.2973514
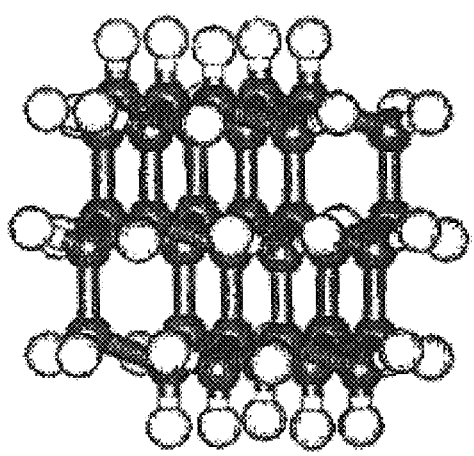
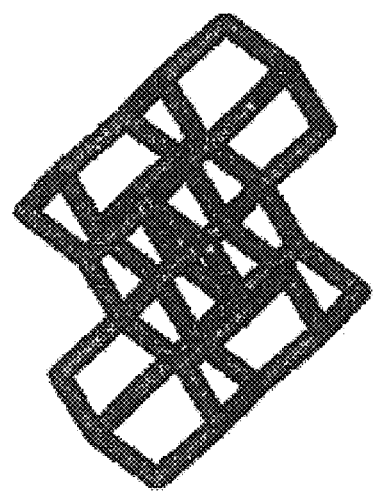
Carbon Framework
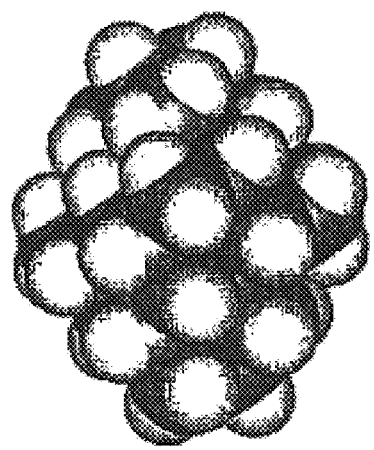
CPK Representation

[1234(1)23] Octamantane
View into Specified Diamond Crystal Lattice Plane 111　　　　　　　110　　　　　　　100

FIG. 54
[12132(1)4] Octamantane
enantiomer A
Formula: $C_{34}H_{38}$
Symmetry: $C_1$
Molecular Weight 446.678
Molecular Weight (Exact) 446.2973514
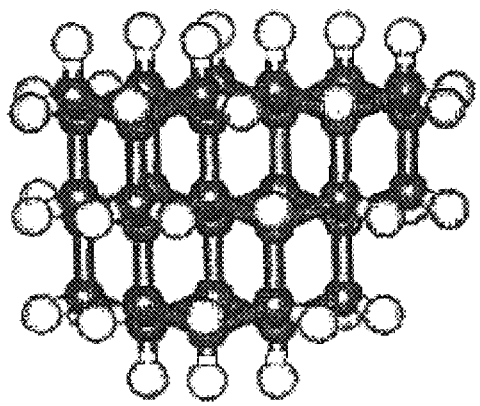
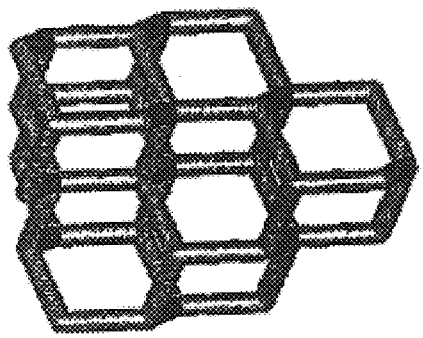
Carbon Framework
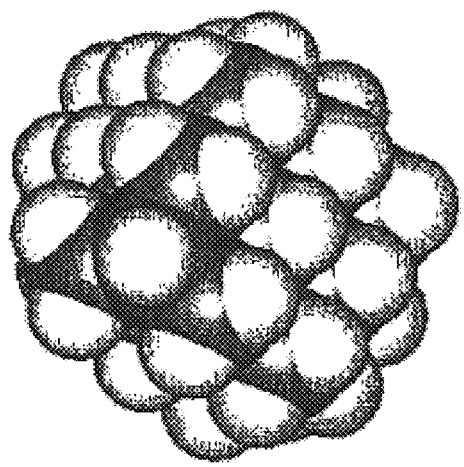
CPK Representation

[12132(1)4] Octamantane
enantiomer A
View into Specified Diamond Crystal Lattice Plane FIG. 56
[12132(1)4] Octamantane
enantiomer B
Formula: $C_{34}H_{38}$
Symmetry: $C_1$
Molecular Weight 446.678
Molecular Weight (Exact) 446.2973514
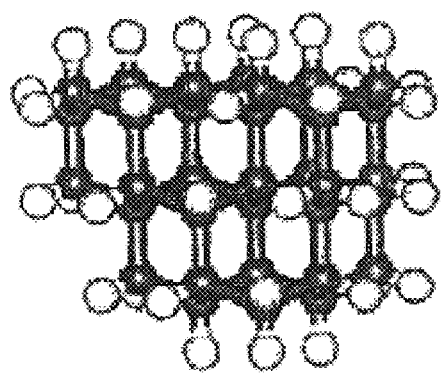
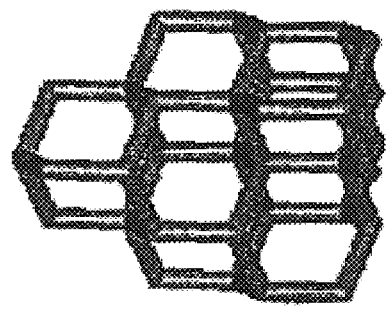
Carbon
Framework
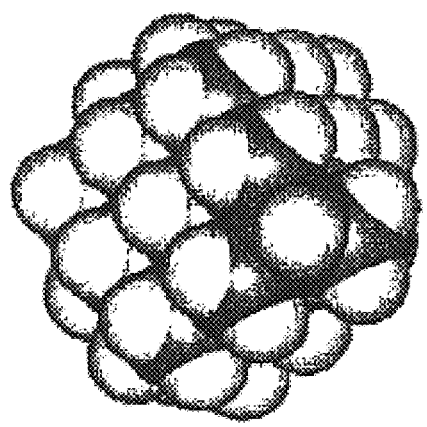
CPK
Representation

[12132(1)4] Octamantane
enantiomer B
View into Specified Diamond Crystal Lattice Plane FIG. 58
[12132(1)3] Octamantane
Formula: $C_{34}H_{38}$
Symmetry: $C_s$
Molecular Weight 446.678
Molecular Weight (Exact) 446.2973514
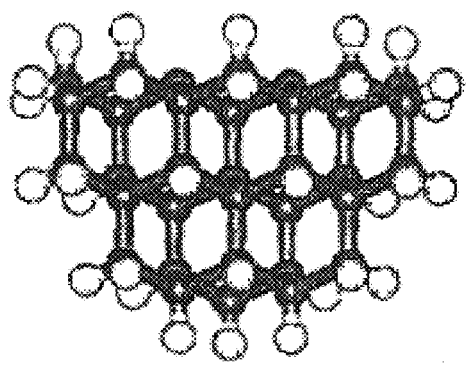
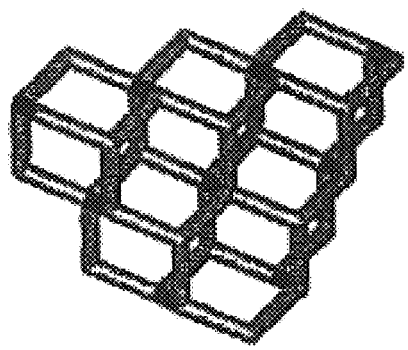
Carbon Framework
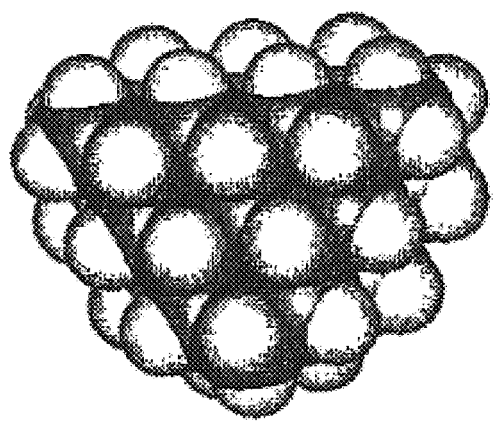
CPK Representation

[12132(1)3] Octamantane
View into Specified Diamond Crystal Lattice Plane

FIG. 60
[12342(1)3] Octamantane
Formula: $C_{33}H_{36}$
Symmetry: $D_{2d}$
Molecular Weight: 432.651
Molecular Weight (Exact): 432.2817013
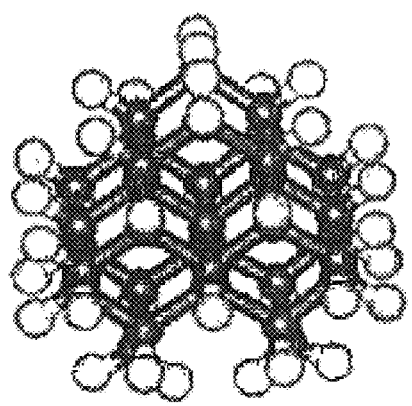
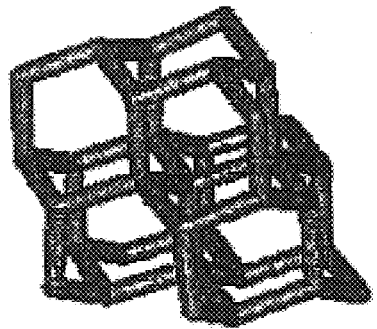
Carbon Framework
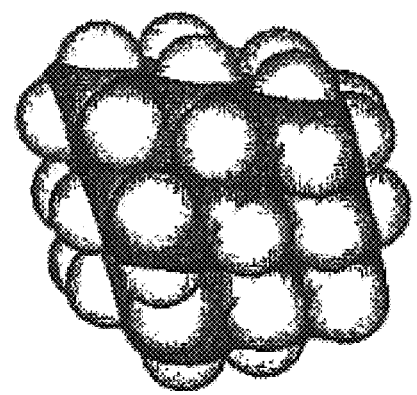
CPK Representation

[12342(1)3]] Octamantane
View into Specified Diamond Crystal Lattice Plane

[1232142] Octamantane
Formula: $C_{36}H_{40}$
Symmetry:
Molecular Weight: 472.716
Molecular Weight (Exact): 472.3130015
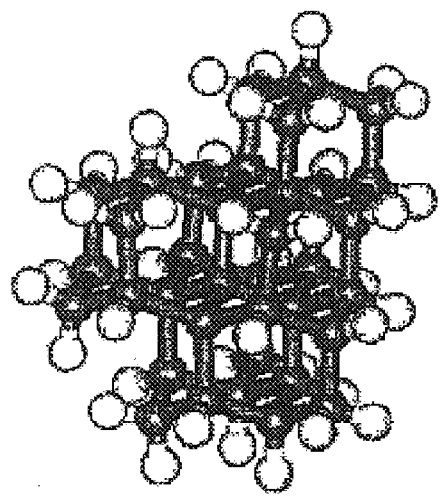
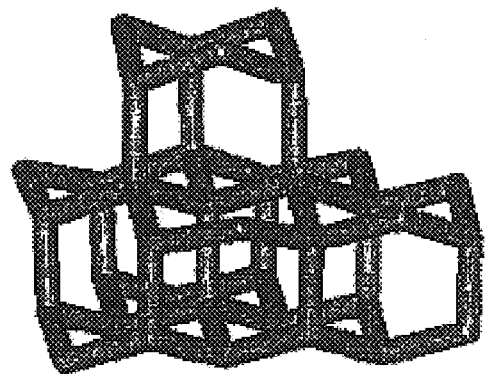
Carbon Framework
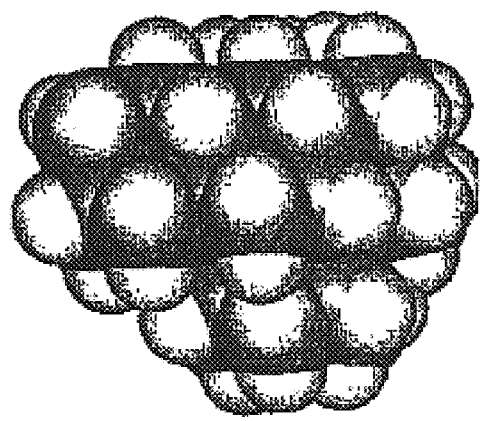
CPK Representation

[1232142] Octamantane
View into Specified Diamond Crystal Lattice Plane 111  110  100

FIG. 64
[1(2)3(4)1(2)3] Octamantane
Formula: $C_{37}H_{42}$
Symmetry: $C_S$
Molecular Weight 486.783
Molecular Weight (Exact) 486.3286516
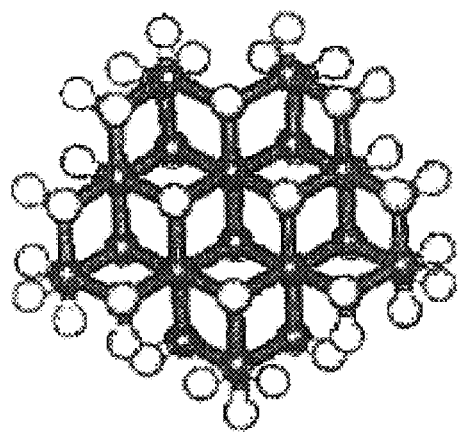
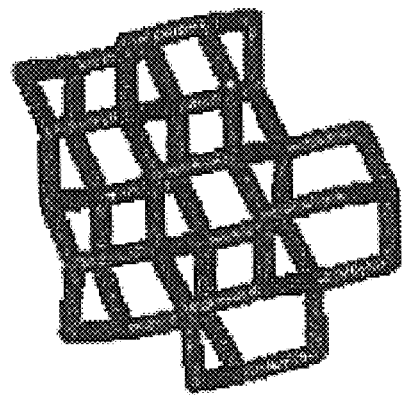
Carbon Framework
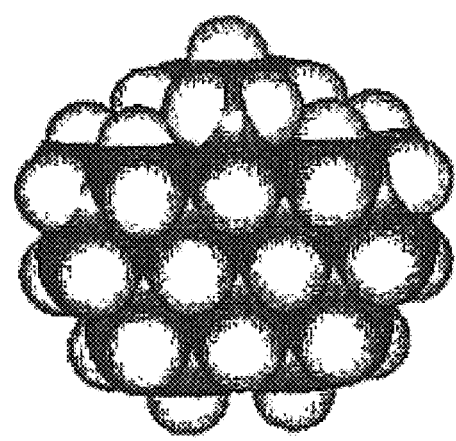
CPK Representation FIG. 65
[1(2)3(4)1(2)3] Octamantane
View into Specified Diamond Crystal Lattice Plane
111            110            100
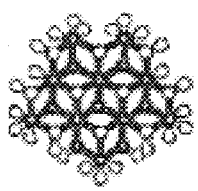 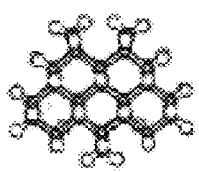 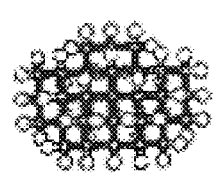
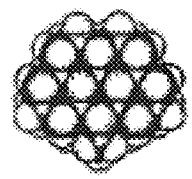 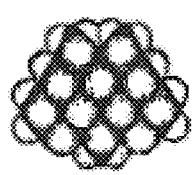 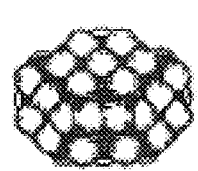

[1212121] Octamantane

Formula: $C_{38}H_{44}$
Symmetry: $C_{2h}$
Molecular Weight  500.770
Molecular Weight (Exact)  500.3443016

Carbon Framework

FIG.67 Octamantane
View into Specified Diamond Crystal Lattice Plane
111 110 100
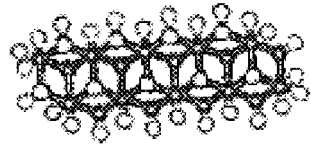 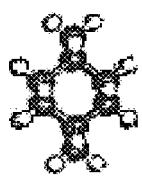 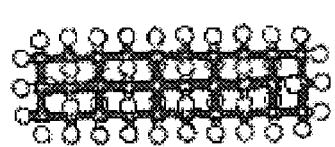
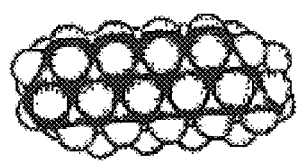 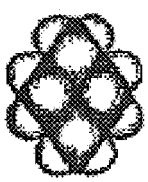 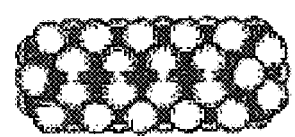

COMPOSITIONS COMPRISING OCTAMANTANES AND PROCESSES FOR THEIR SEPARATION

REFERENCE TO RELATED APPLICATIONS

This application claims priority under 35 U.S.C. §119(e) to U.S. Provisional Application Ser. No. 60/262,842, filed Jan. 19, 2001 and to U.S. Provisional Application Ser. No. 60/323,883, filed Sep. 20, 2001, both of which are incorporated by reference.

BACKGROUND OF THE INVENTION

1. Field of the Invention

This invention is directed to novel compositions comprising one or more octamantanes. This invention is also directed to novel processes for the separation and isolation of octamantane components into recoverable fractions from a feedstock containing one or more octamantane components.

REFERENCES

The following publications and patents are cited in this application as superscript numbers:

[1] Lin, et al., Natural Occurrence of Tetramantane ($C_{22}H_{28}$), Pentamantane ($C_{26}H_{32}$) and Hexamantane ($C_{30}H_{36}$) in a Deep Petroleum Reservoir, Fuel, 74(10):1512–1521 (1995)

[2] Alexander, et al., Purification of Hydrocarbonaceous Fractions, U.S. Pat. No. 4,952,748, issued Aug. 28, 1990

[3] McKervey, Synthetic Approaches to Large Diamondoid Hydrocarbons, Tetrahedron, 36:971–992 (1980).

[4] Wu, et al., High Viscosity Index Lubricant Fluid, U.S. Pat. No. 5,306,851, issued Apr. 26, 1994.

[5] Chung et al., Recent Development in High-Energy Density Liquid Fuels, Energy and Fuels, 13, 641–649 (1999).

[6] Sandia National Laboratories (2000), World's First Diamond Micromachines Created at Sandia, Press Release, (Feb. 22, 2000) www.Sandia.gov.

[7] Balaban et al., Systematic Classification and Nomenclature of Diamondoid Hydrocarbons-I, Tetrahedron. 34, 3599–3606 (1978).

[8] Chen, et al., Isolation of High Purity Diamondoid Fractions and Components, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

2. State of the Art

Octamantanes are bridged-ring cycloalkanes. They are the face-fused octamers of adamantane (tricyclo[3.3.1.1$^{3,7}$] decane) or $C_{10}H_{16}$. The compounds have a "diamondoid" topology, which means their carbon atom arrangement is superimposable on a fragment of the diamond lattice (FIG. 1). Octamantanes possess eight of the "diamond crystal units" and therefore, it is postulated that there are hundreds of possible octamantane structures which exist in different molecular weight core structures. Among them, 18 have the molecular formula $C_{34}H_{38}$ (molecular weight 446). Octamantanes also have the molecular formulas: $C_{38}H_{44}$ (molecular weight 500), $C_{37}H_{42}$ (molecular weight 486), $C_{36}H_{40}$ (molecular weight 472) and $C_{33}H_{36}$ (molecular weight 432).

Little or no published work is available for octamantanes and higher molecular weight diamondoids. Octamantane compounds have not been artificially synthesized or isolated and these higher diamondoids along with hexamantane and heptamantane compounds have been recently thought only to have a theoretical existence.[7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding practical applications of higher diamondoids and even less, if any information regarding octamantanes. This fact is probably due to extreme difficulties encountered in their isolation and due to failed synthesis attempts. Lin and Wilk, for example, discuss the possible presence of pentamantanes in a gas condensate and further postulate that hexamantane may also be present.[1] The researchers postulate the existence of these compounds contained within petroleum solely based on a mass spectrometric selected ion monitoring (SIM) and mass spectral fragmentation patterns. They did not, however, report the isolation of a single pentamantane, hexamantane nor mention heptamantane or octamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement routes employing Lewis acid catalysts, useful in synthesizing triamantane and lower diamondoids have been unsuccessful in synthesizing other tetramantanes or pentamantanes. No attempt to synthesize or isolate octamantanes has been reported.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

In addition, based on theoretical considerations, the octamantanes have sizes in the nanometer range and, in view of the properties noted above, the inventors contemplate that such compounds would have utility in micro- and molecular-electronics and nanotechnology applications. In particular, the rigidity, strength, stability, variety of structural forms and multiple attachment sites shown by these molecules makes possible accurate construction of robust, durable, precision devices with nanometer dimensions. The various octamantanes are three-dimensional nanometer sized units showing different diamond lattice arrangements. This translates into a variety of rigid shapes and sizes for the octamantane components. For example, [1212121] octamantane is rod shaped, [1234(1)23]octamantane is "S"- shaped, while [12132(1)3] is a wedge-shaped structure. A variety of other shapes exist among the octamantanes which may serve in applications which depend upon specific geometries. It has been estimated that MicroElectroMechanical Systems (MEMs) constructed out of diamond should last 10,000 times longer then current polysilicon MEMs, and diamond is chemically benign and would not promote allergic reactions in biomedical applications.[6] Again, the inventors contemplate that the various octamantanes would have similar attractive properties. Furthermore, most of the octamantanes would possess chirality, offering opportunities for making nanotechnology objects of great structural specificity and ones which have useful optical properties. FIG. 2 illustrates examples of symmetric and asymmetric octamantane structures. Applications of these octamantanes include molecular electronics, photonics and production of nanomechanical devices, and other materials.

Notwithstanding these advantages of octamantanes, the art, as noted above, fails to provide for compositions comprising octamantanes or for processes that would lead to these compositions. In view of the above, there is an ongoing need in the art to provide for compositions comprising one or more octamantanes.

SUMMARY OF THE INVENTION

This invention is directed to novel compositions comprising one or more octamantanes and/or octamantane components.

Accordingly, in one of its composition aspects, this invention is directed to a composition comprising one or more octamantane components wherein said composition comprises at least about 25 weight percent octamantane components based on the total weight of the diamondoids in the composition.

In another of its composition aspects, the compositions preferably comprise one or more octamantane components wherein the octamantane components make up from about 50 to 100 weight percent, preferably about 70 to 100 weight percent, more preferably about 90 to 100 weight percent and even more preferably about 95 to 100 weight percent of the total weight of the diamondoids in the compositions.

In another of its composition aspects, the compositions comprise at least about 10 weight percent and preferably at least about 20 weight percent of octamantanes based on the total weight of the composition. Other compositions of this invention contain from 50 to 100 weight percent, 70 to 100 weight percent, 95 to 100 weight percent and 99 to 100 weight percent of octamantanes based on the total weight of the composition.

In another of its composition aspects, the compositions preferably comprise from about 70 to 100 weight percent, more preferably from about 90 to 100 weight percent, even more preferably from about 95 to 100 weight percent and most preferably from about 99 to 100 weight percent of a single octamantane component, including isolated optical isomers thereof, based on the total weight of the composition Compositions are sufficiently enriched in octamantane components the octamantanes can form crystal structures. Accordingly, another aspect of this invention is directed to a composition comprising an octamantane crystal. Since such octamantane can co-crystallize, another aspect of this invention is directed to the co-crystals comprising crystals of at least two octamantane components or an octamantane component and another higher diamondoid component.

This invention is also directed to novel processes for the separation and isolation of octamantane components into recoverable fractions from a feedstock containing one or more octatnantane components and nonoctamantane materials. These processes for recovering a composition enriched in octamantane components entail removing at least a portion of the nonoctamantane materials which have a boiling point below the lowest boiling octamantane component and utilizing a subsequent separation technique to recover octamantane components from the resulting residue. Accordingly, this aspect is directed to processes which comprise:

a) selecting a feedstock comprising recoverable amounts of octamantane components and nonoctamantane materials;

b) removing from the feedstock a sufficient amount of nonoctamantane materials that have boiling points below the boiling point of the lowest boiling point octamantane component in the feedstock under conditions to form a treated feedstock enriched in octamantane components which can be recovered;

c) recovering octamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the treated feedstock can be thermally treated to pyrolyze at least a sufficient amount of nondiamondoid components therefrom under conditions to provide a thermally treated feedstock retaining recoverable amounts of octamantane. Such a pyrolization step prior to step c) is useful for thermally degrading at least a portion of any materials remaining in the treated feedstock having a thermal stability lower than the octamantane components. This pyrolysis step can be carried out before step b) if desired.

In a preferred embodiment of this invention, directed to the chromatographic techniques, is employing high performance liquid chromatography using one or more columns, more preferably reverse phase. A more preferred method, is using columns exhibiting a different selectivity to the octamantane components slated for enrichment. Alternatively, high performance liquid chromatography can be coupled with gas chromatography, such as preparative gas chromatography to further facilitate isolations.

BRIEF DESCRIPTION OF THE DRAWINGS

FIG. 1 illustrates the correlation of the structures of diamondoids to subunits of the diamond crystal lattice.

FIG. 2 illustrates the carbon framework example of a symmetrical and an enantiomeric octamantane.

FIGS. 9(A, B) illustrates the GC/MS total ion chromatogram and mass spectrum of octamantane #1 highly concentrated by high performance liquid chromatography.

FIG. 11 illustrates results of a preparative HPLC separation of Feedstock B distillate cut #7 pyrolysis product saturated hydrocarbon fraction showing HPLC fractions taken using octadecyl silane "ODS" columns and acetone mobile phase. Octamantanes are numbered in order of their elution order on our GC/MS assay, and typical GC/MS retention times are listed.

FIGS. 12(A, B) illustrates the gas chromatograms of the concentration of octamantanes using pyrolysis. FIG. 12B illustrates the GC of Feedstock B atmospheric distillation fraction #7, which was used as feedstock in pyrolytic processing. FIG. 12A illustrates the GC of the product of the pyrolytic process.

FIGS. 14(A, B) illustrates photomicrographs of co-crystalline octamantane #3 and #5, crystal B was dissolved in cyclohexane and analyzed by GC/MS (FIG. 13).

FIGS. 15(A, B) illustrates GC/MS total ion chromato gram (TIC) and mass spectrum of octamantane #1 and octamantane #10 containing ODS HPLC fraction #80 (FIG. 11).

FIGS. 16(A, B) illustrates GC/MS total ion chromatogram (TIC) and mass spectrum of an octamantane (molecular weight 500) containing ODS HPLC fraction #92 (FIG. 11).

FIGS. 17(A, B) illustrates the preparative capillary gas chromatographic data for heptamantane isolations. FIG. 17A, shows the first column cuts containing two of the heptamantanes from Feedstock B. FIG. 17B, shows the second column peaks isolated and sent to the traps. From this procedure pure heptamantanes were isolated (FIGS. 18–21), heptamantane #1, the first heptamantane to elute in our GC/MS assay, and heptamantane #2 which is the second to elute. This same methodology can be used to separate octamantanes using HPLC fractions (e.g. FIGS. 13, 15 and 16) as a starting material.

FIGS. 18(A, B) illustrates the GC/MS total ion chromatogram and mass spectrum of heptamantane #1 isolated by preparative capillary gas chromatography.

FIGS. 19(A, B) illustrates the GC/MS total ion chromatogram and mass spectrum of heptamantane #2 isolated by preparative capillary gas chromatography.

FIG. 20 illustrates a photomicrograph of heptamantane #1 crystals isolated from Feedstock B by preparative capillary gas chromatography.

FIGS. 22(A, B) illustrates GC/MS total ion chromatogram (TIC) and mass spectrum of heptamantane #2 isolated using two different HPLC columns.

FIGS. 23(A, B) illustrates GC/MS total ion chromatogram (TIC) and mass spectrum of a methyloctamantane (mol. wt. 460) isolated in ODS HPLC fraction #94.

FIGS. 24 through 59 illustrate the structures with views into various diamond crystal lattice planes for each of the eighteen, molecular formula $C_{34}H_{38}$ (molecular weight 446) octamantane structures.

FIGS. 60–61 illustrate an example ball and stick, stick with hydrogen removed, and CPK model of a molecular formula $C_{33}H_{36}$ (molecular weight 432) octamantane.

FIGS. 62–63 illustrate an example ball and stick, stick with hydrogen removed, and CPK model of a molecular formula $C_{36}H_{40}$ (molecular weight 472) octamantane.

FIGS. 64–65 illustrate an example ball and stick, stick with hydrogen removed, and CPK model of a molecular formula $C_{37}H_{42}$ (molecular weight 486) octamantane.

FIGS. 66–67 illustrate an example ball and stick, stick with hydrogen removed, and CPK model of a molecular formula $C_{38}H_{44}$ (molecular weight 500) octamantane.

DETAILED DESCRIPTION OF THE INVENTION

This invention is directed to octamantane compositions comprising one or more octamantanes. However, prior to describing this invention in further detail, the following terms will first be defined.

Definitions

As used herein, the following terms have the following meanings.

Figure 1:
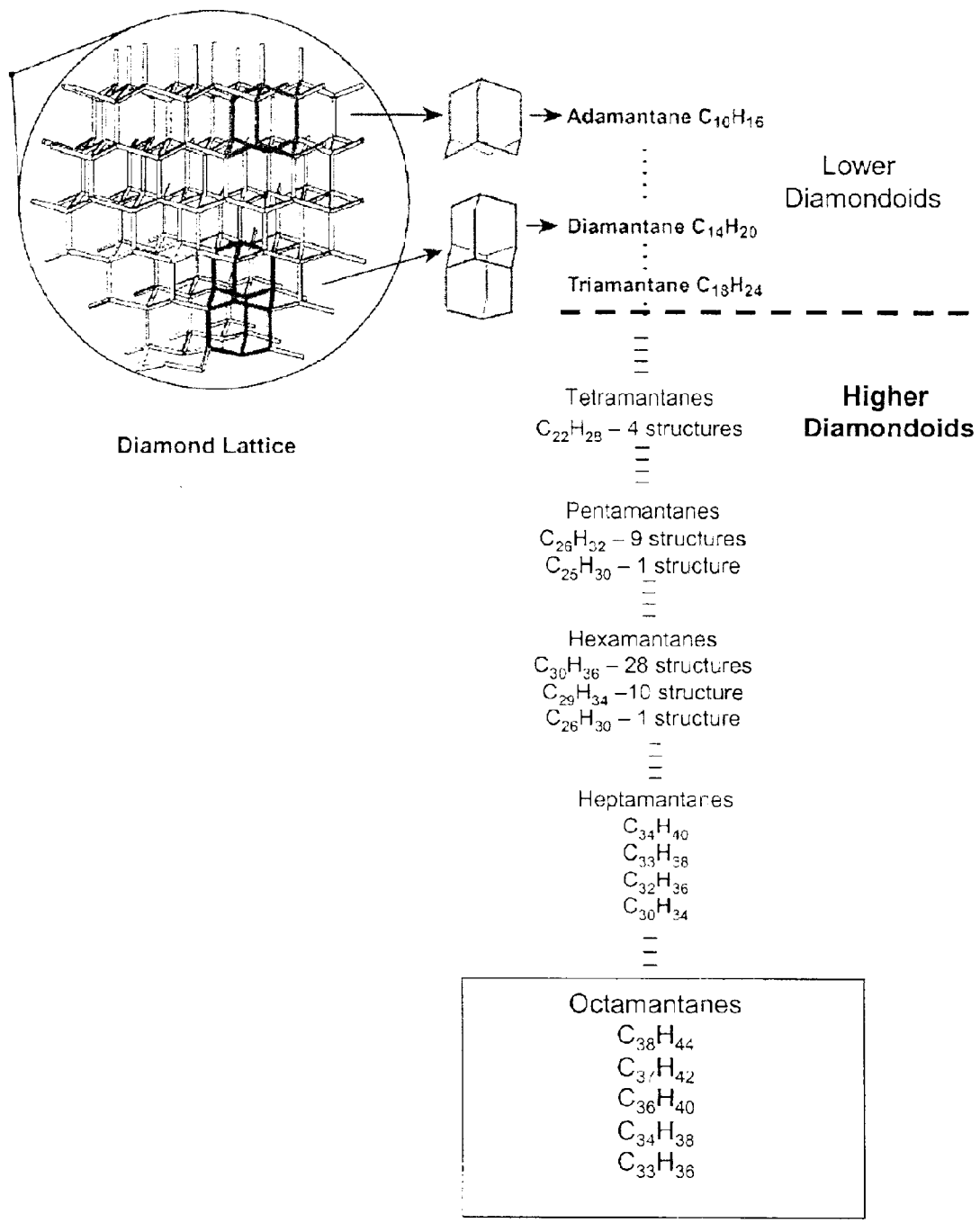
FIG. 1 illustrates the cage-shaped structure of diamondoids and their correlation to diamonds. Specifically.

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, dodecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "octamantanes," "higher diamondoids" and "nonoctamantane higher diamondoids" as these terms are defined herein.

The term "octamantanes" refer to diamondoids that are the face-fused octamers of adamantane. Among them, 18 have the molecular formula $C_{34}H_{38}$ (molecular weight 446). Octamantanes also have the molecular formulas: $C_{38}H_{44}$ (molecular weight 500), $C_{37}H_{42}$ (molecular weight 486), $C_{36}H_{40}$ (molecular weight 472) and $C_{33}H_{36}$ (molecular weight 432). Each of the octamantanes possesses a different three dimensional structure. Octamantane include "substituted" materials as described for diamondoids, generally.

The term "octamantane component" refers to any single substituted or unsubstituted octamantane, including optical isomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not octamantane components are referred to as "nonoctamantane higher diamondoids."

The term "feedstock" or "hydrocarbonaceous feedstock" refers to hydro-carbonaceous materials comprising recoverable amounts of one or more octamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. The latter is typically characterized as comprising components having a boiling point both below and above octamantane components, which show molecular weights ranging from 420 to 500, and have a range of boiling points beginning at about 525° C. (atmospheric equivalent pressure). Typical feedstocks may also contain impurities such as sediment, metals including nickel and vanadium and other inorganics. They may also contain heteromolecules containing sulfur, nitrogen and the like. All of these materials which are not octamantane components are referred to as "nonoctamantane materials or "nonpentamantane components."

The term "enriched" when used to describe the state of purity of one or more octamantane components refers to such materials at least partially separated from nononamantane materials, and in the case of "enriched" individual octamantane components, from other octamantane components so as to be at a concentration at least 25 and preferably at least 100 times as great as the concentration exhibited in a feedstock. Preferably "enriched" octamantane or "enriched" octamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%, 95%, or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate octamantane components by removal of nonoctamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched octamantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to enrich and isolate higher diamondoid compositions are set forth in U.S. Provisional Patent Application No. 60/262,842 filed Jan. 19, 2001; U.S. Provisional Patent Application No. 60/300,148 filed Jun. 21, 2001; U.S. Provisional Patent Application No. 60/307,063 filed Jul. 20, 2001; U.S. Provisional Patent Application No. 60/312,563 filed Aug. 15, 2001; and U.S. Provisional Patent Application No. 60/317,546 filed Sep. 5, 2001. These applications are herein incorporated by reference in their entirety.

To obtain the octamantane compositions described herein, a feedstock is selected such that said feedstock comprises recoverable amounts of octamantane. Preferably, such feedstock comprises at least about 1 parts per trillion of octamantane components. It is understood, of course, that feedstocks having higher concentrations of octamantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada.

The feedstocks used to obtain the compositions of this invention typically comprise nondiamondoid components having boiling points both below and above the octamantane components as well as lower diamondoids and nonoctamantane higher diamondoids. A sufficient amount of these contaminants is removed from the feedstocks to provide treated feedstocks from which the octamantane components can be enriched and recovered.

The removal of nondiamondoids, lower diamondoids and nonoctamantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nonoctamantane diamondoids having boiling points less than that of the lowest boiling point octamantane component. Temperature profiles for distillation runs and the resulting distillation cuts can be determined on the basis of the octamantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified octamantane. The cuts, which are enriched in octamantane or a particular octamantane component of interest, are retained and may require further purification. For recovery of octamantanes, the preferred distillation cuts are taken at atmosphere equivalent boiling point temperatures of from 370° C. to about 610° C., preferably from 420° C. to about 560° C. and especially 420° C. to about 530° C. (atmospheric boiling points), it being understood that substituted octamantanes may accordingly shift these preferred temperatures to higher temperatures due to the addition of substituent groups. Additional temperature refinements will allow for higher purity cuts for the octamantane of interest. Other methods for the removal of contaminants and further purification of an enriched octamantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours). The specific conditions employed are selected such that recoverable amounts of octamantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a preferred embodiment, is not always necessary to facilitate the recovery, isolation or purification of the octamantane components. Other separation methods may allow for the concentration of these octamantane components to be sufficiently high in certain feedstocks that direct purification methods such as chromatography including preparative gas chromatography and high performance liquid chromatography and crystallization may be used to isolate octamantane components.

Even after distillation or thermal degradation/distillation, further purification of the octamantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated octamantanes. These provisions can be combined. For example, preparative capillary gas chromatography can be coupled with high performance liquid chromatography as a first or subsequent separation method.

Further processing using these methods allow for more refined separations which can lead to a pure octamantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the octamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction", R. M. Smith, Elsevier Science, December 1997, incorporated herein by reference.

Compositions

This invention is directed to compositions comprising one or more octamantane components wherein said compositions comprise at least about 25 weight percent octamantane components based on the total weight of the diamondoids in the compositions. The compositions preferably comprise from about 50 to 100 weight percent, preferably about 70 to about 100 weight percent, more preferably about 90 to 100 weight percent and even more preferably about 95 to 100 weight percent octamantane components based on the total weight of the diamondoids in the composition.

Such octamantane-enriched compositions are obtained through the series of unit operations described above which can be used to concentrate octamantanes to at least 25 times and more preferably at least 100 times the levels at which they occur in readily-available feedstocks. The total weight percent of octamantane components in the compositions is preferably at least 10% by weight based upon the total weight of the composition. In a more preferred aspect the total weight percent of octamantane components is from 50 to 100 weight percent, more preferably 70 to 100 weight percent and even more preferably 95 or 99 to 100 weight percent based upon the total weight percent of the composition.

In other aspects, the compositions comprise an enriched individual octamantane component such that they contain from 70 to 100 weight percent, more preferably from 90 to 100 weight percent, even more preferably from 95 to 100 weight percent and most preferably from 99 to 100 weight percent of a single octamantane component including isolated optical isomers thereof.

Figure 66:
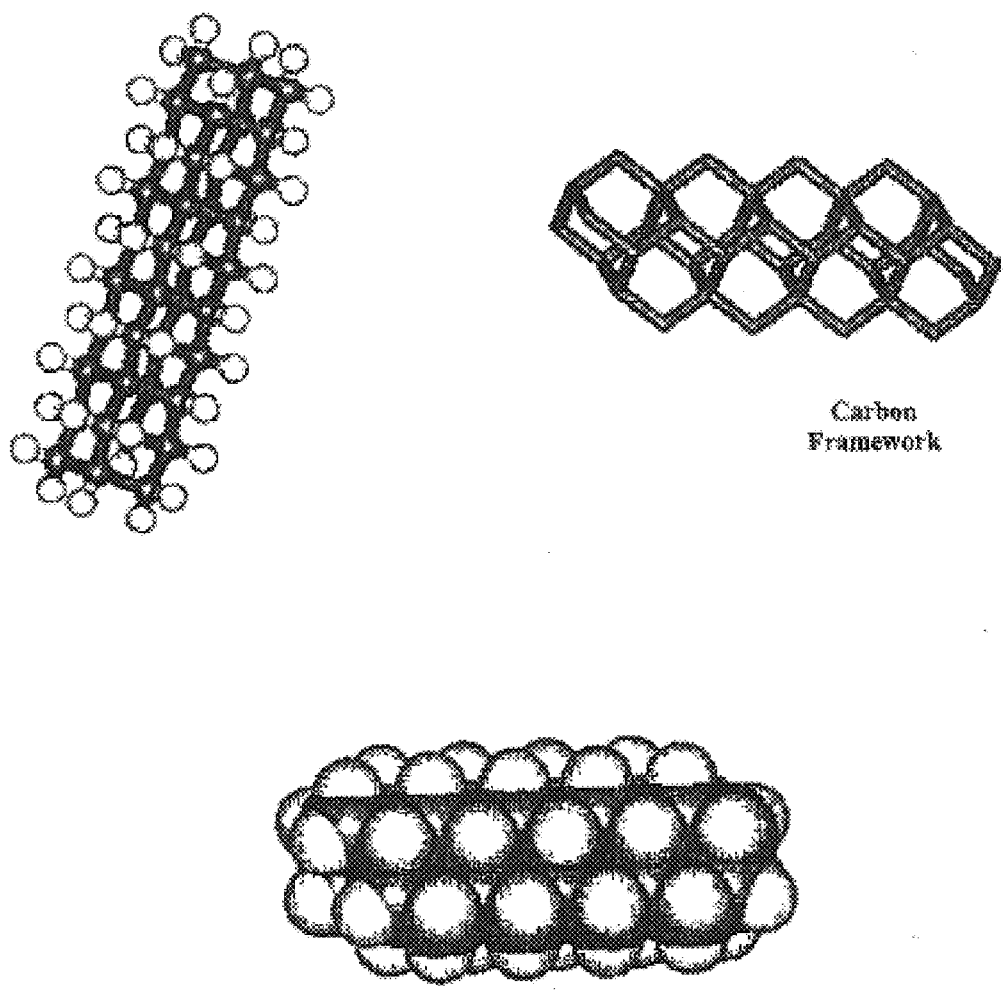

In a most preferred embodiment, the composition aspects of this invention are directed to the 18 octamantanes having the molecular formula $C_{34}H_{38}$ (molecular weight 446) with the structures and lattice planes shown in FIGS. 24 through 59, which also name these compounds using the convention as outlined in Balaban et al.[7] In another preferred aspect, the compositions are directed to the octamantanes having the molecular formula $C_{38}H_{44}$ (molecular weight 500) with an example structure and lattice plane shown in FIGS. 66–67. This invention is also directed to the octamantanes having the molecular formula $C_{33}H_{36}$ (molecular weight 432), molecular formula $C_{36}H_{40}$ (molecular weight 472) and molecular formula $C_{37}H_{42}$ (molecular weight 486) with an example structure and lattice planes shown in FIGS. 60–65. The composition aspects of this invention are directed to compositions comprising one or more of these octamantanes and for the processes for recovering said compositions enriched with such octamantane components.

At the high octamantane concentrations and purities achieved by the present invention, octamantanes components can form crystal structures. Accordingly, another aspect of this invention is directed to octamantane crystals, whether crystals of a single octamantane component, co-crystals comprising crystals of at least two octamantane components or co-crystals of octamantane components with other higher diamondoids, such as heptamantane components.

The octamantanes recovered and isolated in this invention include substituted octamantane components. These naturally occurring substituted octamantanes have similar properties to the unsubstituted octamantane components described herein and are present in the feedstocks. Substituted octamantanes may act as useful intermediates in various octamantane applications or can be de-alkylated to yield the corresponding unsubstituted octamantanes. Substituted octamantanes contain 1 to 10 alkyl substituents, and more preferably 1 to 4 such substituents.

The most prevalent substituted octamantanes in the feedstocks used are octamantanes substituted with lower alkyls. The most prevalent of these are methyl and ethyl-substituted octamantanes, including methyl, ethyl, dimethyl, and trimethyl octamantanes.

Utility

These octamantane-containing compositions are useful in micro- and molecular-electronics and nanotechnology applications. In particular, the rigidity, strength, stability, thermal conductivity, variety of structural forms and multiple attachment sites shown by octamantanes makes possible accurate construction of robust, durable, precision devices with nanometer dimensions. These special structural characteristics set these compounds apart from acyclic molecules, from condensed-ring systems and even from bridged-ring counterparts. The great stability, nanometer size, variable yet rigid geometry, well defined distances for places of attachment, nonplanar bridgeheads lead to their unique features. Due to the rigidity, specialized geometry, 3-dimensional shape and nanometer size of the octamantane components, it is expected that molecular aggregates and building blocks comprising them will enable construction and synthesis of a unprecedented array of desirable materials that will find applications in molecular electronic computing devices, reduced-size machines such as molecular robots and self-replicating manufacturing systems. Alternatively, the octamantanes may be used as novel materials of construction with special chemical, optical, electric and thermal conductivity properties for coatings, film layering and other applications taking advantage of the diamond-like properties, etc.

In addition, octamantane-containing compositions can also be used in a high-quality lubricant which exhibits a high Viscosity Index and a very low pour point. When so employed, these lubricants comprise from about 0.1 to 10 weight percent octamantanes.

Still further, these octamantane-containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | |
|---|---|
| API = | American Petroleum Institute |
| ATM EQV = | atmospheric equivalent |
| EOR Traps = | end of run traps |
| FID = | flame ionization detector |

-continued

| | |
|---|---|
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

EXAMPLES

Example 1

Isolation of Octamantane Components

The purpose of this example is to demonstrate procedures for the isolation of octamantane components. These procedures employed Feedstock B and a pyrolysis step, however this procedure could be facilitated using other materials, such as Feedstock A, and without the pyrolysis step. After removal of lower boiling point nonoctamantane components (including some lower diamondoids and tetramantanes from the feedstock by distillation), the octamantane components in this example were recovered by chromatography and crystallization. The distillation preferably can be operated to provide specific cuts, thus removing both lower and higher boiling point components, leaving only components within a desired boiling point range.

Figure 3:
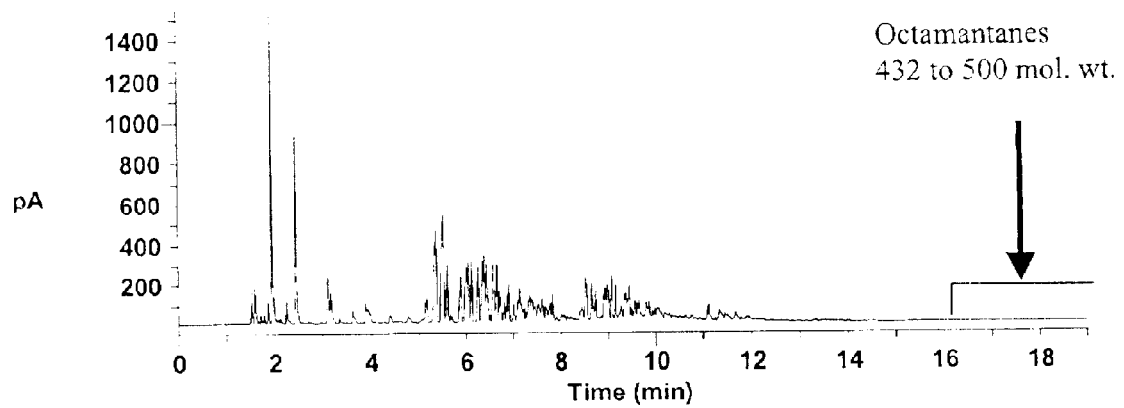
FIG. 3 illustrates the gas chromatogram of a gas condensate feedstock; one of the original feedstocks used in the Examples (Feedstock A). Octamantanes are present at low concentrations, not detectable, but are shown in vacuum distillation fractions (FIG. 6).
Figure 4:
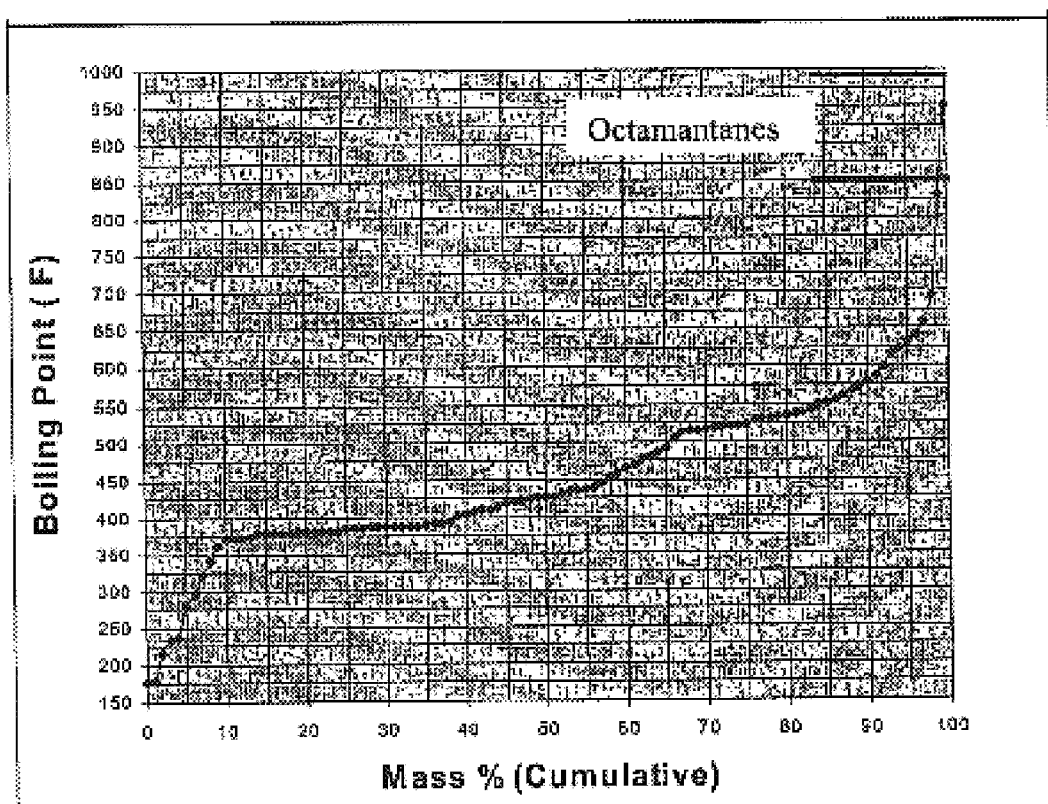
FIG. 4 illustrates a simulated distillation profile of a gas condensate feedstock containing petroleum byproducts used in the Examples (Feedstock B). Boiling points depicted are atmospheric equivalents. Octamantanes were found in the atmospheric residue (650° F.+) of Feedstock B.

Step 1:

Suitable starting materials were obtained. These materials included a gas condensate, Feedstock A (a gas chromatogram of this material is depicted in FIG. 3), and a gas condensate containing petroleum byproducts Feedstock B (a high temperature simulated distillation profile of this type of material is depicted in FIG. 4). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2:

Samples from Feedstocks A and B were distilled into a number of fractions based on boiling points to separate the lower boiling point components (nondiamondoids and lower diamondoids) and to further concentrate and enrich octamantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

Figure 5:
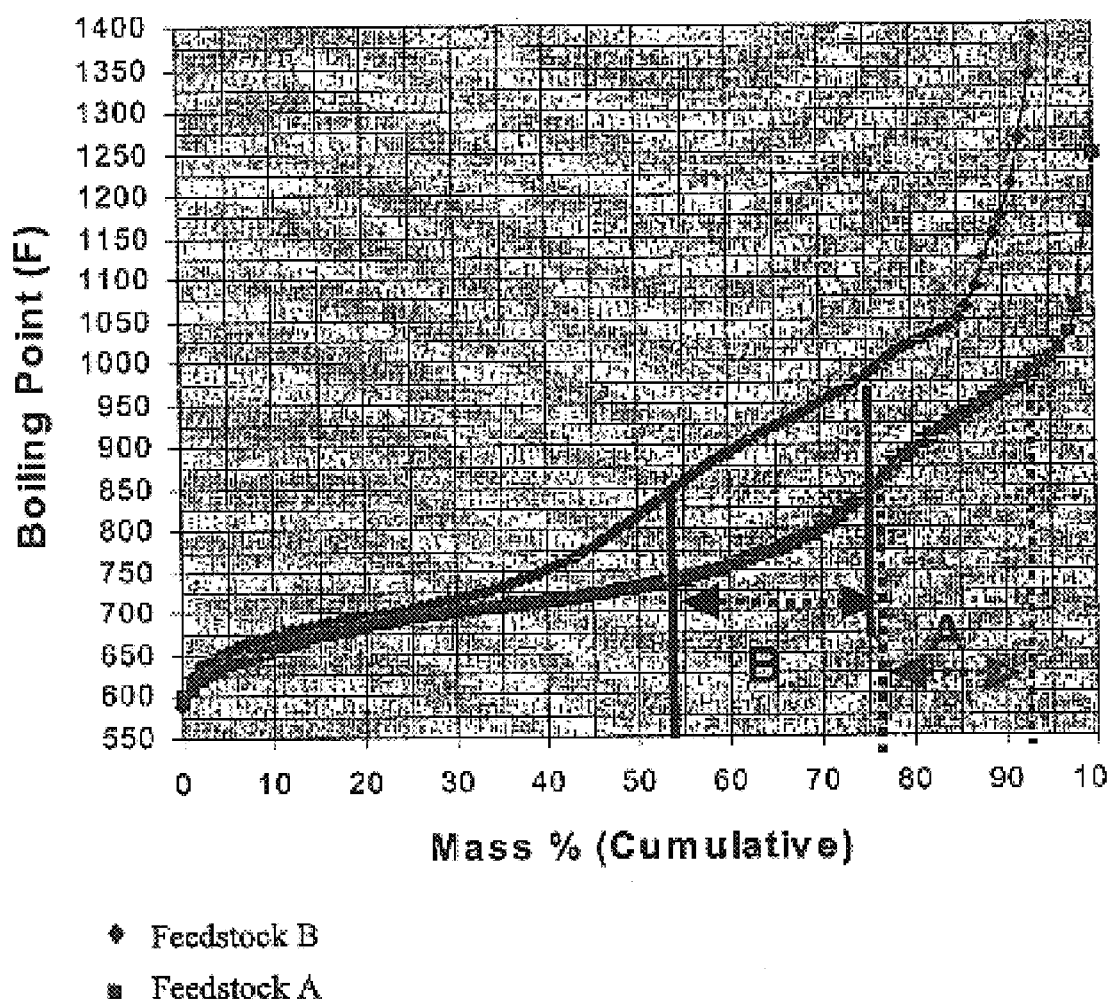
FIG. 5 illustrates a high temperature simulated distillation profile of atmospheric residue of diamondoid rich gas condensates; Feedstock A and Feedstock B. This Figure also illustrates the n-paraffin carbon number atmospheric equivalent boiling points. Labels A and B show the portions of each feedstock which contain the octamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the octamantane-containing fractions. In terms of atmospheric equivalent boiling points, the octamantane components boil predominately within the range of 370° C. to about 610° C. with a large portion within the range of 450° C. to about 530° C. Heptamantanes of molecular weight 448 also occur within the lower boiling point octamantane fractions. The lower mass percent shown for the octamantane-containing fractions of Feedstock B, as compared to Feedstock A was due to nondiamondoid materials in Feedstock B. The nondiamondoid material can be removed by subsequent processes such as pyrolysis.

A sample of gas condensate, Feedstock A was distilled into 38 fractions to remove lower diamondoids and concentrate higher diamondoids including octamantanes. Fraction 38 was a recovered distillate, predominately boiling in the range of from 700 to 850° F. (atmospheric equivalent). The boiling points of these fractions are given as atmospheric equivalent temperatures, however, the actual distillation can occur at other pressures and corresponding temperatures.

Figure 6:
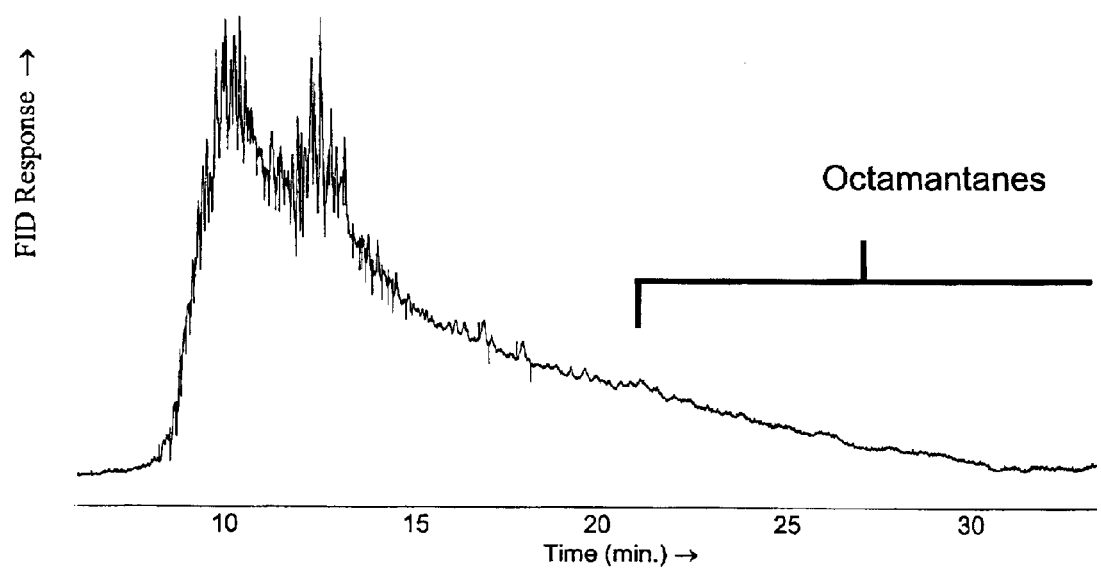
FIG. 6 illustrates gas chromatographic profiles of vacuum distillate residue containing octamantanes and higher diamondoids from a gas condensate, Feedstock A.
Figure 7:
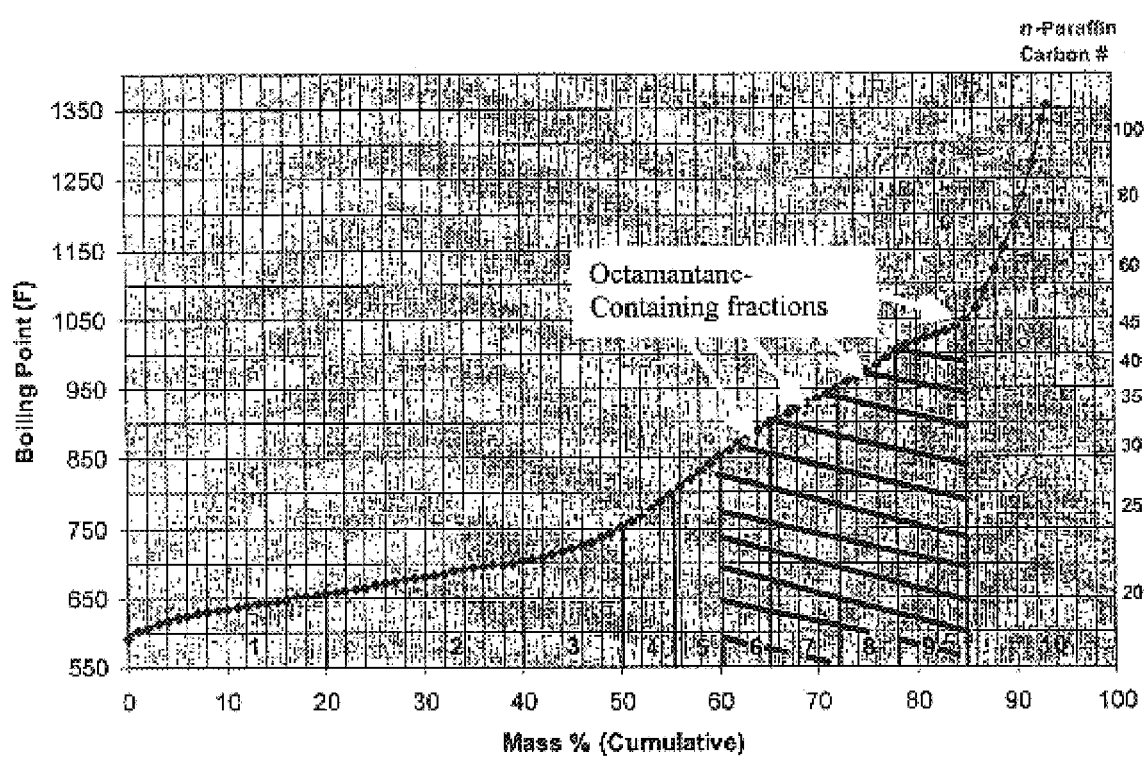
FIG. 7 illustrates a high temperature simulated distillation profile of Feedstock B using the atmospheric distillation 650° F.+ bottoms as feedstock. This FIG. also illustrates the targeted cut points (1–10) for higher diamondoid isolations. Octamantanes are contained primarily in distillate fractions 6 through 9.
Figure 8:
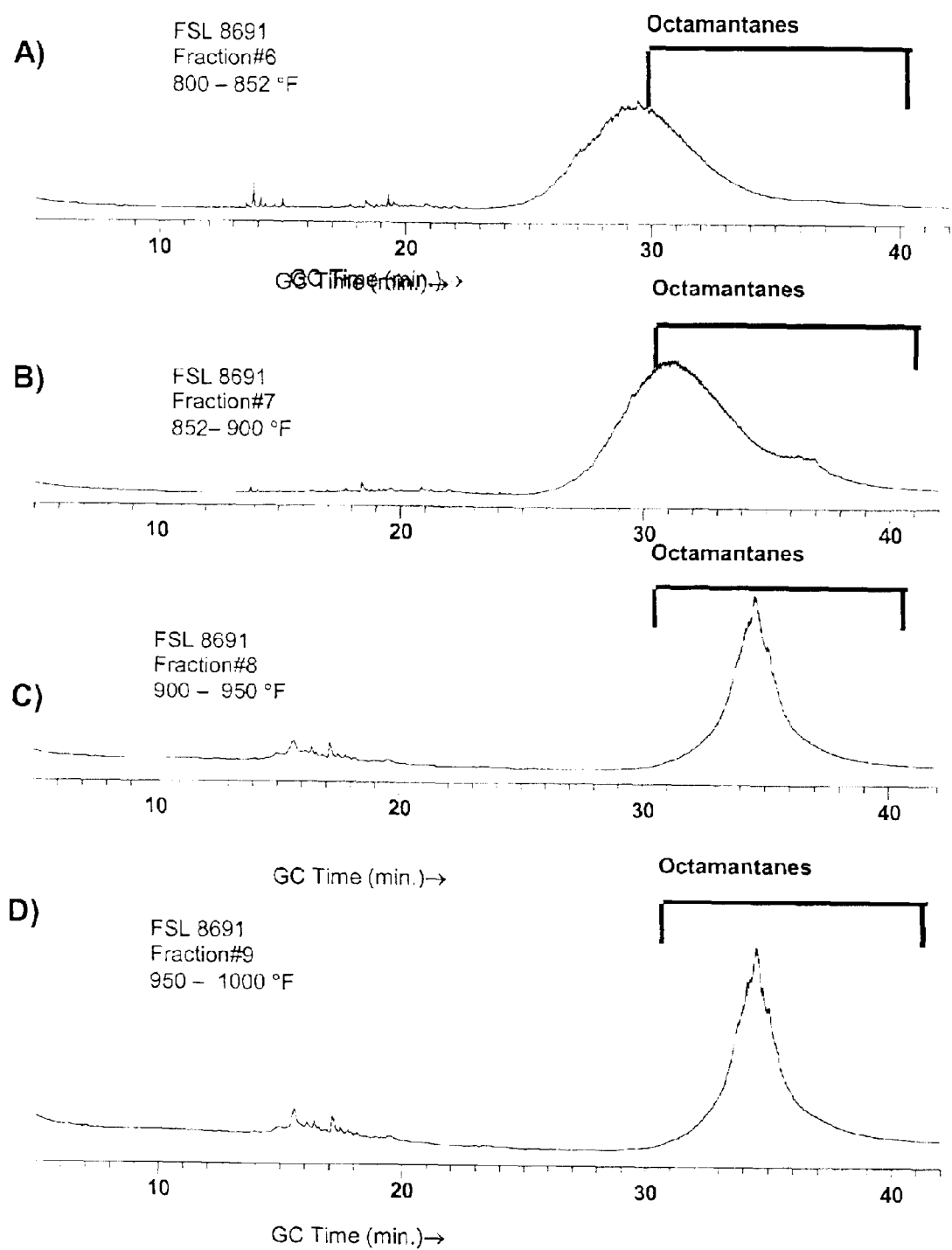
FIGS. 8(A, B, C, D) illustrates the gas chromatograms of vacuum distillate Fractions #6, #7, #8 and #9 of Feedstock B atmospheric distillation 650° F. + bottoms illustrated in FIG. 7 and exemplified in Example 1.

Additionally, Feedstock B was distilled into fractions containing higher diamondoids guided by a high temperature simulated distillation curve (FIG. 7). Comparison of FIGS. 6 and 8 shows that Feedstock B contains impurities not present in Feedstock A. The feed to the high temperature distillation process was the atmospheric 650° F.+ bottoms. Whole Feedstock B distillation reports are given in Tables 2A&B. Tables 3 A&B, illustrate the distillation reports for Feedstock B 643° F.+ distillation bottoms.

TABLE 2A

Distillation Report for Feedstock B (FSL# 8471)
Feedstock B
Column Used: Clean 9" × 1.4" Protruded Packed

| | VAPOR TEMP ° F. | | DISTILLATION RECORD | | | | NORMALIZED | | ACTUAL | |
|---|---|---|---|---|---|---|---|---|---|---|
| CUT | ST-END | | WEIGHT G | VOLUME ml @ 60° F. | API 60/60 | DENSITY @ 60° F. | WT PCT | VOL PCT | WT PCT | VOL PCT |
| 1 | 226 – | 349 | 67.0 | 80 | 38.0 | 0.8348 | 7.61 | 8.54 | 7.39 | 8.26 |
| 2 | 349 – | 491 | 507.7 | 554 | 22.8 | 0.9170 | 57.65 | 59.12 | 55.98 | 57.23 |
| 3 | 491 – | 643 | 269.6 | 268 | 9.1 | 1.0064 | 30.62 | 28.60 | 29.73 | 27.69 |
| COL HOLDUP | | | 0.2 | 0 | 6.6 | 1.0246 | 0.02 | 0.00 | 0.02 | 0.00 |
| BTMS | 643 + | | 36.1 | 35 | 6.6 | 1.0246 | 4.09 | 3.74 | 3.98 | 3.62 |
| EOR TRAPS | | | 0.0 | 0 | | | 0.00 | 0.00 | | 0.00 |
| TOTALS | | | 880.6 | 937 | | | 100.00 | 100.00 | 97.09 | 96.80 |
| LOSS | | | 26.4 | 31 | | | | | 2.91 | 3.20 |
| FEED | | | 907.0 | 968 | 19.5 | 0.9371 | | | 100.00 | 100.00 |
| BACK CALCULATED API AND DENSITY | | | | | 19.1 | 0.9396 | | | | |

TABLE 2B

Distillation Report for Feedstock B (FSL # 8471)
Feedstock B
Column Used: Clean 9" × 1.4" Protruded Packed

| TEMPERATURE DEGREES F. | | | | | | | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | Cut 2 looks Milky, White crystals form in Run Down Line. Heat Lamp applied to drip tube. | | | | | | | | | |
| | Cool to transfer btms to smaller flask. | | | | | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| | Shutdown due to dry pot | | | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B (FSL # 8691)
Feedstock B - Atmospheric distillation resid 650° F. + bottoms
Column Used: Sarnia Hi Vac

| TEMPERATURE DEGREES F. | | | | | | VOL | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |
| 315 | 601.4 | 350 | 5.000 | | | START OVERHEAD | | | | |
| 344 | 636.8 | 382 | 5.000 | | | 300 | READING | | | |

TABLE 3A-continued

Vacuum Distillation Report for Feedstock B (FSL # 8691)
Feedstock B - Atmospheric distillation resid 650° F. + bottoms
Column Used: Sarnia Hi Vac

| TEMPERATURE DEGREES F. | | | | | | | API GRAVITIES | | |
|---|---|---|---|---|---|---|---|---|---|
| VAPOR | | | | | VOL | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | MID AND | END OF RUN TRAPS | | | | 20 | 17.8 | (mathematically combined) | | |
| | | VOLUME DISTILLED | | | | 2701 | | | | |
| | | COLUMN HOLDUP | | | | 4 | 4.0 | 0.0 | 0.0 | 3.4 |
| | | BOTTOMS | | | | 593 | 621.8 | 11.0 | 214.0 | 3.4 |
| | | RECOVERED | | | | 3298 | 3311.7 | | | |
| | | FEED CHARGED | | | | 3298 | 3326.3 | 18.0 | 234.0 | 8.6 |
| | | LOSS | | | | −5 | 14.6 | | | |

TABLE 3B

Distillation Report for Feedstock B-btms (FSL # 8691)
Feedstock B - Atmospheric distillation resid 650° F. + bottoms
Column Used: Sarnia HiVac

| CUT | VAPOR TEMP ST-END, ° F. | | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|---|
| 1 | 601 | − | 656 | 666.4 | 639 | 4.1 | 1.0435 | 20.12 | 19.38 | 20.03 | 19.40 |
| 2 | 656 | − | 702 | 666.9 | 646 | 5.6 | 1.0321 | 20.14 | 19.59 | 20.05 | 19.62 |
| 3 | 702 | − | 752 | 334.3 | 330 | 8.3 | 1.0122 | 10.09 | 10.01 | 10.05 | 10.02 |
| 4 | 752 | − | 800 | 167.7 | 173 | 14.5 | 0.9692 | 5.06 | 5.25 | 5.04 | 5.25 |
| 5 | 800 | − | 852 | 167.3 | 181 | 21.7 | 0.9236 | 5.05 | 5.49 | 5.03 | 5.50 |
| 6 | 852 | − | 900 | 167.1 | 181 | 21.9 | 0.9224 | 5.05 | 5.49 | 5.02 | 5.50 |
| 7 | 900 | − | 950 | 238.4 | 257 | 21.2 | 0.9267 | 7.25 | 7.79 | 7.17 | 7.80 |
| 8 | 950 | − | 976 | 85.4 | 91 | 18.9 | 0.9408 | 2.58 | 2.76 | 2.57 | 2.76 |
| 9 | 976 | − | 1000 | 80.8 | 85 | 18.2 | 0.9452 | 2.44 | 2.58 | 2.43 | 2.58 |
| 10 | 1000 | − | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.00 | 100.00 | 99.56 | 100.15 |
| LOSS | | | | 14.6 | −5 | | | | | 0.44 | −0.15 |
| FEED | | | | 3326.3 | 3293 | 8.6 | 1.0100 | | | 100.00 | 100.00 |
| BACK CALCULATED API & DENSITY | | | | | | 9.4 | 1.0039 | | | | |

TABLE 4

Elemental Composition of Feedstock B
Analyses on Feedstock B Atmospheric Distillation 650+ F. Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates data from elemental analyses of Feedstock B atmospheric distillation (650+° F.) residue including some of the identified impurities. Table 4 displays the weight percent nitrogen, sulfur, nickel and vanadium present within this feedstock. These materials were removed in subsequent steps.

Step 3:

The higher diamondoids enriched by the separations of Step 2 were further treated to isolate a octamantane fraction. In one case the distillation fraction 38 of Feedstock A was passed through a silica-gel gravity liquid chromatographic column (using cyclohexane elution solvent) to remove polar compounds and asphaltenes and concentrate higher diamondoids. The use of silver nitrate impregnated silica gel (10% by weight $AgNO_3$) provides cleaner diamondoid-containing fractions by removing the free aromatic and polar components. Higher diamondoids elute in the first eluting cyclohexane fraction off the column (before aromatic hydrocarbons appeared in the column eluent column. While it is not necessary to use this chromatographic separation method, it facilitates subsequent steps.

Alternatively, pyrolysis products (as disclosed in Example 2) prepared using distillate fractions of Feedstock B could be passed through a silica-gel or $AgNO_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Figure 10:
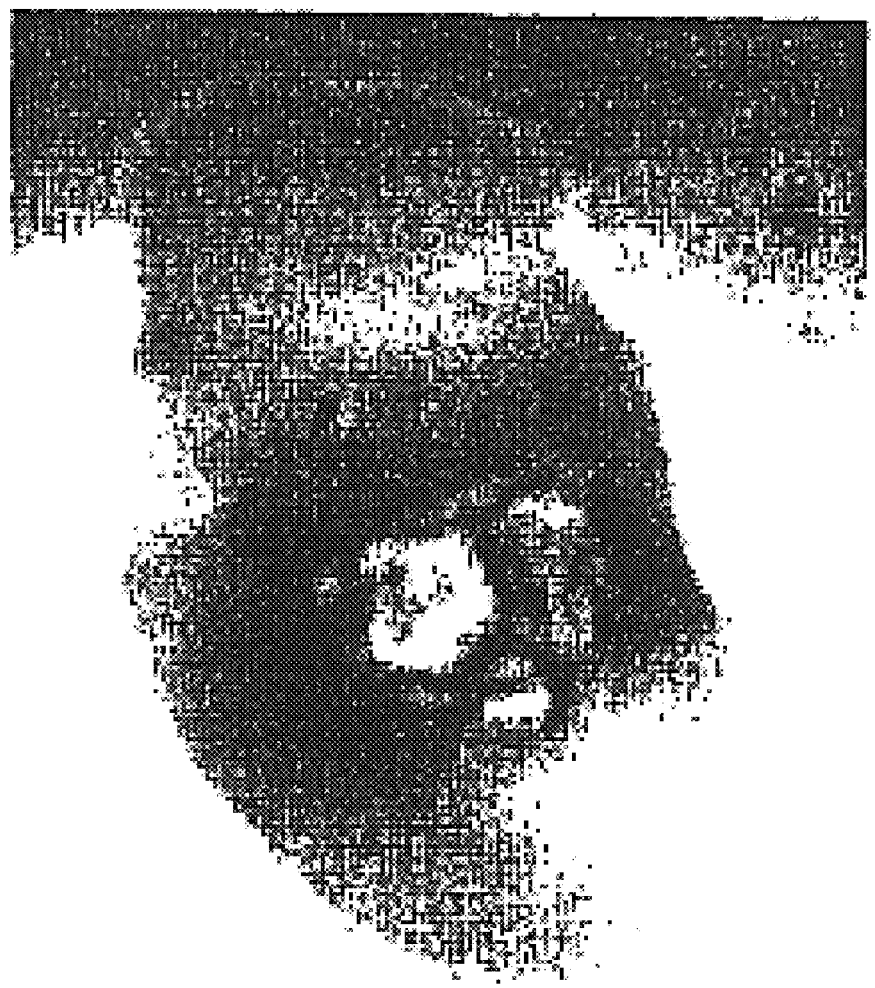
FIG. 10 illustrates a photomicrograph of octamantane #1 crystals isolated from Feedstock B by high performance liquid chromatography.
Figure 13:
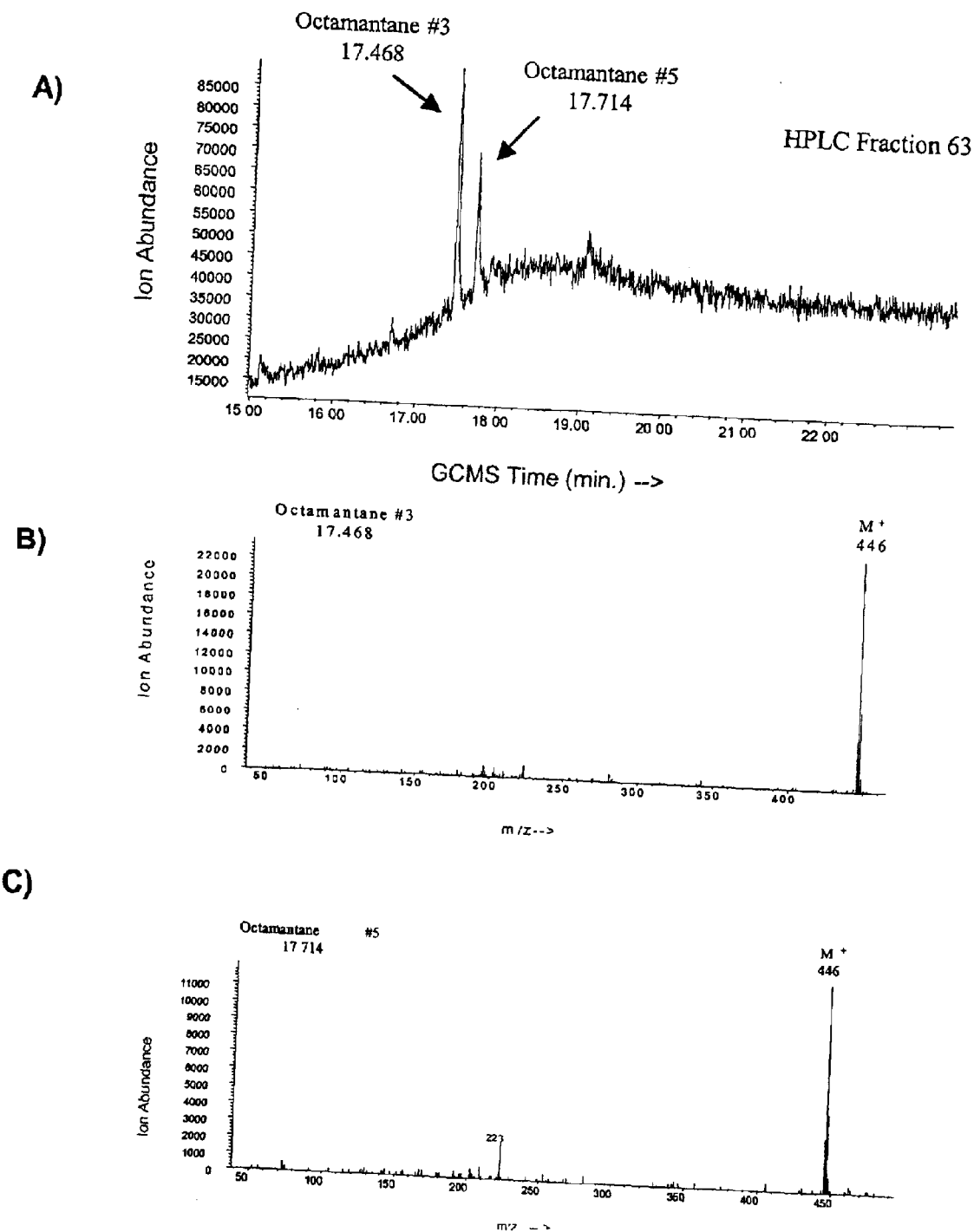
FIGS. 13(A, B, and C) illustrates GC/MS total ion chromatogram (TIC) and mass spectrum of co-crystalline octamantane #3 and octamantane #5 (FIG. 14) grown from ODS HPLC fraction #63 (FIG. 11).

Step 4:

The octamantane enriched fraction from step 3 was then subjected to reverse-phase HPLC. In some instances, HPLC provided sufficient enrichment (see GC/MS data in FIG. 9) of some octamantanes to allow for their crystallization (see photomicrograph of octamantane #1 crystal in FIG. 10). Crystals of octamantane had never existed before this isolation. Octamantanes can also co-crystallize from HPLC fractions as illustrated in FIGS. 13 and 14 for octamantane #3 and octamantane #5. Some octamantane components require more than one HPLC separation to provide sufficient enrichment to allow for crystallization.

Suitable HPLC columns for use are well known to those skilled in the art. In some cases, reverse-phase HPLC with acetone as mobile phase can be used to effect this purification. A preparative ODS HPLC run of Feedstock B distillate cut 7 pyrolysis product saturated hydrocarbon fraction was performed and the HPLC chromatogram recorded using a differential refractometer. HPLC fractions were analyzed by GC/MS to determine octamantane HPLC elution times (FIG. 11) and monitor purity. The HPLC columns used were two 50 cm×20 mm I.D. WHATMAN octadecyl silane (ODS) columns operated in series (Whatman columns are manufactured by Whatman Inc., USA). A 500 microliter sample of an acetone solution of the cut 7 pyrolysis product saturated hydrocarbon fraction (25 mg) was injected into the columns. The columns were set-up using acetone at 5.00 ml/min as a mobile phase carrier. While using this HPLC system, some octamantanes reached purity for individual octamantanes to crystallize. For example, FIG. 9 illustrates a GC/MS total ion chromatogram and mass spectra of an HPLC fraction in which octamantane #1 has been purified to the point where it formed crystals (see FIG. 10). FIGS. 15 and 16 are GC/MS total ion chromatograms and mass spectra of HPLC fractions enriched in octamantane components which require further separation for crystallization to occur. Such separation could consist of further HPLC using columns of different selectivities (Example 4) or preparative gas chromatography (Example 3). As an example, a HYPERCARB HPLC column (manufactured by Thermo Hypersil, Penn, USA) or other suitable column could be used to purify octamantanes to concentrations necessary for them to crystallize (See Example 4).

Step 5:

After obtaining crystals of suitable size, non-enantiomeric octamantanes material can be sent for structural determination using X-ray diffraction. Enantiomeric octamantanes must undergo further separations to resolve the two components.

Example 2

Enrichment of Octamantanes Using Pyrolysis

A method was developed to further purify distillate fractions such as distillate fractions #6–9 obtained from Feedstock B—Atmospheric distillation 650° F.+ bottoms (Table 3 A/B) exploiting the great thermal stability of the octamantanes relative to other crude oil components. FIGS. 8(A, B, C, D) respectively, shows the GC profiles of the distillate fractions #6–9 indicating the octamantane portions from Feedstock B—Atmospheric distillation 650° F.+ bottoms (see FIG. 7 and Table 3 A&B).

Removal of Non-diamondoids Using Pyrolysis

This method uses a reactor to pyrolyze and degrade a portion of the non-diamondoid components while enriching the diamondoids in the residue. Such reactors can operate at a variety of temperatures and pressures. FIGS. 12(A, B) illustrates this method and shows a gas chromatogram of the Feedstock B 650° F.+ distillation fraction 7 (Table 3, FIG. 7) before pyrolysis and the resulting pyrolysis product. Prior to pyrolysis, the octamantane peaks are obscured by the presence of non-diamondoid components (FIG. 12B). Pyrolysis can be used to degrade the non-diamondoid components to easily removable gas and coke like solids facilitating the isolation of octamantanes.

A PARR® reactor, from PARR INSTRUMENT COMPANY, Moline, Ill., was used to process the distillation fractions obtained from vacuum distillation of a feedstream. For this example, Feedstock B 650° F.+ distillation fraction 7 was used as a feedstock for pyrolysis. Pyrolysis was then conducted on 18.6 grams of this sample by heating the sample under vacuum in a vessel at 450° C. for 16.3 hours.

FIG. 12B shows the gas chromatogram of the distillation fraction and FIG. 12A shows the chromatograph of the products of the pyrolytic process. A comparison of the traces in FIGS. 12(A, B) show that the pyrolysis process has removed major non-diamondoid components leaving a residue enriched in octamantane components.

Example 3

Isolation of Octamantanes Using HPLC and Preparative GC

Ninety-five HPLC fractions from Example 1 were analyzed by GC/MS to determine the GC retention times of individual octamantanes (examples are shown in FIGS. 9, 13, 15 and 16). Individual octamantane components with molecular weight 446 were assigned a number according to their elution order on our GC/MS assay (FIG. 11). Retention times shift for example, with time or changing column conditions, therefore, the times listed in FIG. 11 are exemplary. A reference sample can be used to adjust the assay for these changing conditions.

Similar assays, as above, could be prepared for the other molecular weight octamantanes. This assigned number was used to identify individual octamantanes in subsequent analyses. Note that enantiomeric pairs are not resolved in this analysis and so these enantiomeric pairs (racemic mixtures) were assigned a single number.

Using retention times and GC patterns determined from GC/MS analysis, a two-column preparative capillary gas chromatograph can be used to isolate octamantanes from the HPLC fractions. This methodology was demonstrated for heptamantanes as illustrated in FIG. 17. In this example the cut times for the heptamantanes were set for the first preparative capillary GC column, methyl silicone DB-1 equivalent, using the retention times and patterns from a GC/MS assay. The results are shown in the top of FIG. 17A, identified as "peaks cut and sent to column 2" which contains two of the heptamantane from Feedstock B. The preparative capillary gas chromatograph used was manufactured by Gerstel, Inc., Baltimore, Md., USA. However, other gas chromatographs could be used.

The first column was used to concentrate the heptamantanes by taking cuts that were then sent to the second column (see FIG. 17B illustrated for heptamantane #1 and #2). The second column, phenyl-methyl silicone a DB-17 equivalent, further separated and purified the heptamantanes and then was used to isolate peaks of interest and retain them into individual vials (traps 1–6). GC trap fraction 2 was collected and further processed for the separation of heptamantane #1. GC trap fraction 4 was collected and further processed for the separation of heptamantane #2. Subsequent GC/MS analysis of trap #2 material (FIG. 18) showed it to be heptamantane #1 based upon the earlier run GC/MS assay. Similarly, the GC/MS analysis of trap #4 material (FIG. 19) showed it to be heptamantane #2. This procedure can easily be used to isolate octamantanes from HPLC fractions such those shown in FIGS. 13 and 15.

Figure 21:
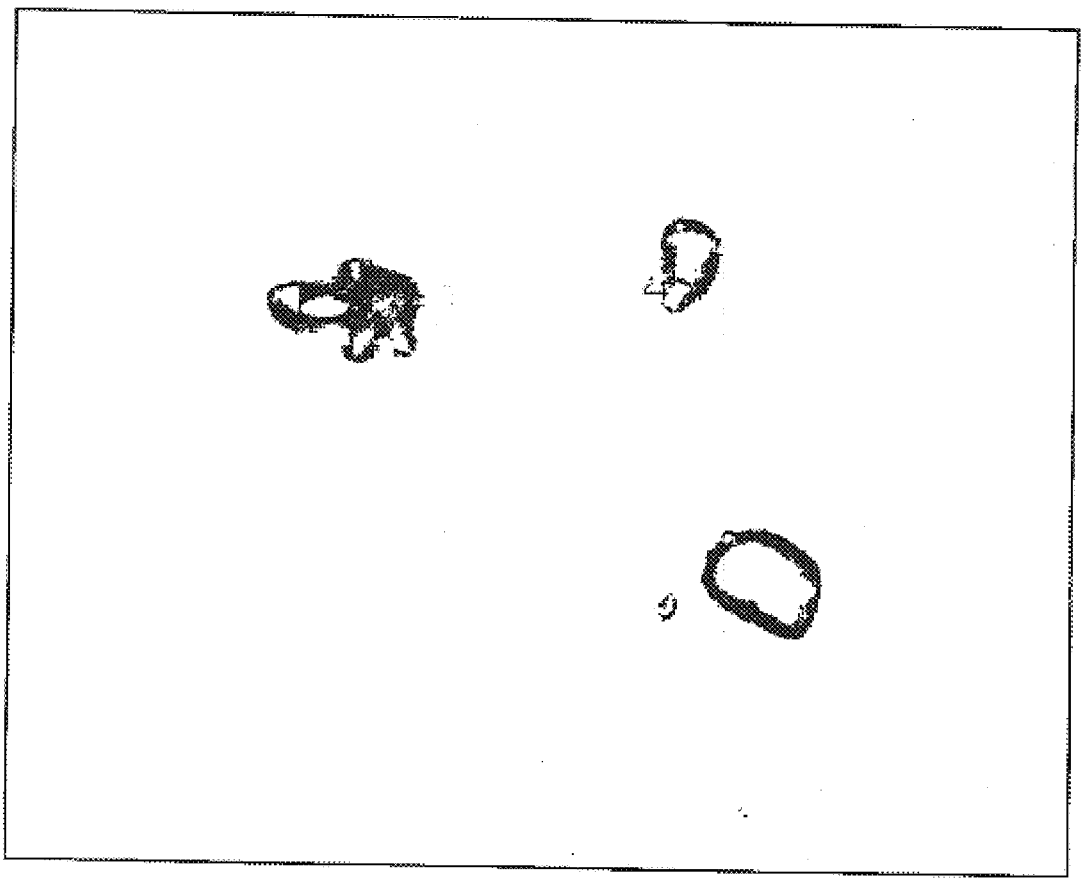
FIG. 21 illustrates a photomicrograph of heptamantane #2 crystals isolated from Feedstock B by preparative capillary gas chromatography.
Figure 25:
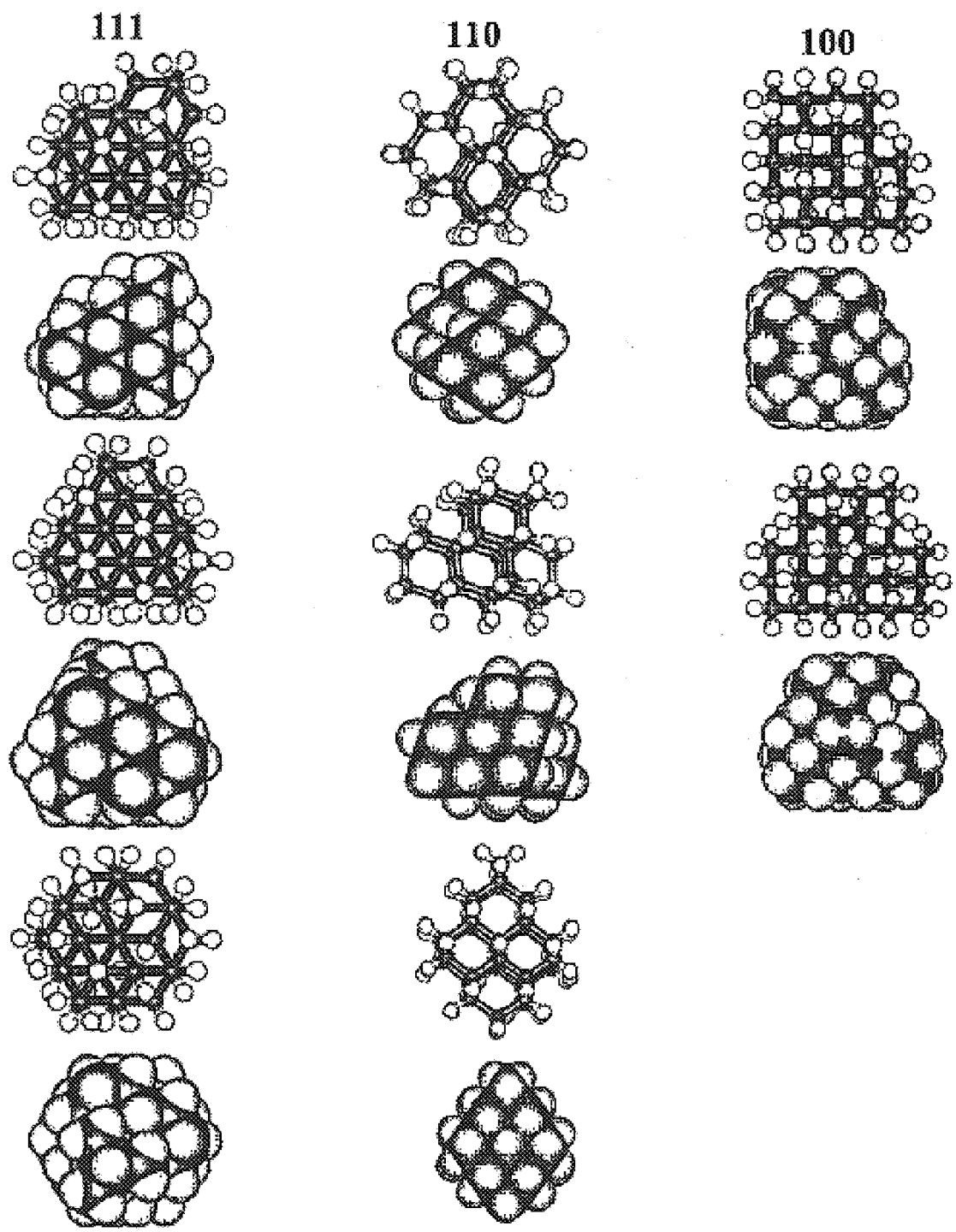
Figure 29:
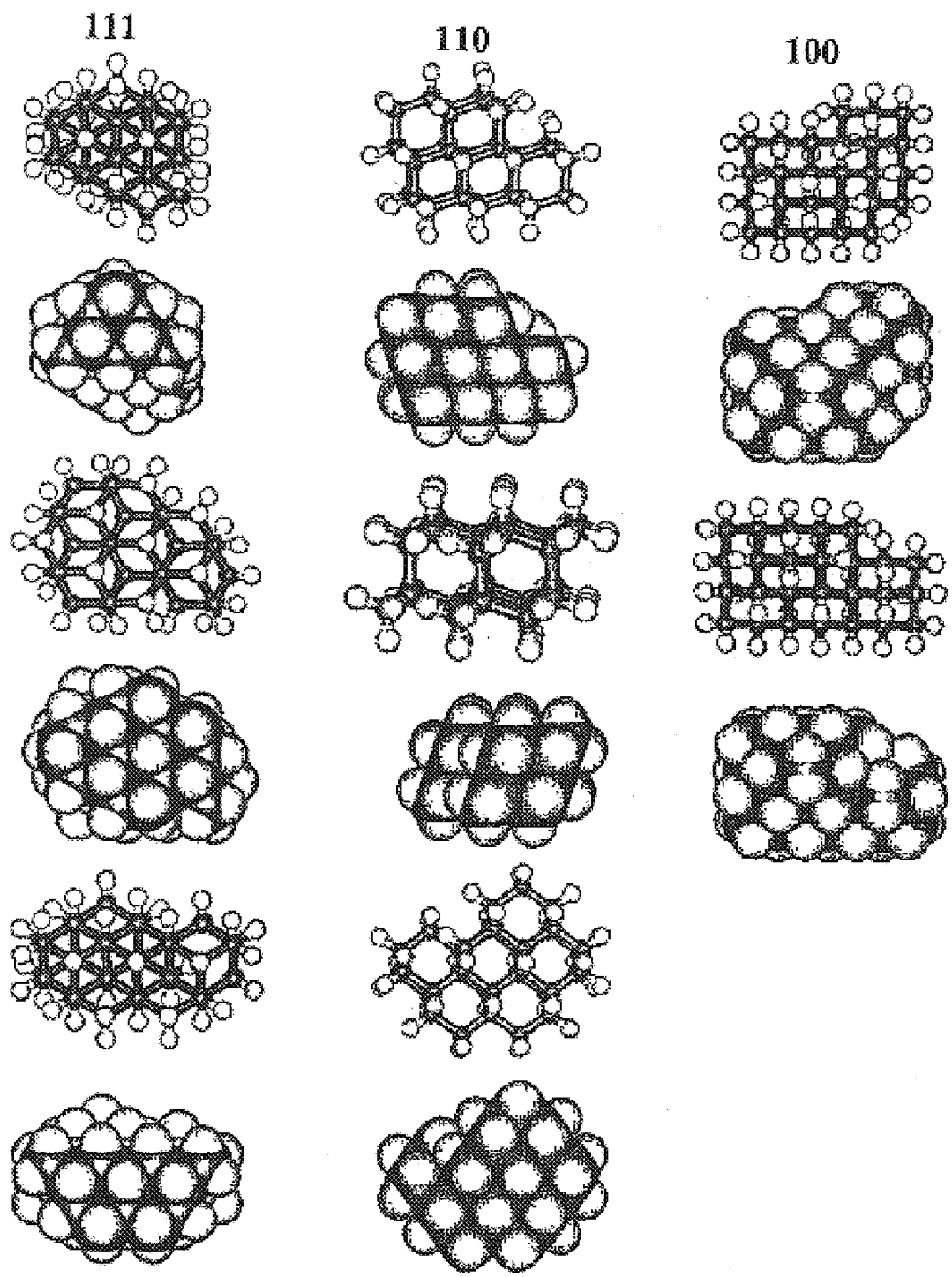
Figure 31:
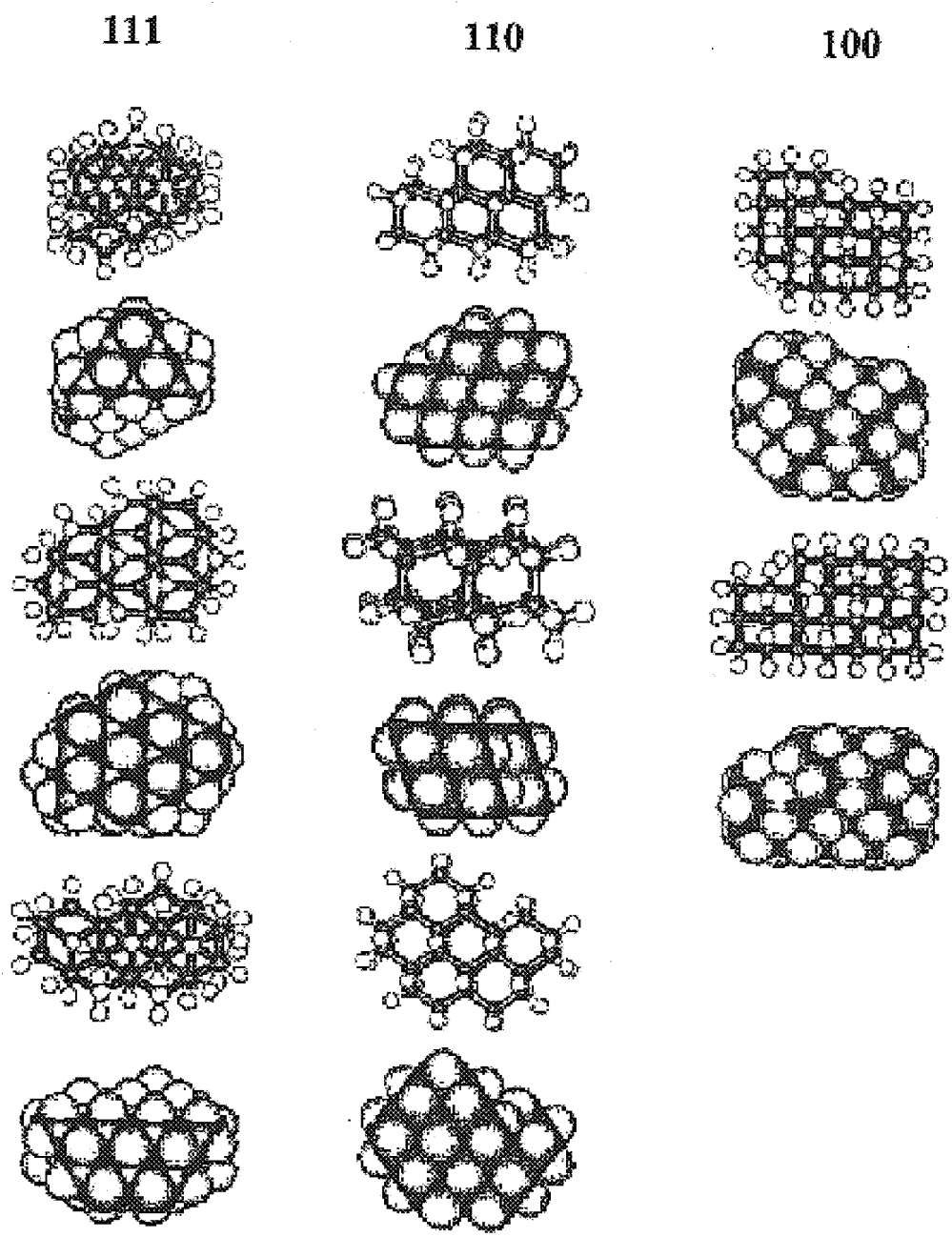
Figure 33:
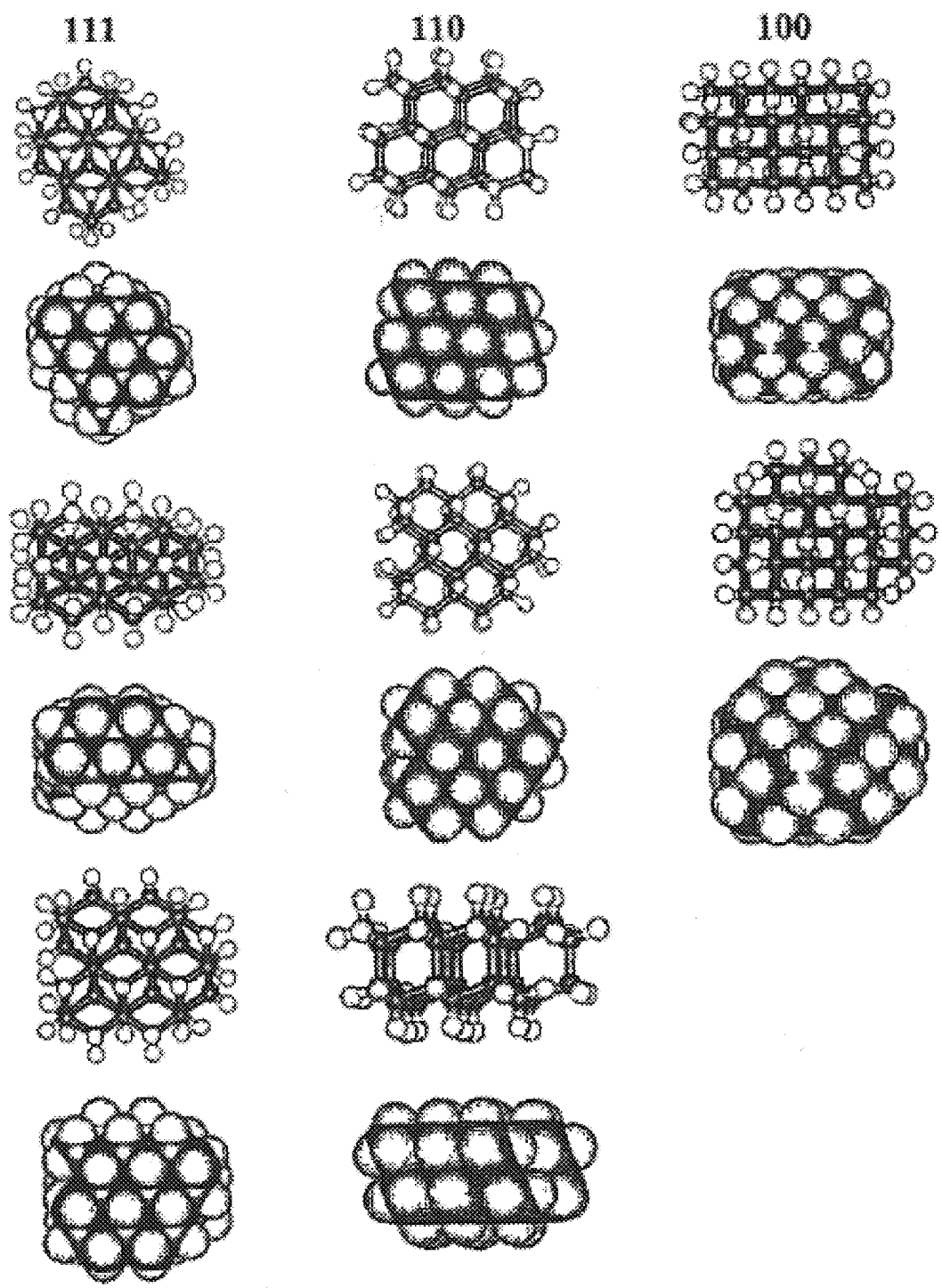
Figure 37:
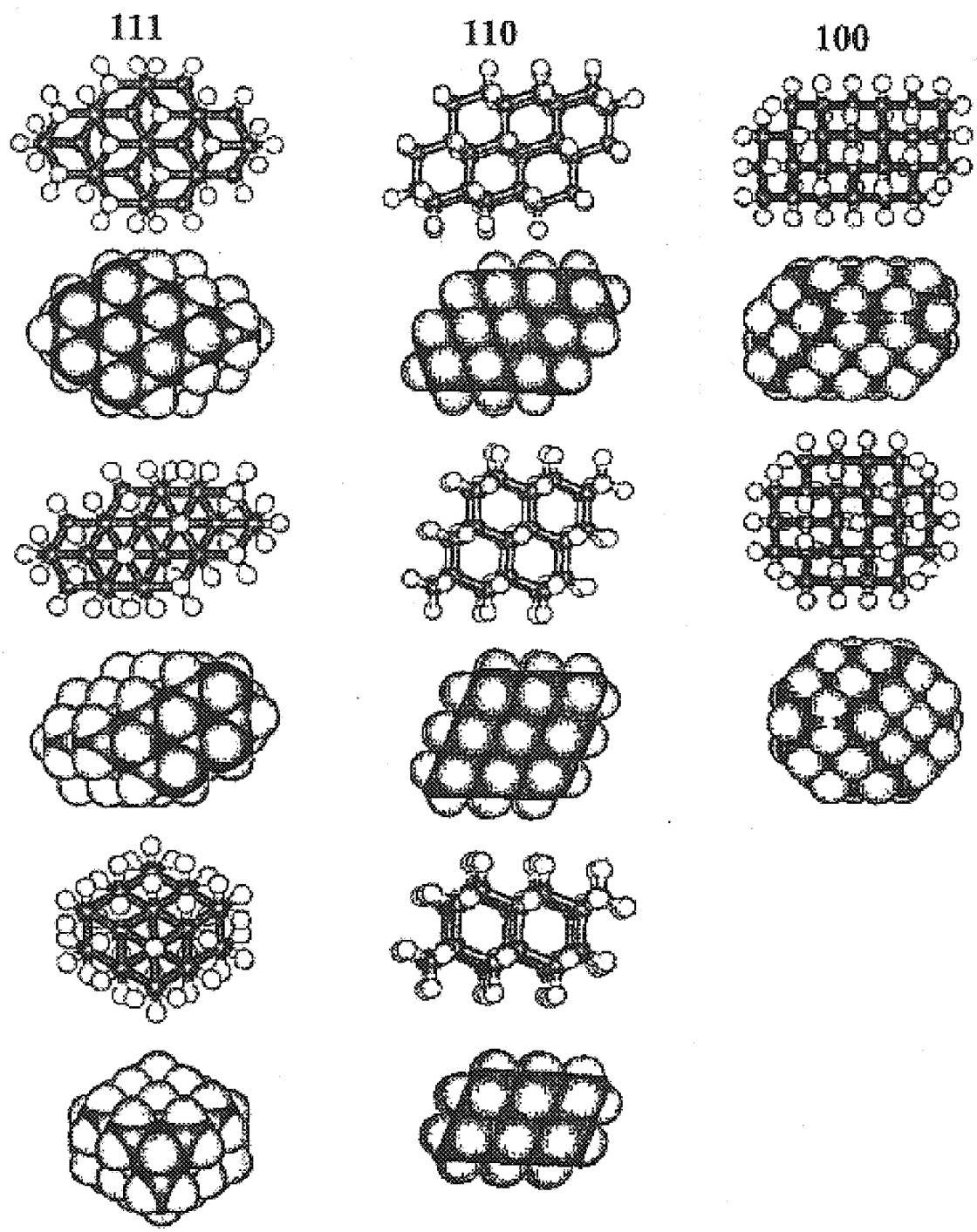
Figure 39:
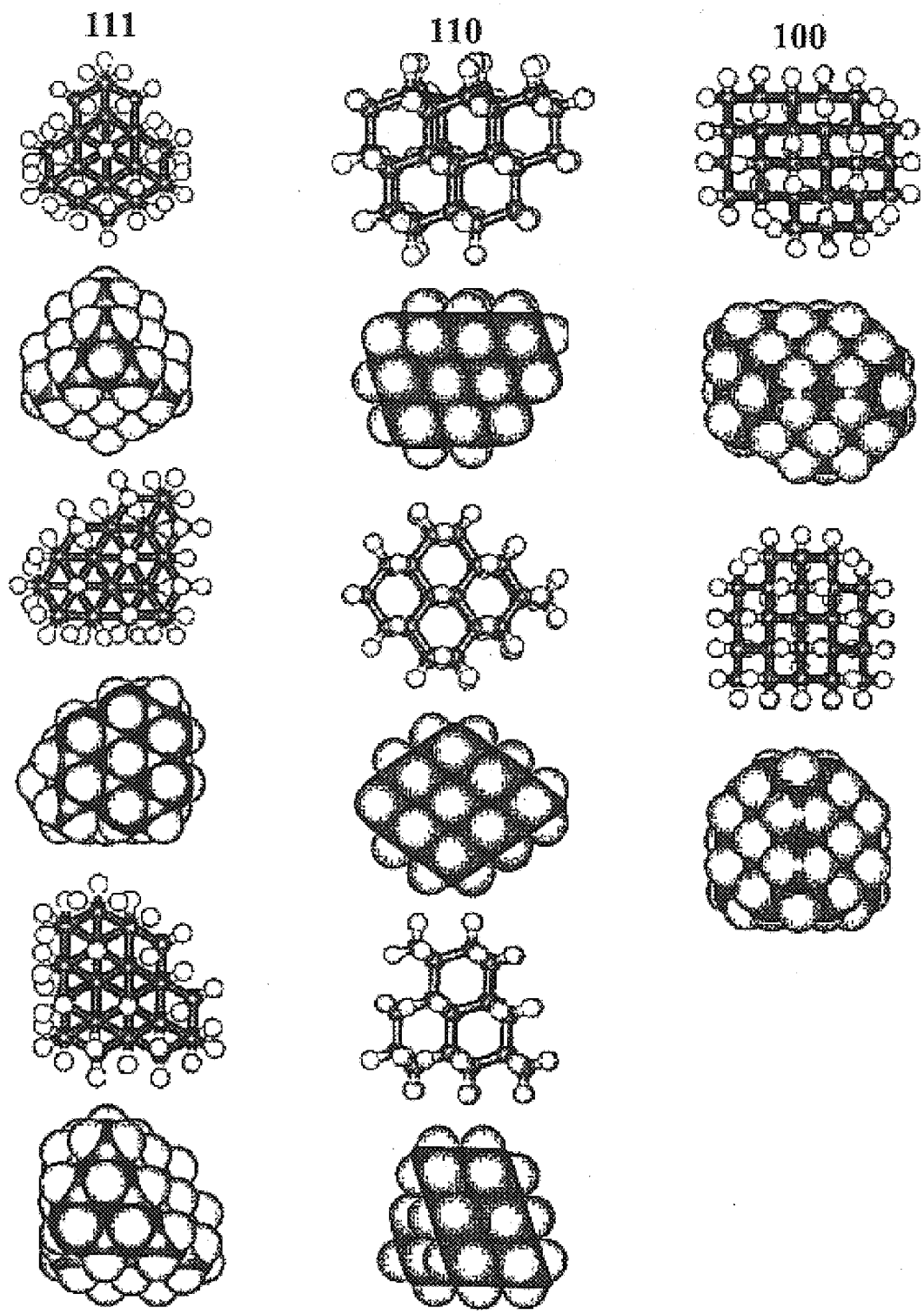
Figure 41:
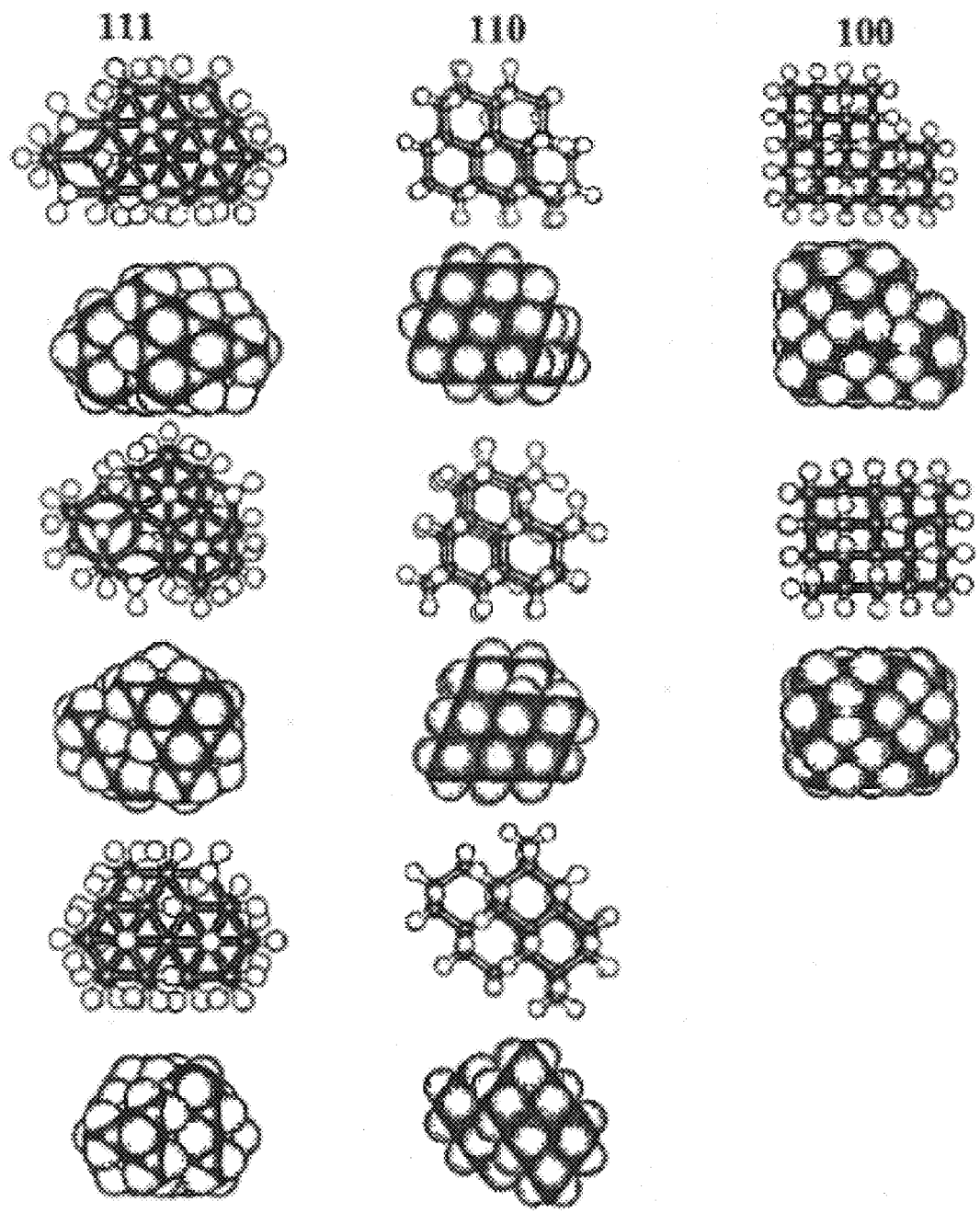
Figure 43:
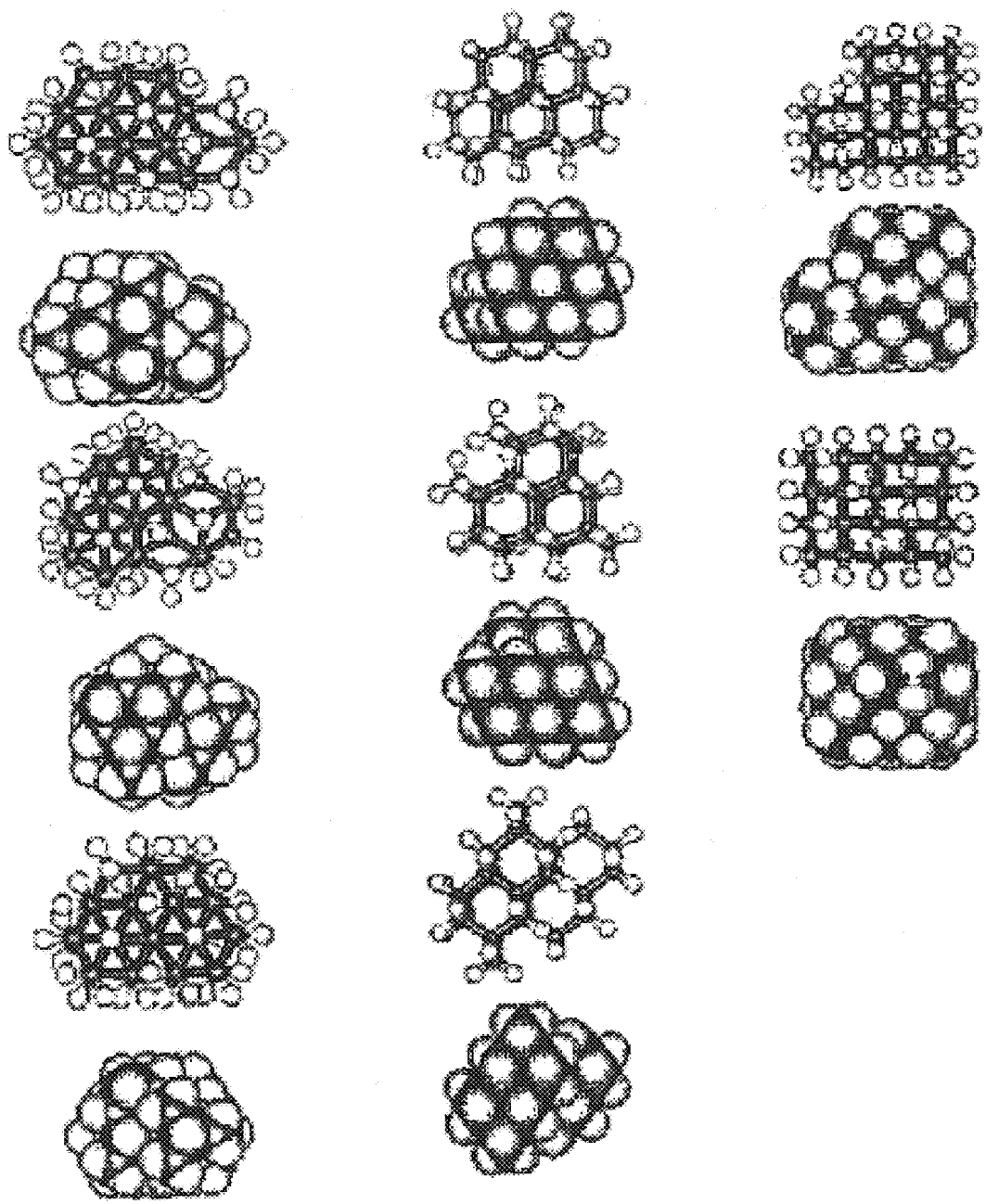
Figure 45:
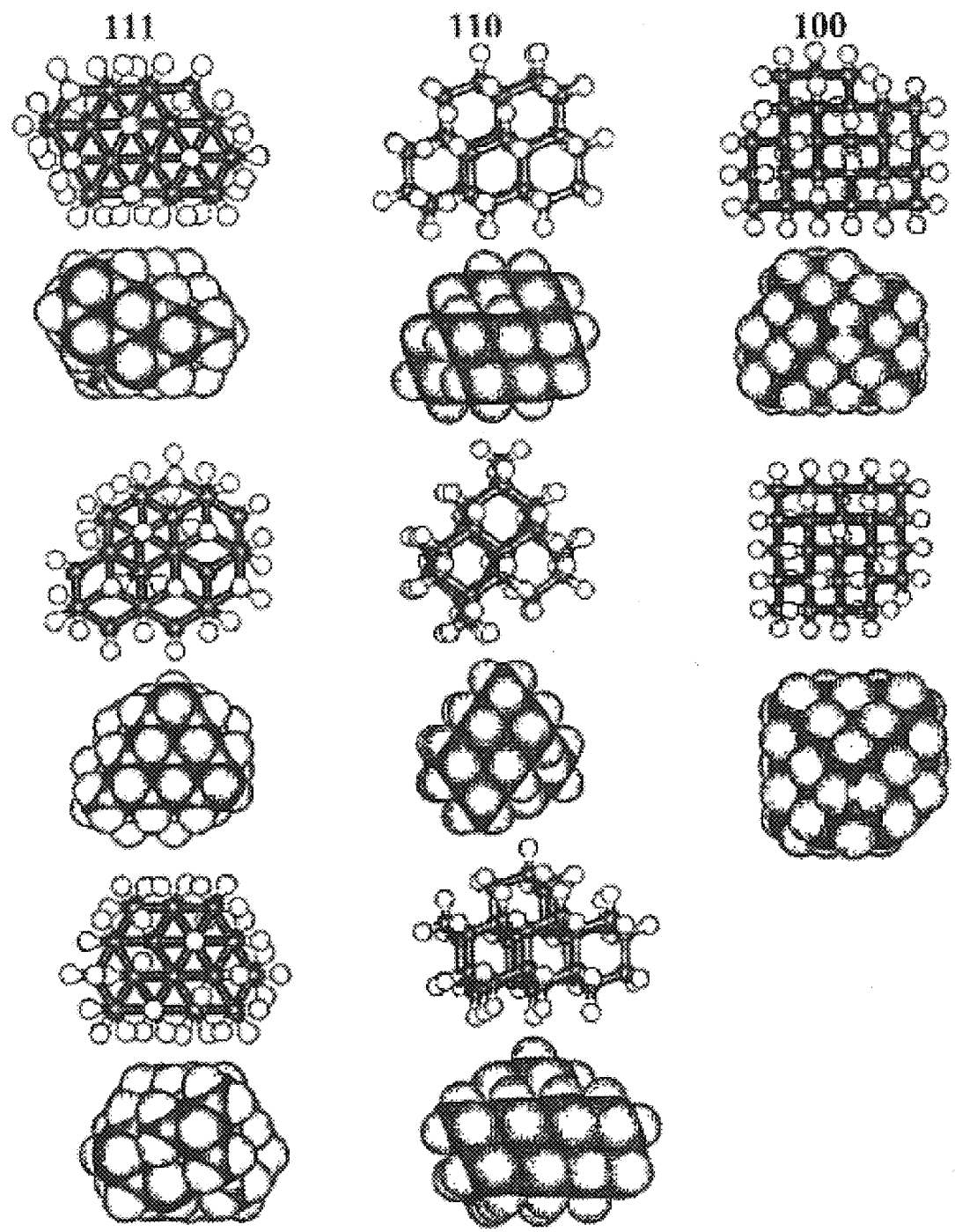
Figure 47:
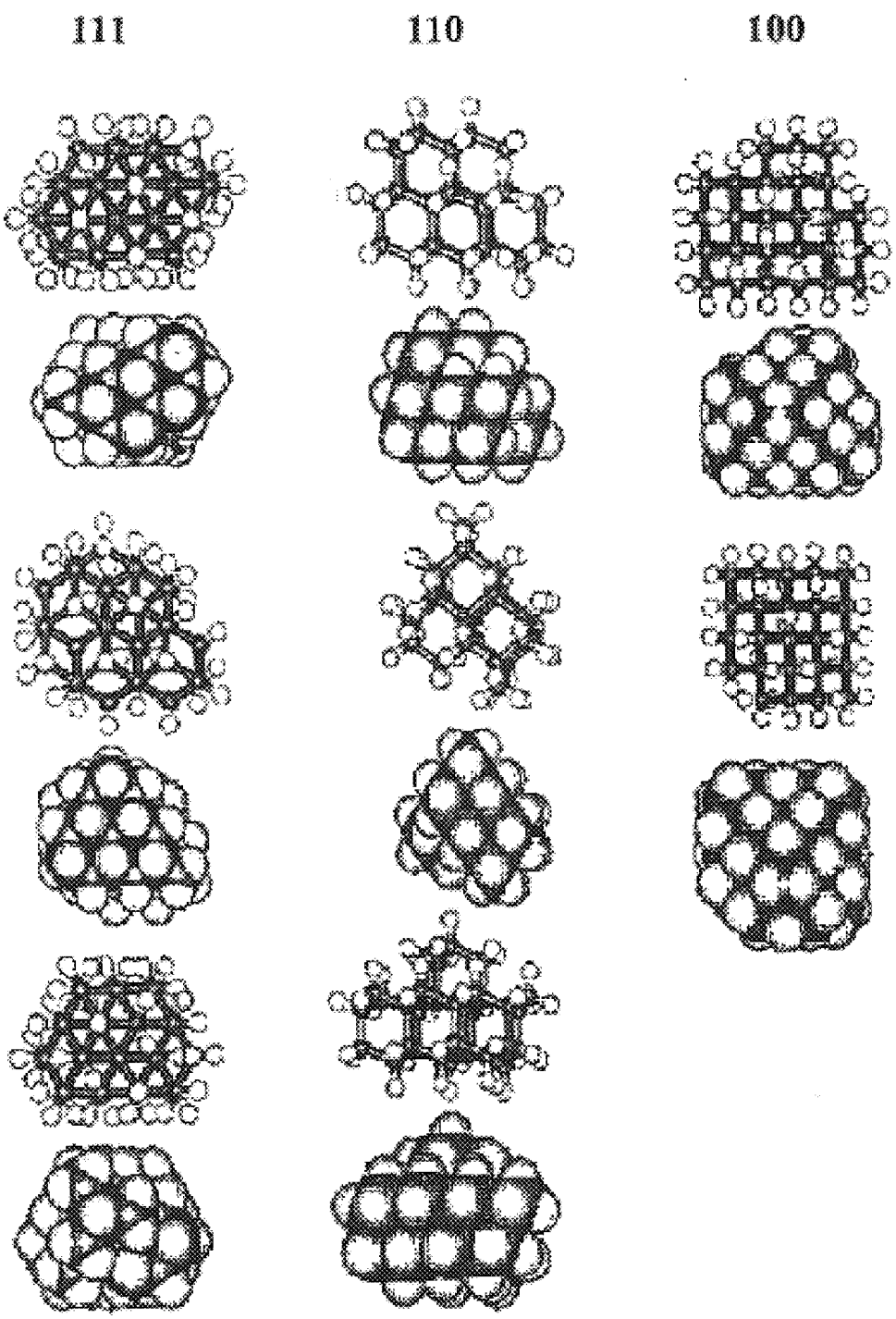
Figure 49:
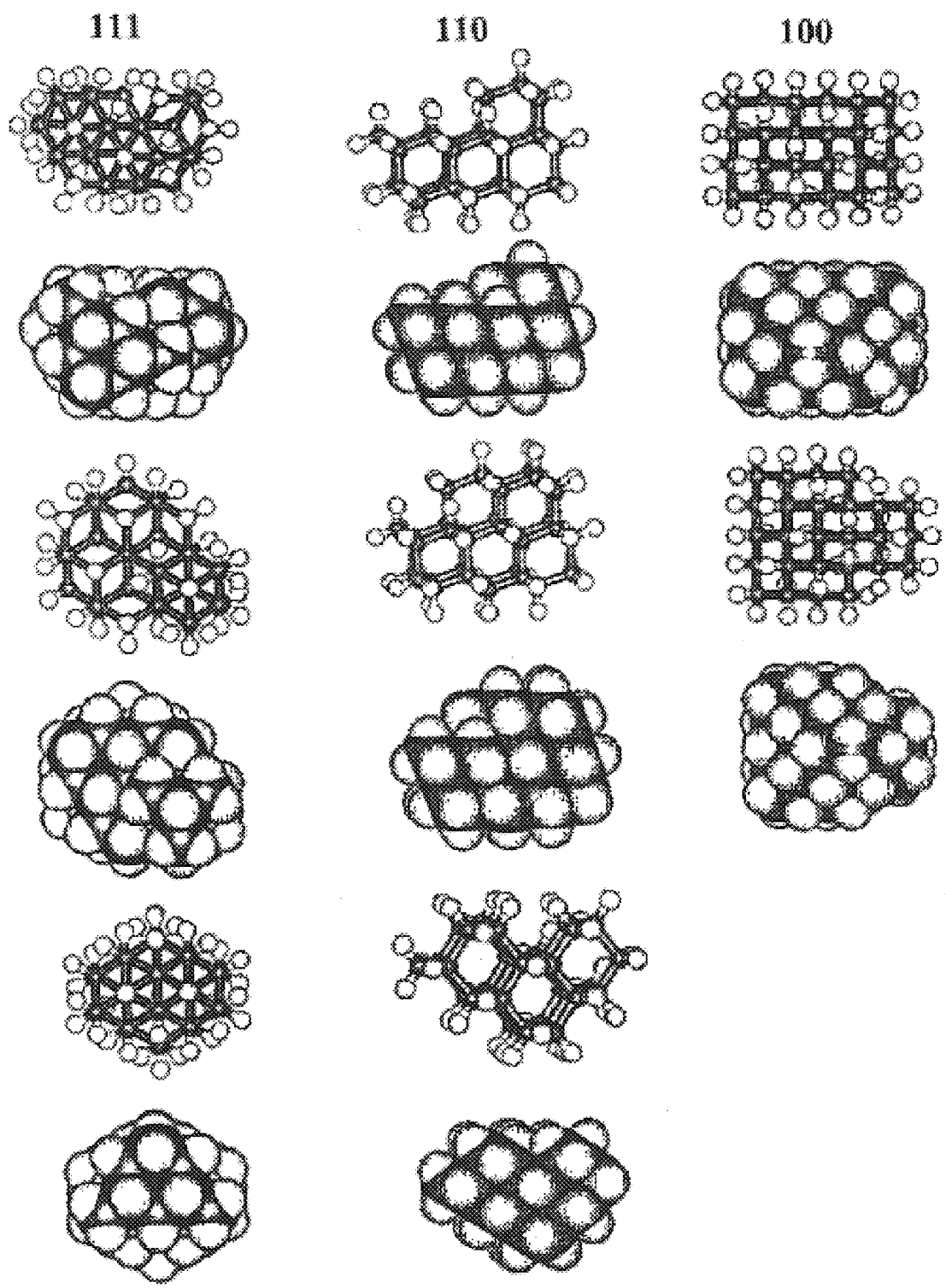
Figure 51:
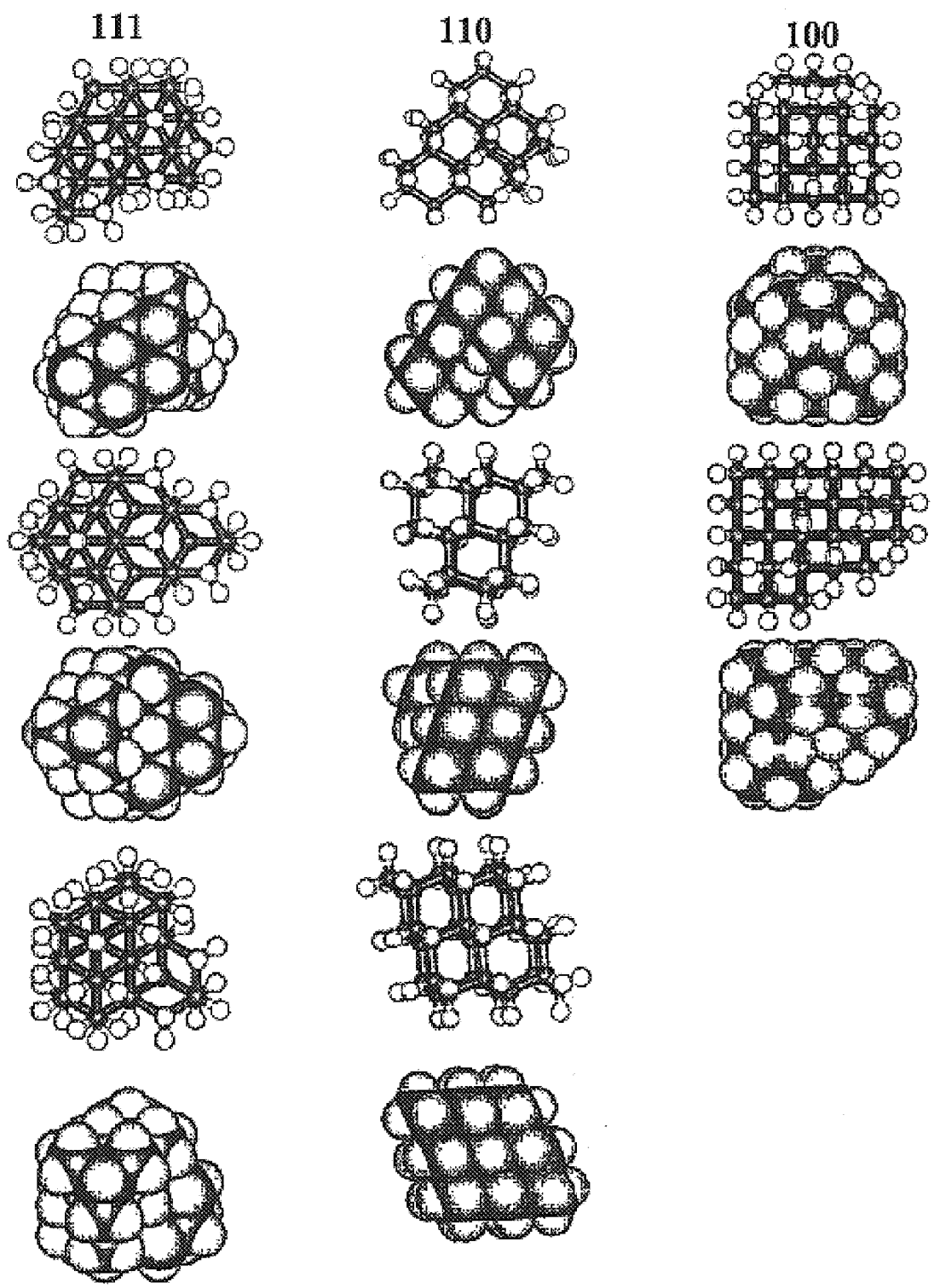
Figure 53:
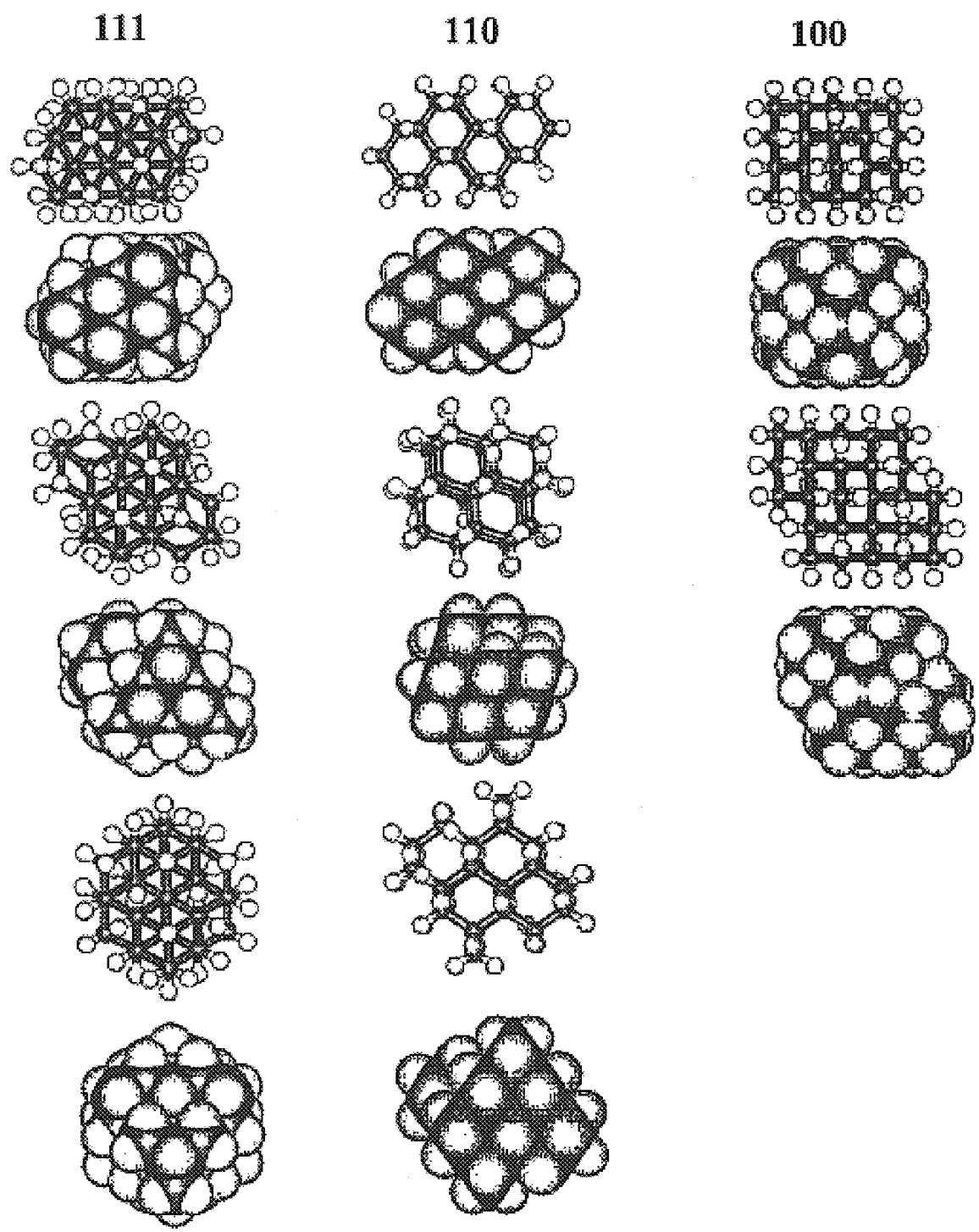
Figure 55:
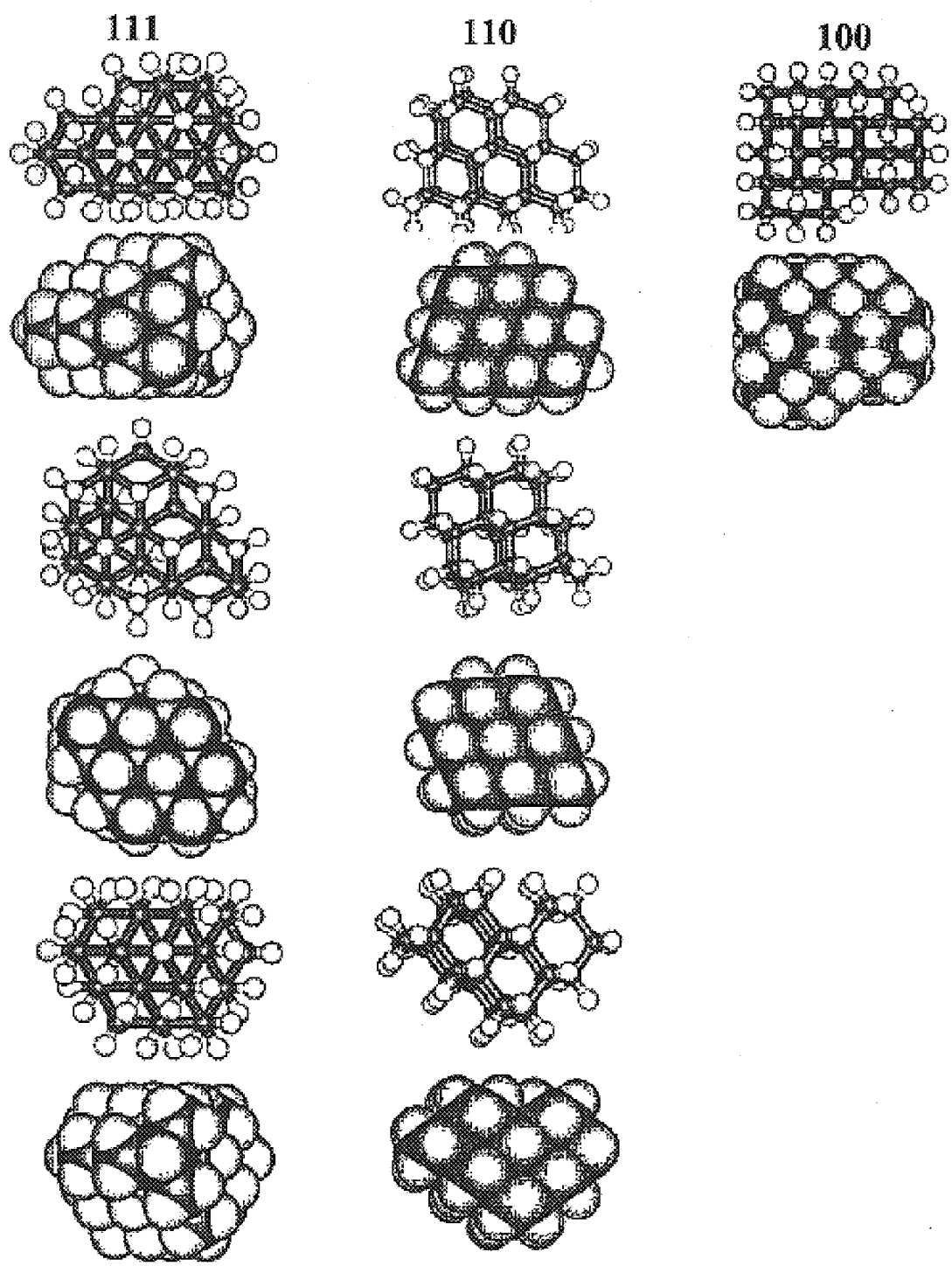
Figure 57:
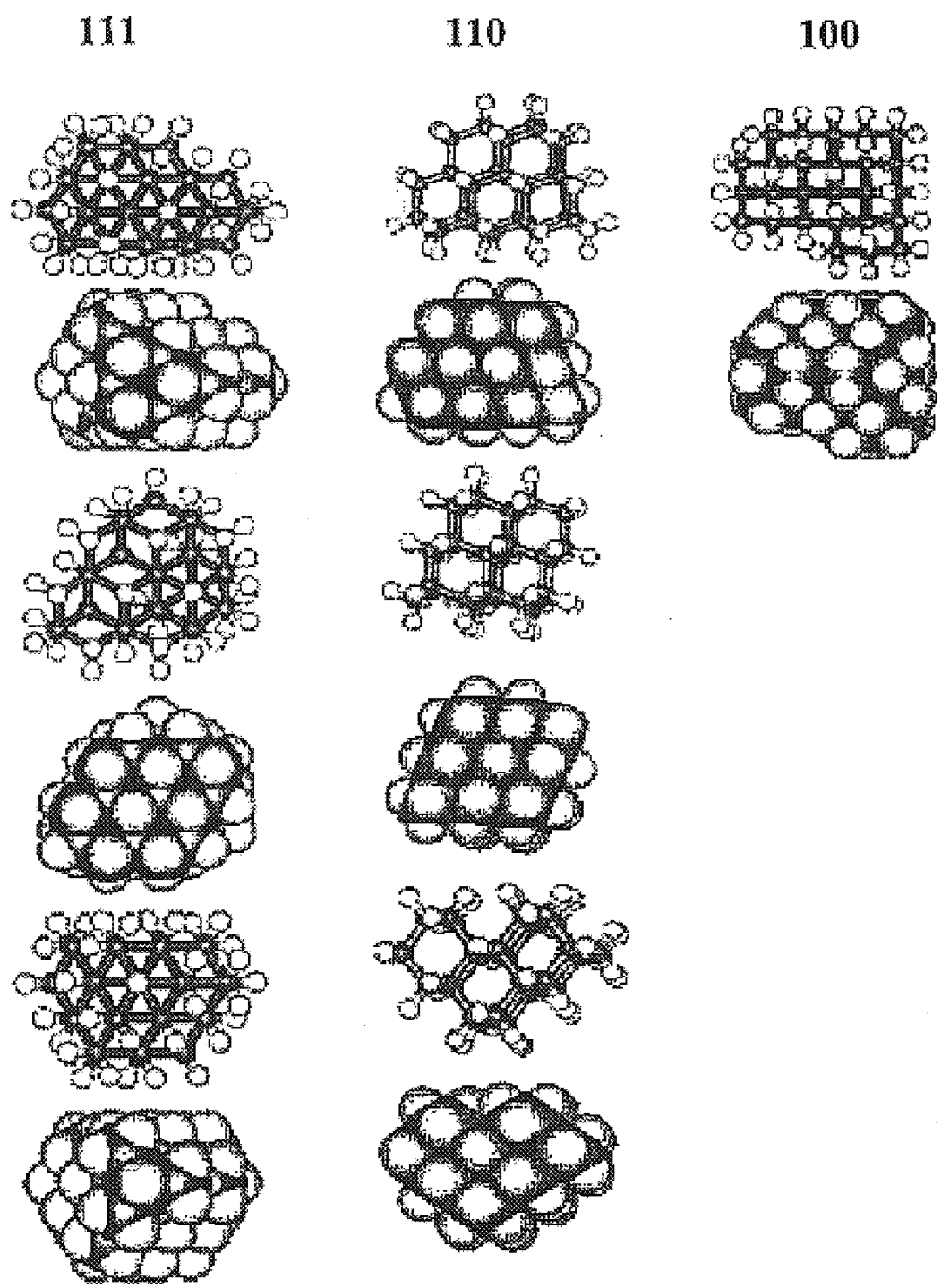
Figure 59:
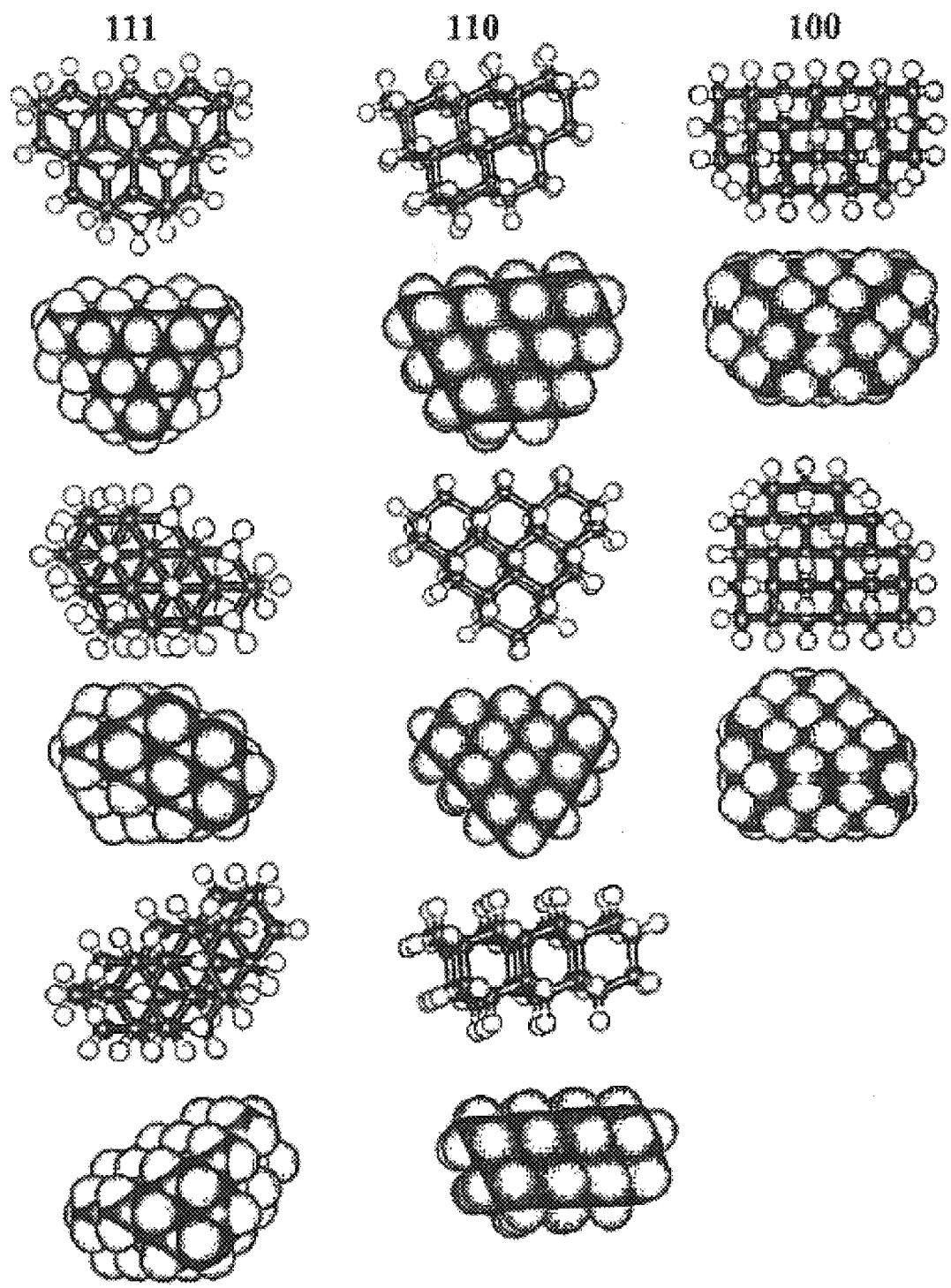

The highly concentrated heptamantanes were then allowed to crystallize either directly in the trap or from solution. Under the microscope at 30×magnification, the crystals of heptamantane #1 were visible in preparative GC trap fraction 2 (see FIG. 20). These crystals were perfectly clear and showed high refractive index. Crystals of heptamantane #1 had never existed before this isolation. FIG. 21 is a photomicrograph of heptamantane #2 that crystallized in preparative GC trap 4. Crystals of heptamantane #2 had never existed before this isolation. Where concentrations are not high enough for crystallization to occur, further concentration by preparative GC may be necessary.

Example 4

Purification of Single Isomers Using Dual Column Selectivity

As shown in Example 1, some octamantanes can be isolated in high purity by using a single type of HPLC column (FIG. 9). For isolation in high purity of other octamantane components for example (FIGS. 13, 15 and 16), multiple columns can be employed. To illustrate this methodology, HPLC columns of different selectivities were used in succession to isolate single heptamantanes. The first HPLC system consisted of two Whatman M20 10/50 ODS columns operated in series using acetone as mobile phase at 5.00 mL/min. The detector used was a differential refractometer. From this HPLC run, fraction 41 was taken for further purification on a second HPLC system. This fraction 41 contained heptamantane #2 and various impurities.

To purify HPLC fraction 41 from the ODS, we injected a 50 microliter sample of approximately 1 mg of ODS HPLC fraction 41 in acetone onto a Hypercarb column, 10 mm I.D.×250 mm, operated using acetone at 3.00 mL/min as mobile phase (@480 psi), and using a differential refractometer detector.

FIG. 22 shows the GC/MS total ion chromatogram (TIC) of the isolated heptamantane #2 containing Hypercarb HPLC fraction. The lower half of FIG. 22 illustrates the mass spectrum of the GC/MS peak, demonstrating the high purity of the isolated heptamantane #2.

By using a similar methodology as above, i.e. fractionating octamantane containing ODS HPLC fractions using columns with different selectivities, such as the Hypercarb or other suitable columns, we could isolate the remaining octamantanes in high purity. This is also expected to be true of the octamantanes with molecular weights of 500, and the octamantanes of molecular weights 486, 472 and 432, which respectively are in lower abundance in our feedstocks. An octamantane of molecular weight 500 shows up in ODS HPLC fraction #92 (FIG. 16) with a very strong molecular ion in the mass spectrum (in this case m/z 500) for the 500 molecular weight component running at 17.245 min. The mass spectrum, with its prominent molecular ion and low number and abundance of fragments is characteristic of a diamondoid component.

The enantiomeric octamantanes are not resolved in GS/MS and therefore, these enantiomeric pairs are referenced within a single number. These enantiomers can be isolated by chiral separation methods.

Figure 61:
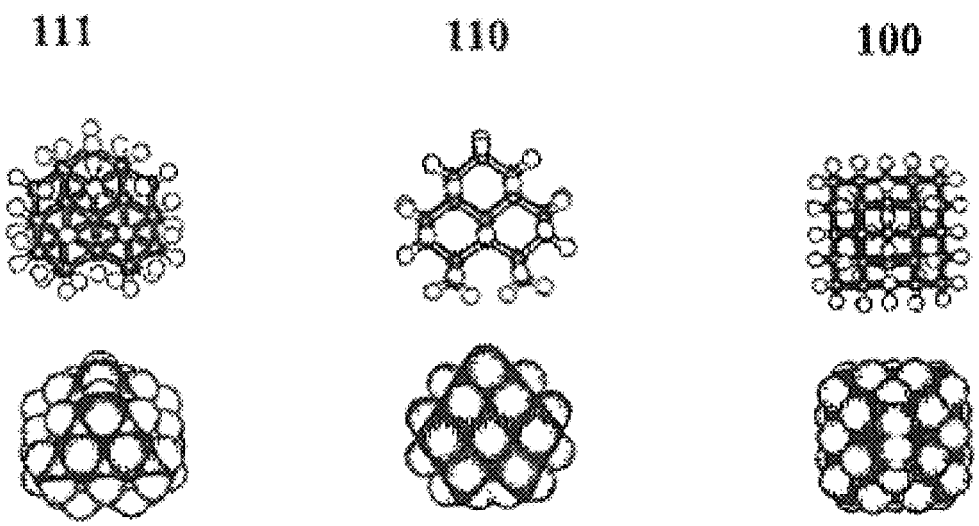
Figure 63:
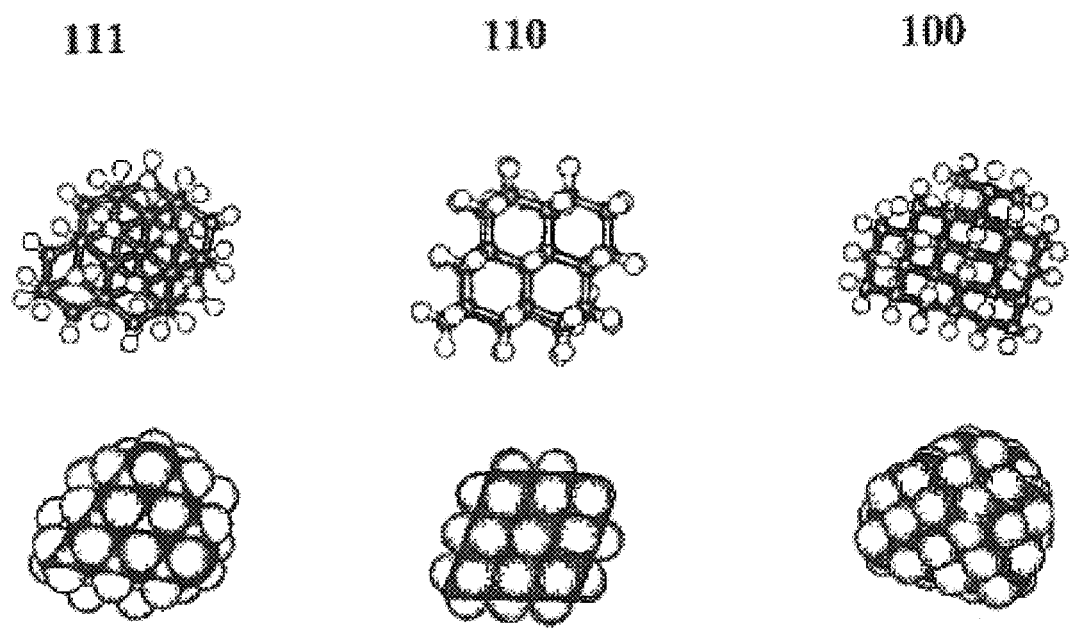

FIGS. 24 through 59 illustrate the structures with views into various diamond crystal lattice planes for each of the eighteen, molecular formula $C_{34}H_{38}$ (molecular weight 446) octamantane structures. In a similar fashion, FIGS. 60–61 illustrate an example ball and stick, stick with hydrogen removed, and CPK model of a molecular formula $C_{33}H_{36}$ (molecular weight 432) octamantane; and FIGS. 62–63 illustrate an example ball and stick, stick with hydrogen removed, and CPK model of a molecular formula $C_{36}H_{40}$ (molecular weight 472) octamantane; and FIGS. 64–65 illustrate an example ball and stick, stick with hydrogen removed, and CPK model of a molecular formula $C_{37}H_{42}$ (molecular weight 486) octamantane; and lastly FIGS. 66–67 illustrate an example ball and stick, stick with hydrogen removed, and CPK model of a molecular formula $C_{38}H_{44}$ (molecular weight 500) octamantane.

Example 5

Isolation of Substituted Octamantanes

Substituted octamantanes also are present in Feedstock A and B. These natural occurring substituted octamantanes have uses similar to the unsubstituted octamantanes and can be de-alkylated to yield the corresponding unsubstituted octamantane. Accordingly, methods for the isolation of individual substituted octamantanes were devised and exemplified by the isolation of alkyl substituted compounds.

Alkyloctamantanes can be purified using methodologies described for non-alkylated octamantanes given in Examples 1 and 3. FIGS. 23(A/B) shows that ODS HPLC fraction 94 contains a methylated octamantane in high purity. Monomethylated octamantanes have a molecular weight of 460 (yielding a mass spectrometric molecular ion of m/z 460, and show a mass spectrometric loss of the methyl group giving the m/z 445 mass spectrometric fragment ion indicative of an octamantane moiety (FIG. 22B). Also, where more than one alkyloctamantane is present in an ODS or Hypercarb HPLC fraction, an additional HPLC separation of that fraction or an alternative preparative GC procedure (as in Example 3) can yield high purity alkyloctamantanes.

What is claimed is:

1. A composition comprising diamondoids wherein at least about 25 weight percent of the diamondoids are one or more octamantane components.

2. A composition of claim 1 wherein from 50 to 100 weight percent of the diamondoids are one or more octamantane components.

3. A composition of claim 1 wherein from 70 to 100 weight percent of the diamondoids are one or more octamantane components.

4. A composition of claim 1 wherein from 95 to 100 weight percent of the diamondoids are one or more octamantane components.

5. A composition of claim 1 wherein from 99 to 100 weight percent of the diamondoids are one or more octamantane components.

6. The composition of any of claims 1–5, wherein the one or more octamantane components are a single octamantane component.

7. The composition of any of claims 1–5 wherein the one or more octamantane components are isolated optical isomers.

8. The composition of any of claims 1–5, wherein the one or more octamantane components are isomeric octamantane components.

9. The composition of any of claims 1–5, wherein the one or more octamantane components are one or more isomeric octamantane components represented by the formula $C_{33}H_{36}$.

10. The composition of any of claims 1–5, wherein the one or more octamantane components are one or more isomeric octamantane components represented by the formula $C_{34}H_{38}$.

11. The composition of any of claims 1–5, wherein the one or more octamantane components are one or more isomeric octamantane components represented by the formula $C_{36}H_{40}$.

12. The composition of any of claims 1–5, wherein the one or more octamantane components are one or more isomeric octamantane components represented by the formula $C_{37}H_{42}$.

13. The composition of any of claims 1–5, wherein the one or more octamantane components are one or more isomeric octamantane components represented by the formula $C_{38}H_{44}$.

14. The composition of any of claims 1–5 wherein the octamantane components comprise unsubstituted octamantane components.

15. The composition of any of claims 1–5 wherein the octamantane components comprise substituted octamantane components having from 1 to 10 alkyl substituents.

16. A composition comprising at least about 10% by weight of one or more octamantane components.

17. The composition of claim 16 containing from 50 to 100% by weight of one or more octamantane components.

18. The composition of claim 16 containing from 70 to 100% by weight of one or more octamantane components.

19. The composition of claim 16 containing from 95 to 100% by weight of one or more octamantane components.

20. The composition of claim 16 containing from 99 to 100% by weight of one or more octamantane components.

21. The composition of claims 16–20 wherein the one or more octamantane components are a single octamantane component.

22. The composition of claim 1, wherein the one or more octamantane components are in crystalline form.

23. A process for recovering a composition enriched in one or more octamantane components which process comprises:
   a. selecting a feedstock comprising recoverable amounts of octamantane components and nonoctamantane components;
   b. removing from the feedstock a sufficient amount of nonoctamantane components having boiling points less than the lowest boiling point octamantane component under conditions to form a treated feedstock enriched in octamantane components which can be recovered;
   c. recovering a composition enriched in one or more octamantane components from said treated feedstock formed in b) above with one or more additional separation techniques selected from the group consisting of chromatographic techniques, thermal diffusion techniques, zone refining, progressive recrystallization and size separation techniques.

24. A process for recovering a composition enriched in octamantane components which process comprises:
   a. selecting a feedstock comprising recoverable amounts of octamantane components and nonoctamantane components including nondiamondoid components;
   b. removing from the feedstock a sufficient amount of nonoctamantane components having a boiling point less than the lowest boiling point octamantane component under conditions to form a treated feedstock enriched in octamantane components which can be recovered;
   c. thermally degrading said treated feedstock to pyrolyze at least a sufficient amount of nondiamondoid components therefrom under conditions to form a thermally treated feedstock retaining recoverable amounts of octamantane;
   d. recovering a composition enriched in one or more octamantane components from said thermally treated feedstock formed in c) above with one or more additional separation techniques selected from the group consisting of chromatographic techniques, thermal diffusion techniques, zone refining, progressive recrystallization and size separation techniques.

25. A process for recovering a composition enriched in one or more octamantane components which process comprises:
   a. selecting a feedstock comprising recoverable amounts of octamantane components and nonoctamantane components including nondiamondoid components;
   b. thermally degrading said feedstock to pyrolyze at least a sufficient amount of nondiamondoid components therefrom under conditions to provide a thermally treated feedstock retaining recoverable amounts of octamantane;
   c. removing from the thermally treated feedstock a sufficient amount of nonoctamantane components having a boiling point less than the lowest boiling point of octamantane component under conditions to form a treated feedstock enriched in octamantanes components which can be recovered;

d. recovering a composition enriched in one or more octamantane components from said treated feedstock recovered in c) above with one or more additional separation techniques selected from the group consisting of chromatographic techniques, thermal diffusion techniques, zone refining, progressive recrystallization and size separation techniques.

26. A process for recovering a composition enriched in one or more octamantane components which process comprises:

a. selecting a feedstock comprising recoverable amounts of octamantane components and nonoctamantane components;

b. fractionating the feedstock to form one or more cuts enriched in materials having boiling points in the range of from just below the boiling point of the lowest boiling octamantane component to just above the boiling point of the highest boiling octamantane component;

c. recovering a composition enriched in one or more octamantane components from said one or more cuts formed in b) above with one or more additional separation techniques selected from the group consisting of chromatographic techniques, thermal diffusion techniques, zone refining, progressive recrystallization and size separation techniques.

27. A process for recovering a composition enriched in one or more octamantane components which process comprises:

a. selecting a feedstock comprising recoverable amounts of octamantane components and nonoctamantane components including nondiamondoid components;

b. fractionating the feedstock to form one or more cuts enriched in materials having boiling points in the range of from just below the boiling point of the lowest boiling octamantane component to just above the boiling point of the highest boiling octamantane component;

c. thermally degrading one or more cuts said to pyrolyze at least a sufficient amount of nondiamondoid components therefrom under conditions to form one or more thermally treated cuts retaining recoverable amounts of octamantane;

d. recovering a composition comprising one or more octamantane components from one or more said thermally treated cuts formed in c) above with one or more additional separation techniques selected from the group consisting of chromatographic techniques, thermal diffusion techniques, zone refining, progressive recrystallization and size separation techniques.

28. A process for recovering a composition enriched in one or more octamantane components which process comprises:

a. selecting a feedstock comprising recoverable amounts of octamantane components and nonoctamantane compounds including nondiamondoid components;

b. thermally degrading said feedstock to pyrolyze at least a sufficient amount of nondiamondoid components therefrom under conditions to provide a thermally treated feedstock retaining recoverable amounts of octamantane;

c. fractionating the thermally treated feedstock to form one or more cuts enriched in materials having boiling points in the range of from just below the boiling point of the lowest boiling octamantane component to just above the boiling point of the highest boiling octamantane component;

d. recovering a composition enriched in one or more octamantane components from one or more cuts formed c) above with one or more additional separation techniques selected from the group consisting of chromatographic techniques, thermal diffusion techniques, zone refining, progressive recrystallization and size separation techniques.

29. The process according to any of claims 26–28 wherein said boiling point range is a range having atmospheric equivalents of between about 370° C. to about 610° C.

30. The process according to any of claims 23–28 wherein said separation technique is a chromatographic technique.

31. The process according to claim 30 wherein said chromatographic technique is selected from the group consisting of liquid chromatography, preparative gas chromatography and high performance liquid chromatography.

32. The process according to claim 30 wherein said additional separation technique is high performance liquid chromatography comprising one or more high performance liquid chromatography columns.

33. The process according to claim 32 wherein the high performance liquid chromatography columns are selected to have a different specificity to the octamantane components.

34. A product prepared by the process of claim 23.

35. A product prepared by the process of claim 24.

36. A product prepared by the process of claim 25.

37. A product prepared by the process of claim 26.

38. A product prepared by the process of claim 27.

39. A product prepared by the process of claim 28.

* * * * *